US011934572B2

(12) United States Patent
Forutanpour et al.

(10) Patent No.: US 11,934,572 B2
(45) Date of Patent: Mar. 19, 2024

(54) DYNAMIC CONTENT PRESENTATION FOR EXTENDED REALITY SYSTEMS

(71) Applicant: QUALCOMM Incorporated, San Diego, CA (US)

(72) Inventors: Bijan Forutanpour, San Diego, CA (US); Jonathan Kies, Encinitas, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/454,188

(22) Filed: Nov. 9, 2021

(65) Prior Publication Data

US 2023/0144091 A1    May 11, 2023

(51) Int. Cl.

| | |
|---|---|
| *G06F 3/01* | (2006.01) |
| *A61B 5/16* | (2006.01) |
| *G06V 20/20* | (2022.01) |
| G02B 27/01 | (2006.01) |
| G06V 10/10 | (2022.01) |
| G06V 40/19 | (2022.01) |

(52) U.S. Cl.
CPC .............. *G06F 3/013* (2013.01); *A61B 5/163* (2017.08); *G02B 2027/0138* (2013.01); *G06F 3/011* (2013.01); *G06V 10/17* (2022.01); *G06V 20/20* (2022.01); *G06V 40/19* (2022.01)

(58) Field of Classification Search
CPC ......... G06F 3/013; G06F 3/011; A61B 5/163; G02B 2027/0138; G06V 10/17; G06V 20/20; G06V 40/19
See application file for complete search history.

(56) References Cited

U.S. PATENT DOCUMENTS

| | | | |
|---|---|---|---|
| 5,724,987 A * | 3/1998 | Gevins ..................... | A61B 5/16 434/258 |
| 8,379,918 B2 * | 2/2013 | Pfleger ................... | A61B 5/163 348/78 |
| 8,767,014 B2 * | 7/2014 | Vaught .................... | G06F 3/013 345/633 |

(Continued)

OTHER PUBLICATIONS

International Search Report and Written Opinion—PCT/US2022/078395—ISA/EPO—dated Jan. 31, 2023.

*Primary Examiner* — Mihir K Rayan
(74) *Attorney, Agent, or Firm* — QUALCOMM Incorporated

(57) ABSTRACT

Systems and techniques are described for extended reality (XR) operations. An XR system displays virtual content using a display according to display settings. The display settings can identify, for instance, a position, orientation, and/or size of the virtual content as displayed. The environment can be viewable using the display as the virtual content is displayed by the display, for example using a see-through display or a pass-through display. The imaging system can determine, based on one or more attributes of one or both eyes of the user of the imaging system, an extent of perception of the virtual content that is displayed using the display by the user. The attributes can identify, for instance, eye position, eye movement, pupil dilation, saccades, fixations, blinking, and/or squinting. The XR system can determine, based on the extent of perception of the virtual content by the user, a modification to the display settings.

36 Claims, 12 Drawing Sheets

(56) References Cited

U.S. PATENT DOCUMENTS

| | | | | |
|---|---|---|---|---|
| 9,478,143 | B1* | 10/2016 | Bowen | G09B 5/062 |
| 2003/0020755 | A1* | 1/2003 | Lemelson | G06F 3/013 |
| | | | | 715/786 |
| 2011/0159467 | A1* | 6/2011 | Peot | G09B 7/06 |
| | | | | 434/157 |
| 2011/0257961 | A1* | 10/2011 | Tinkler | G09B 7/06 |
| | | | | 434/156 |
| 2013/0021373 | A1* | 1/2013 | Vaught | G06F 3/013 |
| | | | | 345/633 |
| 2015/0074602 | A1* | 3/2015 | VanBlon | G06F 3/013 |
| | | | | 715/815 |
| 2015/0213634 | A1* | 7/2015 | Karmarkar | A61B 5/163 |
| | | | | 345/589 |
| 2015/0331240 | A1* | 11/2015 | Poulos | G02B 27/017 |
| | | | | 345/8 |
| 2018/0004287 | A1* | 1/2018 | Yoo | G06F 3/0482 |
| 2018/0184974 | A1* | 7/2018 | Cimenser | A61B 5/38 |
| 2018/0190269 | A1* | 7/2018 | Lokeswarappa | G09B 19/06 |
| 2021/0311548 | A1* | 10/2021 | Peterson | G06F 3/013 |

* cited by examiner

DYNAMIC CONTENT PRESENTATION FOR EXTENDED REALITY SYSTEMS

FIELD

This application is related to image processing. More specifically, this application relates to systems and methods of determining an level of a user's perception of virtual content, and modifying display settings for displaying the virtual content to the user based on the determined level of the user's perception of virtual content.

BACKGROUND

An extended reality (XR) device is a device that displays an environment to a user, for example through a head-mounted display (HMD) or other device. The environment is at least partially different from the real-world environment in which the user is in. The user can generally change their view of the environment interactively, for example by tilting or moving the HMD or other device. Virtual reality (VR) and augmented reality (AR) are examples of XR.

In some cases, an XR system can include an optical "see-through" display that allows the user to see their real-world environment based on light from the real-world environment passing through the display. In some cases, an XR system can include a digital "pass-through" display that allows the user to see a view of their real-world environment, or of a virtual environment based on their real-world environment, based on a view of the environment being captured by one or more cameras and displayed on the display. Optical "see-through" or digital "pass-through" XR systems can be worn by users while the users are engaged in activities in their real-world environment.

XR systems can overlay virtual content on top of a user's view of the environment. The virtual content can provide helpful information to a user of an XR system. However, there are situations in which virtual content may interfere with or distract a user from the user's activities in their real-world environment. On the other hand, there are situations in which a user might not notice virtual content that may have been helpful to the user, such as warnings.

BRIEF SUMMARY

In some examples, systems and techniques are described for extended reality (XR) content management. In some examples, an XR system causes virtual content to be displayed using a display according to display settings associated with the virtual content. The display settings can identify, for instance, a position, orientation, and/or size of the virtual content as displayed on the display, and/or relative to portions of the environment viewable via the display. The environment can be viewable via the display as the virtual content is displayed by the display, for example via a see-through display or a pass-through display. The imaging system can determine, based on one or more positioning attributes of one or both eyes of the user of the imaging system, a level of perception of the virtual content that is displayed using the display by the user. The imaging system can determine the positioning attributes based on one or more sensors focused on the user, such as one or more cameras facing one or both eyes of the user. The positioning attributes can identify, for instance, eye position, eye movement, pupil dilation, saccades, fixations, blinking, squinting, optokinetic reflexes or responses, vestibulo-ocular reflexes or responses, accommodation reflexes or responses, or combinations thereof. In some examples, the determination of the level of perception of the virtual content by the imaging system can include a determination of a level of comprehension of the virtual content by the user. The level of comprehension of the virtual content by the user can be based on the level of perception of the virtual content by the user, a complexity of the virtual content, a uniqueness of the virtual content, historical data associated with the user, and/or contextual data. The imaging system can determine, based on the level of perception of the virtual content by the user and/or the level of comprehension of the virtual content by the user, a modification to the display settings corresponding to the virtual content. The modification to the display settings, can, for example, hide, remove, shrink, reduce prominence of, reduce priority of, or terminate display of the virtual content. The modification to the display settings, can, for example, emphasize, enlarge, move, reorient, increase prominence of, and/or increase priority of, the virtual content.

In one example, an apparatus for image processing is provided. The apparatus includes a memory and one or more processors (e.g., implemented in circuitry) coupled to the memory. The one or more processors are configured to and can: cause virtual content to be displayed using a display according to display settings associated with the virtual content, wherein an environment is viewable using the display as the virtual content is displayed by the display; determine, based on one or more perception-related attributes of a user, a level of perception of the virtual content that is displayed using the display by the user; and determine, based on the level of perception of the virtual content by the user, a modification to the display settings corresponding to the virtual content.

In another example, a method of image processing is provided. The method includes: causing virtual content to be displayed using a display according to display settings associated with the virtual content, wherein an environment is viewable using the display as the virtual content is displayed by the display; determining, based on one or more perception-related attributes of a user, a level of perception of the virtual content that is displayed using the display by the user; and determining, based on the level of perception of the virtual content by the user, a modification to the display settings corresponding to the virtual content.

In another example, a non-transitory computer-readable medium is provided that has stored thereon instructions that, when executed by one or more processors, cause the one or more processors to: cause virtual content to be displayed using a display according to display settings associated with the virtual content, wherein an environment is viewable using the display as the virtual content is displayed by the display; determine, based on one or more perception-related attributes of a user, a level of perception of the virtual content that is displayed using the display by the user; and determine, based on the level of perception of the virtual content by the user, a modification to the display settings corresponding to the virtual content.

In another example, an apparatus for image processing is provided. The apparatus includes: means for causing virtual content to be displayed using a display according to display settings associated with the virtual content, wherein an environment is viewable using the display as the virtual content is displayed by the display; means for determining, based on one or more perception-related attributes of a user, a level of perception of the virtual content that is displayed using the display by the user; and means for determining, based on the level of perception of the virtual content by the user, a modification to the display settings corresponding to the virtual content.

In some aspects, the one or more perception-related attributes of the user are associated with one or more eyes of the user. In some aspects, the one or more perception-related attributes of the user include at least one of: one or more attributes of one or more eyes of the user, one or more attributes of one or more facial expressions of the user, and one or more gestures of the user.

In some aspects, the environment is viewable using the display at least in part based on light from the environment passing through at least a portion of the display. In some aspects, the environment is viewable using the display at least in part based on causing a view of the environment to be displayed by the display.

In some aspects, determining the level of perception of the virtual content by the user includes using the one or more perception-related attributes of the user as inputs to one or more trained machine learning systems. In some aspects, the methods, apparatuses, and computer-readable medium described above further comprise: receiving, through a user interface, feedback corresponding to the level of perception of the virtual content by the user; and updating the one or more trained machine learning systems based on the feedback.

In some aspects, the methods, apparatuses, and computer-readable medium described above further comprise: receiving sensor data captured by one or more sensors, wherein the sensor data is indicative of one or more eyes of the user; and determining the one or more perception-related attributes of the user based on the sensor data. In some aspects, the methods, apparatuses, and computer-readable medium described above further comprise: the one or more sensors.

In some aspects, the methods, apparatuses, and computer-readable medium described above further comprise: determining the one or more perception-related attributes of the user based on sensor data captured by one or more image sensors, wherein the sensor data includes one or more images of one or more eyes of the user.

In some aspects, the methods, apparatuses, and computer-readable medium described above further comprise: determining a level of comprehension of the virtual content by the user based on the level of perception of the virtual content by the user, wherein determining the modification to the display settings based on the level of perception includes determining the modification to the display settings based on the level of comprehension. In some aspects, the methods, apparatuses, and computer-readable medium described above further comprise: receiving historical information associated with the user, wherein determining the level of comprehension of the virtual content by the user is based on the historical information about the user.

In some aspects, the methods, apparatuses, and computer-readable medium described above further comprise: determine a characteristic of the virtual content, wherein determining the level of perception of the virtual content by the user is based on the characteristic of the virtual content. In some aspects, the methods, apparatuses, and computer-readable medium described above further comprise: determining a level of complexity of the virtual content, wherein determining the level of perception of the virtual content by the user is based on the level of complexity of the virtual content. In some aspects, the methods, apparatuses, and computer-readable medium described above further comprise: determine a level of uniqueness of the virtual content, wherein determining the level of perception of the virtual content by the user is based on the level of uniqueness of the virtual content. In some aspects, the methods, apparatuses, and computer-readable medium described above further comprise: determining a level of distinctiveness of the virtual content relative to the environment, wherein determining the level of perception of the virtual content by the user is based on the level of distinctiveness of the virtual content relative to the environment.

In some aspects, the modification to the display settings corresponding to the virtual content comprises causing the display to stop displaying at least a portion of the virtual content. In some aspects, the modification to the display settings corresponding to the virtual content comprises causing the display to display at least a portion of the virtual content more prominently than before the modification. In some aspects, the modification to the display settings corresponding to the virtual content comprises a modification to one or more characteristics of the virtual content, wherein the one or more characteristics include at least one of a position, an orientation, a depth, a size, a color, a font size, a font color, a font, a language, and a layout.

In some aspects, determining the level of perception of the virtual content by the user includes determining that the user has perceived the virtual content. In some aspects, determining the level of perception of the virtual content by the user includes determining that the user has not perceived the virtual content. In some aspects, determining the level of perception of the virtual content by the user includes determining that the user has perceived the virtual content to a first level of perception of a plurality of levels of perception. In some aspects, determining the level of perception of the virtual content by the user includes determining that the user has perceived the virtual content to a second level of perception of a plurality of levels of perception.

In some aspects, the modification to the display settings is based on a likelihood that the virtual content is to be reviewed by the user in a threshold amount of time.

In some aspects, determining the level of perception of the virtual content by the user includes determining a confidence level corresponding to the level of perception of the virtual content by the user, wherein the modification to the display settings is based on the confidence level.

In some aspects, the one or more perception-related attributes of the user include one or more eye positions of one or more eyes of the user relative to the virtual content. In some aspects, the one or more perception-related attributes of the user include one or more characteristics of one or more saccades by one or more eyes of the user, wherein the one or more characteristics include at least one of a frequency, a duration, a timing, a saccade speed, a saccade amplitude, an eye position, and an eye movement. In some aspects, the one or more perception-related attributes of the user include one or more characteristics of one or more fixations by one or more eyes of the user, wherein the one or more characteristics include at least one of a frequency, a duration, a timing, an eye position, and an eye movement. In some aspects, the one or more perception-related attributes of the user include one or more characteristics of one or more pupil dilations by one or more eyes of the user, wherein the one or more characteristics include at least one of a frequency, a duration, a timing, a level of pupil dilation, an eye position, and an eye movement. In some aspects, the one or more perception-related attributes of the user include one or more characteristics of one or more blinks by one or more eyelids of the user, wherein the one or more characteristics include at least one of a frequency, a duration, a timing, a blink speed, an eye position, and an eye movement.

In some aspects, the one or more perception-related attributes of the user include one or more characteristics of one or more squints by one or more eyelids of the user, wherein the one or more characteristics include at least one of a frequency, a duration, a timing, a level of squinting, an eye position, and an eye movement.

In some aspects, the methods, apparatuses, and computer-readable medium described above further comprise: determining an extent of reading of a string of characters by the user based on the level of perception of the virtual content and a length of the string of characters, wherein the virtual content includes the string of characters.

In some aspects, the methods, apparatuses, and computer-readable medium described above further comprise: the display.

In some aspects, the methods, apparatuses, and computer-readable medium described above further comprise: determining, based at least in part on sensor data that includes a representation of one or more eyes of the user, at least one of the one or more perception-related attributes of the user, wherein one or more sensors are configured to capture the sensor data.

In some aspects, determining the level of perception of the virtual content by the user includes determining a level of comprehension of the virtual content by the user based on the one or more perception-related attributes of the user. In some aspects, determining the level of comprehension of the virtual content by the user is based on the one or more perception-related attributes of the user and at least one of: one or more characteristics of the virtual content, contextual data, and a user profile of the user. In some aspects, the user profile comprises historical data associated with the user. In some aspects, the contextual data comprises one or more reactions by the user to the virtual content. In some aspects, the contextual data comprises a location of the XR system.

In some aspects, the apparatus is, is part of, and/or includes a wearable device, an extended reality device (e.g., a virtual reality (VR) device, an augmented reality (AR) device, or a mixed reality (MR) device), a head-mounted display (HMD) device, a wireless communication device, a mobile device (e.g., a mobile telephone and/or mobile handset and/or so-called "smart phone" or other mobile device), a camera, a personal computer, a laptop computer, a server computer, a vehicle or a computing device or component of a vehicle, another device, or a combination thereof. In some aspects, the apparatus includes a camera or multiple cameras for capturing one or more images. In some aspects, the apparatus further includes a display for displaying one or more images, notifications, and/or other displayable data. In some aspects, the apparatuses described above can include one or more sensors (e.g., one or more inertial measurement units (IMUS), such as one or more gyroscopes, one or more gyrometers, one or more accelerometers, any combination thereof, and/or other sensor).

This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings, and each claim.

The foregoing, together with other features and embodiments, will become more apparent upon referring to the following specification, claims, and accompanying drawings.

BRIEF DESCRIPTION OF THE DRAWINGS

Illustrative embodiments of the present application are described in detail below with reference to the following drawing figures.

DETAILED DESCRIPTION

Figure 1:
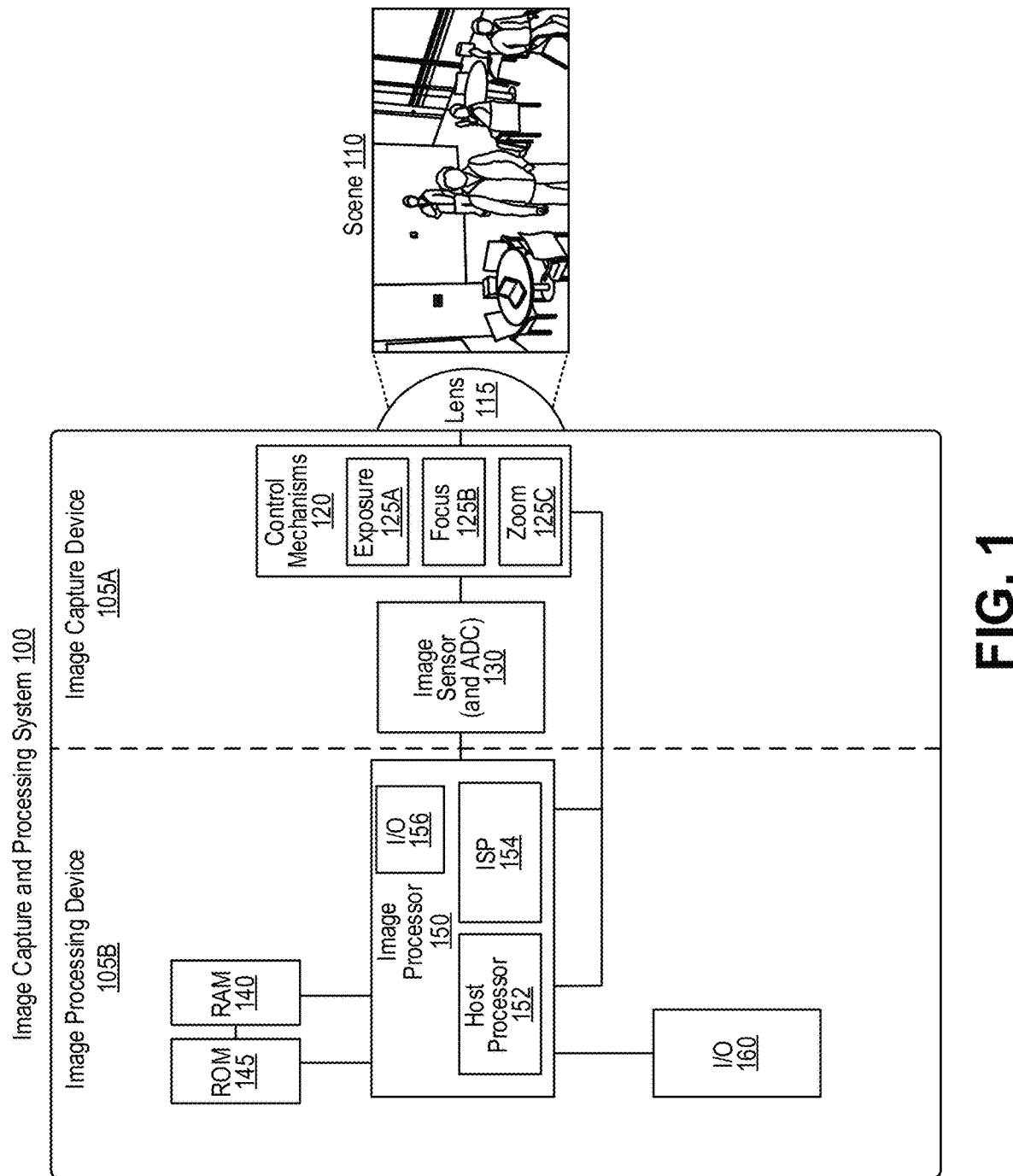
FIG. 1 is a block diagram illustrating an example architecture of an image capture and processing system, in accordance with some examples.

Certain aspects and embodiments of this disclosure are provided below. Some of these aspects and embodiments may be applied independently and some of them may be applied in combination as would be apparent to those of skill in the art. In the following description, for the purposes of explanation, specific details are set forth in order to provide a thorough understanding of embodiments of the application. However, it will be apparent that various embodiments may be practiced without these specific details. The figures and description are not intended to be restrictive.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the application as set forth in the appended claims.

A camera is a device that receives light and captures image frames, such as still images or video frames, using an image sensor. The terms "image," "image frame," and "frame" are used interchangeably herein. Cameras can be configured with a variety of image capture and image processing settings. The different settings result in images with different appearances. Some camera settings are determined and applied before or during capture of one or more image frames, such as ISO, exposure time, aperture size, f/stop, shutter speed, focus, and gain. For example, settings or parameters can be applied to an image sensor for capturing the one or more image frames. Other camera settings can configure post-processing of one or more image frames, such as alterations to contrast, brightness, saturation, sharpness, levels, curves, or colors. For example, settings or parameters can be applied to a processor (e.g., an image signal processor or ISP) for processing the one or more image frames captured by the image sensor.

Extended reality (XR) systems or devices can provide virtual content to a user and/or can combine real-world views of physical environments (scenes) and virtual environments (including virtual content). XR systems facilitate user interactions with such combined XR environments. The real-world view can include real-world objects (also referred to as physical objects), such as people, vehicles, buildings, tables, chairs, and/or other real-world or physical objects. XR systems or devices can facilitate interaction with different types of XR environments (e.g., a user can use an XR system or device to interact with an XR environment). XR systems can include virtual reality (VR) systems facilitating interactions with VR environments, augmented reality (AR) systems facilitating interactions with AR environments, mixed reality (MR) systems facilitating interactions with MR environments, and/or other XR systems. Examples of XR systems or devices include head-mounted displays (HMDs), smart glasses, among others. In some cases, an XR system can track parts of the user (e.g., a hand and/or fingertips of a user) to allow the user to interact with items of virtual content.

Systems and techniques are described herein for optimizing content understanding and real-world engagement for extended reality (XR) systems, such as augmented reality (AR) systems, virtual reality (VR) systems, and/or mixed reality (MR) systems. XR systems can include, for example, HMDs, AR glasses, heads-up displays in vehicles, mobile handsets, and other types of devices and systems.

In some cases, an XR system can include an optical "see-through" or a digital "pass-through" display (e.g., see-through or pass-through AR HMD or AR glasses), allowing the XR system to display XR content (e.g., AR content) directly onto a real-world view without displaying video content. For example, a user may view physical objects through a display (e.g., glasses or lenses), and the AR system can display AR content onto the display to provide the user with an enhanced visual perception of one or more real-world objects. In one example, a display of an optical see-through AR system can include a lens or glass in front of each eye (or a single lens or glass over both eyes). The see-through display can allow the user to see a real-world or physical object directly, and can display (e.g., projected or otherwise displayed) an enhanced image of that object or additional AR content. This allows augmenting the user's visual perception of the real world.

Optical see-through or digital pass-through XR systems can be worn while the user is engaged with the real world (as opposed to VR, in which the user is immersed in virtual content and the real world is fully occluded). Unlike smartphones, PCs, and other computing devices, head-mounted XR devices (e.g., smart glasses, HMDs, etc.) are worn on the face and thus mediate the user's visual and auditory sensory channels. Because of this, there are times when the presentation of content on a head-mounted XR device might interfere with or distract from the user's ability to effectively interact with and be aware of the user's surroundings.

XR systems and techniques for operating XR systems are described herein. In some examples, an imaging system, such as an XR system, causes virtual content to be displayed using a display according to display settings associated with the virtual content. The display settings can identify, for instance, a position, orientation, size, color, and/or layout of the virtual content as displayed on the display, and/or relative to portions of the environment viewable via the display. The environment can be viewed via the display as the virtual content is displayed by the display, for example via a see-through display or a pass-through display. The imaging system can determine, based on one or more attributes of one or both eyes of the user of the imaging system, a level of perception of the virtual content that is displayed using the display by the user, through one or both eyes of the user. The imaging system can determine the attributes based on one or more sensors focused on the user, such as one or more cameras facing one or both eyes of the user. The eye positioning attributes can identify, for instance, eye position, eye movement, pupil dilation, saccades, fixations, blinking, squinting, optokinetic reflexes or responses, vestibulo-ocular reflexes or responses, accommodation reflexes or responses, other attributes related to eyes and/or eyelids described herein, or a combination thereof. The level of perception of the virtual content can identify, for instance, whether the user has perceived the content or not, and in some instances may further identify how well the user has perceived the content. In some examples, the determination of the level of perception of the virtual content by the imaging system can include a determination of an level of comprehension of the virtual content by the user. The level of comprehension of the virtual content by the user can be based on the level of perception of the virtual content by the user, one or more characteristics of the virtual content, a user profile of the user, contextual data, or a combination thereof. The one or more characteristics of the virtual content may include a complexity of the virtual content, a uniqueness of the virtual content, distinctiveness of the virtual content relative to the environment viewable via the display, and/or the like. Th user profile of the user may include historical data associated with the user and/or current capability of the user. The imaging system can determine, based on the level of perception of the virtual content by the user and/or the level of comprehension of the virtual content, a modification to the display settings corresponding to the virtual content. The modification to the display settings, can, for example, hide, remove, shrink, reduce prominence of, reduce priority of, or terminate display of the virtual content. The modification to the display settings, can, for example, emphasize, enlarge, move, reorient, increase prominence of, and/or increase priority of, the virtual content.

The XR systems and techniques for described herein provide numerous technical advantages and benefits over traditional XR technologies and display technologies in general. For instance, XR systems and techniques described herein provide customization of XR content presentation to the user, including virtual content display to the user, based on detection of the user's actions, perception, and/or comprehension. For instance, the virtual content display to the user is customized based on analyses of the level of the user's perception and/or comprehension of the virtual content based on an analysis of the virtual content (e.g., complexity of the virtual content, the uniqueness of the virtual content, and the distinctiveness of the virtual content relative to the environment), an analysis of the user himself/herself (e.g., based on historical data such as education and profession and prior actions), and/or an analysis of context. The XR systems and techniques described herein optimize use of limited display real-estate by prioritizing certain virtual content over other virtual content and/or over a view of the environment. For example, the XR systems and techniques described herein optimize for and emphasize important virtual content, such as content warning the user of impending danger, and minimize or hide less important virtual content, such as content that the user has already seen and/or dismissed. The XR systems and techniques described herein improve safety of XR technologies by reducing distractions from virtual content at times when the user needs to focus on a vital and potentially dangerous task, such as driving, cooking, or surgery, instead emphasizing virtual content that helps the user perform the vital task. The XR systems and techniques described herein improve XR system efficiency by reducing the amount of virtual content displayed, and/or the duration for which virtual content is displayed, compared to systems that do not intelligently hide or dismiss virtual content based on the user already having perceived and/or comprehended the virtual content. These efficiency gains include reduction in bandwidth usage or data to and from the display, reduction in power usage by the display, reduction of heat generated by the display and/or the processor and/or related components, reduction in heat dissipation required for the display and/or the processor and/or related components, or a combination thereof.

Figure 2:
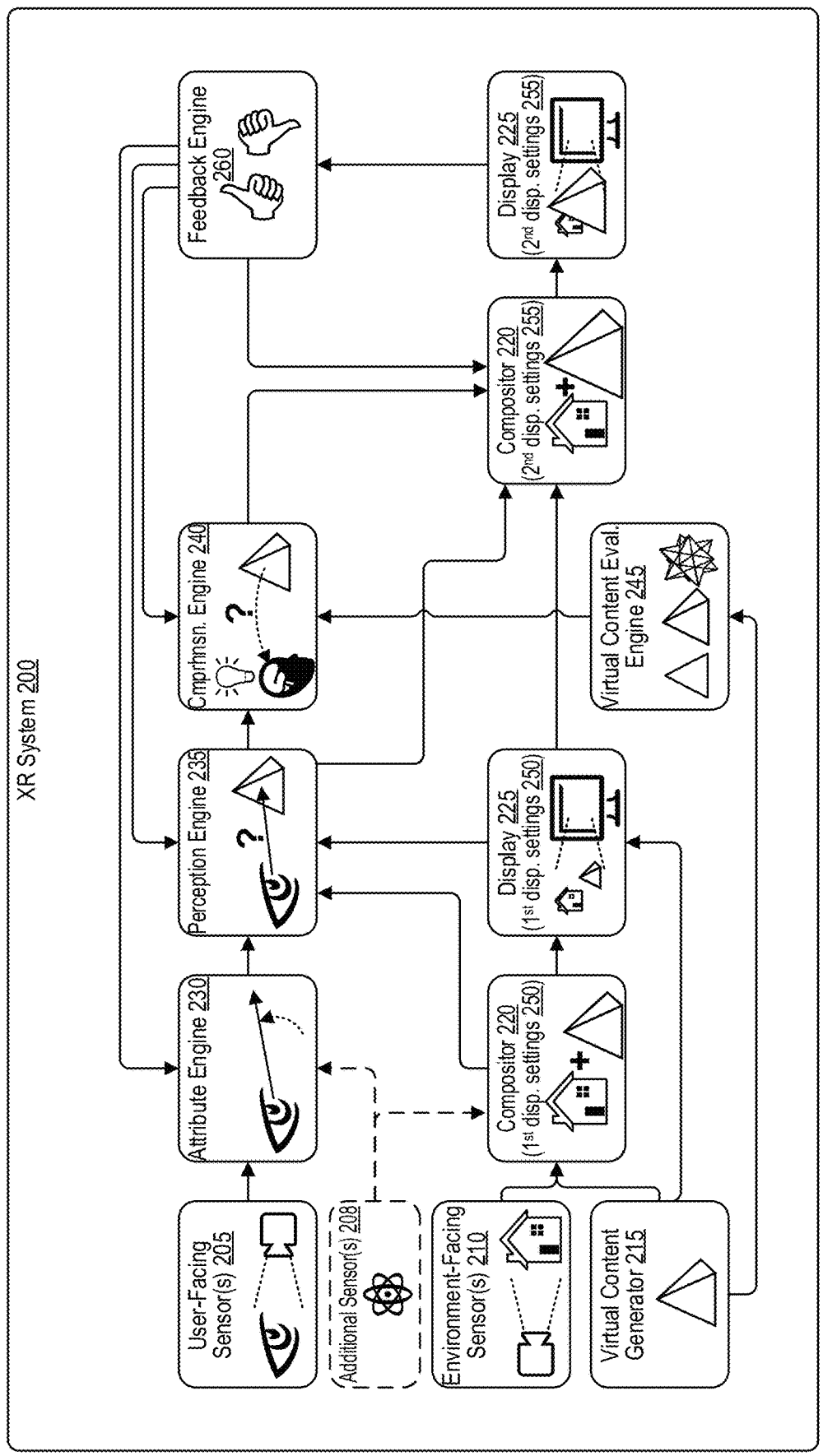
FIG. 2 is a block diagram illustrating an example architecture of an extended reality (XR) system performing a process for determining levels of perception and/or comprehension of virtual content displayed using a display by a user viewing the display, in accordance with some examples.

Various aspects of the application will be described with respect to the figures. FIG. 1 is a block diagram illustrating an architecture of an image capture and processing system 100. The image capture and processing system 100 includes various components that are used to capture and process images of one or more scenes (e.g., an image of a scene 110). The image capture and processing system 100 can capture standalone images (or photographs) and/or can capture videos that include multiple images (or video frames) in a particular sequence. A lens 115 of the system 100 faces a scene 110 and receives light from the scene 110. The lens 115 bends the light toward the image sensor 130. The light received by the lens 115 passes through an aperture controlled by one or more control mechanisms 120 and is received by an image sensor 130. In some examples, the scene 110 is a scene in an environment, such as the environment that the environment-facing sensors 210 of FIG. 2 are facing. In some examples, the scene 110 is a scene of at least a portion of a user, such as the user that the user-facing sensors 205 of FIG. 2 are facing. For instance, the scene 110 can be a scene of one or both of the user's eyes, and/or at least a portion of the user's face.

The one or more control mechanisms 120 may control exposure, focus, and/or zoom based on information from the image sensor 130 and/or based on information from the image processor 150. The one or more control mechanisms 120 may include multiple mechanisms and components; for instance, the control mechanisms 120 may include one or more exposure control mechanisms 125A, one or more focus control mechanisms 125B, and/or one or more zoom control mechanisms 125C. The one or more control mechanisms 120 may also include additional control mechanisms besides those that are illustrated, such as control mechanisms controlling analog gain, flash, HDR, depth of field, and/or other image capture properties.

The focus control mechanism 125B of the control mechanisms 120 can obtain a focus setting. In some examples, focus control mechanism 125B store the focus setting in a memory register. Based on the focus setting, the focus control mechanism 125B can adjust the position of the lens 115 relative to the position of the image sensor 130. For example, based on the focus setting, the focus control mechanism 125B can move the lens 115 closer to the image sensor 130 or farther from the image sensor 130 by actuating a motor or servo, thereby adjusting focus. In some cases, additional lenses may be included in the system 100, such as one or more microlenses over each photodiode of the image sensor 130, which each bend the light received from the lens 115 toward the corresponding photodiode before the light reaches the photodiode. The focus setting may be determined via contrast detection autofocus (CDAF), phase detection autofocus (PDAF), or some combination thereof. The focus setting may be determined using the control mechanism 120, the image sensor 130, and/or the image processor 150. The focus setting may be referred to as an image capture setting and/or an image processing setting.

The exposure control mechanism 125A of the control mechanisms 120 can obtain an exposure setting. In some cases, the exposure control mechanism 125A stores the exposure setting in a memory register. Based on this exposure setting, the exposure control mechanism 125A can control a size of the aperture (e.g., aperture size or f/stop), a duration of time for which the aperture is open (e.g., exposure time or shutter speed), a sensitivity of the image sensor 130 (e.g., ISO speed or film speed), analog gain applied by the image sensor 130, or any combination thereof. The exposure setting may be referred to as an image capture setting and/or an image processing setting.

The zoom control mechanism 125C of the control mechanisms 120 can obtain a zoom setting. In some examples, zoom control mechanism 125C stores the zoom setting in a memory register. Based on the zoom setting, the zoom control mechanism 125C can control a focal length of an assembly of lens elements (lens assembly) that includes the lens 115 and one or more additional lenses. For example, the zoom control mechanism 125C can control the focal length of the lens assembly by actuating one or more motors or servos to move one or more of the lenses relative to one another. The zoom setting may be referred to as an image capture setting and/or an image processing setting. In some examples, the lens assembly may include a parfocal zoom lens or a varifocal zoom lens. In some examples, the lens assembly may include a focusing lens (which can be lens 115 in some cases) that receives the light from the scene 110 first, with the light then passing through an afocal zoom system between the focusing lens (e.g., lens 115) and the image sensor 130 before the light reaches the image sensor 130. The afocal zoom system may, in some cases, include two positive (e.g., converging, convex) lenses of equal or similar focal length (e.g., within a threshold difference) with a negative (e.g., diverging, concave) lens between them. In some cases, the zoom control mechanism 125C moves one or more of the lenses in the afocal zoom system, such as the negative lens and one or both of the positive lenses.

The image sensor 130 includes one or more arrays of photodiodes or other photosensitive elements. Each photodiode measures an amount of light that eventually corresponds to a particular pixel in the image produced by the image sensor 130. In some cases, different photodiodes may be covered by different color filters, and may thus measure light matching the color of the filter covering the photodiode. For instance, Bayer color filters include red color filters, blue color filters, and green color filters, with each pixel of the image generated based on red light data from at least one photodiode covered in a red color filter, blue light data from at least one photodiode covered in a blue color filter, and green light data from at least one photodiode covered in a green color filter. Other types of color filters may use yellow, magenta, and/or cyan (also referred to as "emerald") color filters instead of or in addition to red, blue, and/or green color filters. Some image sensors may lack color filters altogether, and may instead use different photodiodes throughout the pixel array (in some cases vertically stacked). The different photodiodes throughout the pixel array can have different spectral sensitivity curves, therefore responding to different wavelengths of light. Monochrome image sensors may also lack color filters and therefore lack color depth.

In some cases, the image sensor 130 may alternately or additionally include opaque and/or reflective masks that block light from reaching certain photodiodes, or portions of certain photodiodes, at certain times and/or from certain angles, which may be used for phase detection autofocus (PDAF). The image sensor 130 may also include an analog gain amplifier to amplify the analog signals output by the photodiodes and/or an analog to digital converter (ADC) to convert the analog signals output of the photodiodes (and/or amplified by the analog gain amplifier) into digital signals. In some cases, certain components or functions discussed with respect to one or more of the control mechanisms 120 may be included instead or additionally in the image sensor 130. The image sensor 130 may be a charge-coupled device (CCD) sensor, an electron-multiplying CCD (EMCCD) sensor, an active-pixel sensor (APS), a complimentary metal-oxide semiconductor (CMOS), an N-type metal-oxide semiconductor (NMOS), a hybrid CCD/CMOS sensor (e.g., sCMOS), or some other combination thereof.

The image processor 150 may include one or more processors, such as one or more image signal processors (ISPs) (including ISP 154), one or more host processors (including host processor 152), and/or one or more of any other type of processor 1110 discussed with respect to the computing system 1100. The host processor 152 can be a digital signal processor (DSP) and/or other type of processor. In some implementations, the image processor 150 is a single integrated circuit or chip (e.g., referred to as a system-on-chip or SoC) that includes the host processor 152 and the ISP 154. In some cases, the chip can also include one or more input/output ports (e.g., input/output (I/O) ports 156), central processing units (CPUs), graphics processing units (GPUs), broadband modems (e.g., 3G, 4G or LTE, 5G, etc.), memory, connectivity components (e.g., Bluetooth™, Global Positioning System (GPS), etc.), any combination thereof, and/or other components. The I/O ports 156 can include any suitable input/output ports or interface according to one or more protocol or specification, such as an Inter-Integrated Circuit 2 (I2C) interface, an Inter-Integrated Circuit 3 (I3C) interface, a Serial Peripheral Interface (SPI) interface, a serial General Purpose Input/Output (GPIO) interface, a Mobile Industry Processor Interface (MIPI) (such as a MIPI CSI-2 physical (PHY) layer port or interface, an Advanced High-performance Bus (AHB) bus, any combination thereof, and/or other input/output port. In one illustrative example, the host processor 152 can communicate with the image sensor 130 using an I2C port, and the ISP 154 can communicate with the image sensor 130 using an MIPI port.

The image processor 150 may perform a number of tasks, such as de-mosaicing, color space conversion, image frame downsampling, pixel interpolation, automatic exposure (AE) control, automatic gain control (AGC), CDAF, PDAF, automatic white balance, merging of image frames to form an HDR image, image recognition, object recognition, feature recognition, receipt of inputs, managing outputs, managing memory, or some combination thereof. The image processor 150 may store image frames and/or processed images in random access memory (RAM) 140 and/or 1120, read-only memory (ROM) 145 and/or 1125, a cache, a memory unit, another storage device, or some combination thereof.

Various input/output (I/O) devices 160 may be connected to the image processor 150. The I/O devices 160 can include a display screen, a keyboard, a keypad, a touchscreen, a trackpad, a touch-sensitive surface, a printer, any other output devices 1135, any other input devices 1145, or some combination thereof. In some cases, a caption may be input into the image processing device 105B through a physical keyboard or keypad of the I/O devices 160, or through a virtual keyboard or keypad of a touchscreen of the I/O devices 160. The I/O 160 may include one or more ports, jacks, or other connectors that enable a wired connection between the system 100 and one or more peripheral devices, over which the system 100 may receive data from the one or more peripheral device and/or transmit data to the one or more peripheral devices. The I/O 160 may include one or more wireless transceivers that enable a wireless connection between the system 100 and one or more peripheral devices, over which the system 100 may receive data from the one or more peripheral device and/or transmit data to the one or more peripheral devices. The peripheral devices may include any of the previously-discussed types of I/O devices 160 and may themselves be considered I/O devices 160 once they are coupled to the ports, jacks, wireless transceivers, or other wired and/or wireless connectors.

In some cases, the image capture and processing system 100 may be a single device. In some cases, the image capture and processing system 100 may be two or more separate devices, including an image capture device 105A (e.g., a camera) and an image processing device 105B (e.g., a computing device coupled to the camera). In some implementations, the image capture device 105A and the image processing device 105B may be coupled together, for example via one or more wires, cables, or other electrical connectors, and/or wirelessly via one or more wireless transceivers. In some implementations, the image capture device 105A and the image processing device 105B may be disconnected from one another.

As shown in FIG. 1, a vertical dashed line divides the image capture and processing system 100 of FIG. 1 into two portions that represent the image capture device 105A and the image processing device 105B, respectively. The image capture device 105A includes the lens 115, control mechanisms 120, and the image sensor 130. The image processing device 105B includes the image processor 150 (including the ISP 154 and the host processor 152), the RAM 140, the ROM 145, and the I/O 160. In some cases, certain components illustrated in the image capture device 105A, such as the ISP 154 and/or the host processor 152, may be included in the image capture device 105A.

The image capture and processing system 100 can include an electronic device, such as a mobile or stationary telephone handset (e.g., smartphone, cellular telephone, or the like), a desktop computer, a laptop or notebook computer, a tablet computer, a set-top box, a television, a camera, a display device, a digital media player, a video gaming console, a video streaming device, an Internet Protocol (IP) camera, or any other suitable electronic device. In some examples, the image capture and processing system 100 can include one or more wireless transceivers for wireless communications, such as cellular network communications, 802.11 wi-fi communications, wireless local area network (WLAN) communications, or some combination thereof. In some implementations, the image capture device 105A and the image processing device 105B can be different devices. For instance, the image capture device 105A can include a camera device and the image processing device 105B can include a computing device, such as a mobile handset, a desktop computer, or other computing device.

While the image capture and processing system 100 is shown to include certain components, one of ordinary skill will appreciate that the image capture and processing system 100 can include more components than those shown in FIG. 1. The components of the image capture and processing system 100 can include software, hardware, or one or more combinations of software and hardware. For example, in some implementations, the components of the image capture and processing system 100 can include and/or can be implemented using electronic circuits or other electronic hardware, which can include one or more programmable electronic circuits (e.g., microprocessors, GPUs, DSPs, CPUs, and/or other suitable electronic circuits), and/or can include and/or be implemented using computer software, firmware, or any combination thereof, to perform the various operations described herein. The software and/or firmware can include one or more instructions stored on a computer-readable storage medium and executable by one or more processors of the electronic device implementing the image capture and processing system 100.

FIG. 2 is a block diagram illustrating an example architecture of an extended reality (XR) system 200 performing a process for determining levels of perception and/or comprehension of virtual content displayed using a display 225 by a user viewing the display 225. In some examples, the XR system 200 includes at least one image capture and processing system 100, image capture device 105A, image processing device 105B, or combination(s) thereof. In some examples, the XR system 200 includes at least one computing system 1100.

The XR system 200 includes one or more user-facing sensors 205. The user-facing sensors 205 capture sensor data measuring and/or tracking information about aspects of the user's body and/or behaviors by the user. In some examples, the user-facing sensors 205 include one or more cameras that face at least a portion of the user. The one or more cameras can include one or more image sensors that capture images of at least a portion of the user. For instance, the user-facing sensors 205 can include one or more cameras focused on one or both eyes (and/or eyelids) of the user, with the image sensors of the cameras capturing images of one or both eyes of the user. The one or more cameras may also be referred to as eye capturing sensor(s). In some implementations, the one or more cameras can capture series of images over time, which in some examples may be sequenced together in temporal order, for instance into videos. These series of images can depict or otherwise indicate, for instance, movements of the user's eye(s), pupil dilations, blinking (using the eyelids), squinting (using the eyelids), saccades, fixations, eye moisture levels, optokinetic reflexes or responses, vestibulo-ocular reflexes or responses, accommodation reflexes or responses, other attributes related to eyes and/or eyelids described herein, or a combination thereof. Within FIG. 2, the one or more user-facing sensors 205 are illustrated as a camera facing an eye of the user and capturing images of the eye of the user. The user-facing sensors 205 can include one or more sensors that track information about the user's body and/or behaviors, such as cameras, mage sensors, microphones, heart rate monitors, oximeters, biometric sensors, positioning receivers, Global Navigation Satellite System (GNSS) receivers, Inertial Measurement Units (IMUs), accelerometers, gyroscopes, gyrometers, barometers, thermometers, altimeters, depth sensors, light detection and ranging (LIDAR) sensors, radio detection and ranging (RADAR) sensors, sound detection and ranging (SODAR) sensors, sound navigation and ranging (SONAR) sensors, time of flight (ToF) sensors, structured light sensors, other sensors discussed herein, or combinations thereof. In some examples, the one or more user-facing sensors 205 include at least one image capture and processing system 100, image capture device 105A, image processing device 105B, or combination(s) thereof. In some examples, the one or more user-facing sensors 205 include at least one input device 1145 of the computing system 1100, or are themselves an input device 1145 of the computing system 1100.

The XR system 200 includes a virtual content generator 215 that generates virtual content. The virtual content can include two-dimensional (2D) shapes, three-dimensional (3D) shapes, 2D objects, 3D objects, 2D models, 3D models, 2D animations, 3D animations, 2D images, 3D images, textures, portions of other images, alphanumeric characters, strings of alphanumeric characters, or combinations thereof. Within FIG. 2, the virtual content generated by the virtual content generator 215 is illustrated as a tetrahedron. Examples of virtual content that includes strings of alphanumeric characters include the virtual content 525, the virtual content 530, the virtual content 535, the virtual content 630, and the virtual content 730. In some examples, the virtual content generator 215 includes a software element, such as a set of instructions corresponding to a program, that is run on a processor such as the processor 1110 of the computing system 1100, the image processor 150, the host processor 152, the ISP 154, or a combination thereof. In some examples, the virtual content generator 215 includes one or more hardware elements. For instance, the virtual content generator 215 can include a processor such as the processor 1110 of the computing system 1100, the image processor 150, the host processor 152, the ISP 154, or a combination thereof. In some examples, the virtual content generator 215 includes a combination of one or more software elements and one or more hardware elements.

The XR system 200 includes a display 225 that displays the virtual content at least partially overlaid over a view of an environment. The view of the environment may include a view of the real-world environment around the XR system 200. The view of the environment may include a view of a virtual environment and/or mixed environment that is at least partially based on the real-world environment and that is at least partially virtual. In some examples, the display 225 can include an output device 1135. In some examples, the output device 1135 can include the display 225.

In some examples, the display 225 of the XR system 200 is a optical "see-through" display that allows light from the real-world environment (scene) around the XR system 200 to traverse (e.g., pass) through the display 225 to reach one or both eyes of the user. For example, the display 225 can be at least partially transparent, translucent, light-transmissive, or a combination thereof. In an illustrative example, the display 225 includes a transparent, translucent, and/or light-transmissive lens and a projector. The projector projects the virtual content onto the lens. The lens may be, for example, a lens of a pair of glasses, a lens of a goggle, a contact lens, a lens of a head-mounted display (HMD) device, or a combination thereof. Light from the real-world environment passes through the lens and reaches one or both eyes of the user. Because the projector projects the virtual content onto the lens, the virtual content appears to be overlaid over the user's view of the environment from the perspective of one or both of the user's eyes. The positioning of the virtual content as projected onto the lens by the projector can be identified and/or indicated by display settings (e.g., first display settings 250, second display settings 255). The compositor 220 can determine and/or modify the display settings.

In some examples, the display 225 of the XR system 200 includes a projector without the lens discussed above with respect to the optical see-through display. Instead, the display 225 can use its projector to project the virtual content onto one or both eyes of the user. In some examples, the projector of the display 225 can project the virtual content onto one or both retinas of one or both eyes of the user. Such a display 225 can be referred to as an optical see-through display, a virtual retinal display (VRD), a retinal scan display (RSD), or a retinal projector (RP). Light from the real-world environment (scene) still reaches one or both eyes of the user. Because the projector projects the virtual content onto one or both eyes of the user, the virtual content appears to be overlaid over the user's view of the environment from the perspective of one or both of the user's eyes. The positioning of the virtual content as projected onto one or both eyes of the user by the projector can be identified and/or indicated by display settings (e.g., first display settings 250, second display settings 255). The compositor 220 can determine and/or modify the display settings.

In some examples, the display 225 of the XR system 200 is a digital "pass-through" display that allows the user to see a view of an environment by displaying the view of the environment on the display 225. The view of the environment that is displayed on the digital pass-through display can be a view of the real-world environment around the XR system 200, for example based on (image) sensor data captured by one or more environment-facing sensors 210 of the XR system 200. The view of the environment that is displayed on the pass-through display can be a view of a virtual environment or a mixed environment that is distinct from the real-world environment but that is based on the real-world environment. For instance, the virtual environment or a mixed environment can include virtual objects and/or backgrounds, but that may be mapped to areas and/or volumes of space with dimensions that are based on dimensions of areas and/or volumes of space within the real-world environment that the user and the XR system 200 are in. The XR system 200 can determine the dimensions of areas and/or volumes of space within the real-world environment that the user and the XR system 200 are in. In some implementations, the XR system may include one or more environment-facing sensors 210 of the XR system 200 capturing images of the environment (e.g., surroundings of the XR system) and/or depth data of the environment. This can ensure that, while the user explores the virtual environment or mixed environment displayed on the display 225, the user does not accidentally fall down a set of stairs, run into a wall or obstacle, or otherwise have a negative interaction and/or potentially dangerous interaction with the real-world environment.

The XR system 200, in examples where the display 225 is a digital pass-through display, can use the compositor 220 to overlay the virtual content generated by the virtual content generator 215 over at least a portion of the environment displayed on the display 225. In some examples, the compositor 220 can overlay the virtual content fully over the environment displayed on the display 225, so that the virtual content appears, from the perspective of one or both eyes of the user viewing the display 225, to be fully in front of the rest of the environment that is displayed on the display 225. In some examples, the compositor 220 can overlay at least a portion of the virtual content over portions of the environment displayed on the display 225, so that the virtual content appears, from the perspective of one or both eyes of the user viewing the display 225, to be in front some portions of the environment that is displayed on the display 225, but behind other portions of the environment that is displayed on the display 225. The compositor 220 can thus provide a simulated depth to the virtual content, overlaying portions of the environment that are displayed on the display 225 over portions of the virtual content. An example of this simulated depth is illustrated in FIG. 5B, where the head of the statue of Red Auerbach is partially overlaid over part of the virtual content 530 according to the display settings 555.

The XR system 200, in an example where the display 225 is an optical see-through display, can use the compositor 220 to spare a portion of the real-world environment from becoming overlaid by the virtual content generated by the virtual content generator 215. In some examples, the compositor 220 can overlay the virtual content only partially over the real-world environment on the display, so that the virtual content appears, from the perspective of one or both eyes of the user viewing the display 225, to be behind at least a portion of the real-world environment. In some examples, the compositor 220 can overlay the virtual content only partially over the real-world environment on the display, so that the virtual content appears, from the perspective of one or both eyes of the user viewing the display 225, to be behind at least a portion of the real-world environment and in front of other portions of the real-world environment. The compositor 220 can thus provide a simulated depth to the virtual content, sparing portions of the real-world environment from being overlaid by virtual content. The positioning of the virtual content relative to the environment can be identified and/or indicated by display settings (e.g., first display settings 250, second display settings 255). The compositor 220 can determine and/or modify the display settings.

The one or more environment-facing sensors 210 of the XR system 200 are one or more sensors that are pointed, directed, and/or focused away from the user and/or on a portion of the real-world environment. For example, the one or more environment-facing sensors 210 can be pointed, directed, and/or face in a direction that the user, and/or a front side of the XR system 200, is facing. The environment-facing sensors 210 capture sensor data measuring and/or tracking information about the real-world environment. In some examples, the environment-facing sensors 210 include one or more cameras that face at least a portion of the real-world environment. The one or more cameras can include one or more image sensors that capture images of at least a portion of the real-world environment. For instance, the environment-facing sensors 210 can include one or more cameras focused on the real-world environment (e.g., on a surrounding of the XR system 200), with the image sensors of the cameras capturing images of the real-world environment (e.g., of the surrounding). Such cameras can capture series of images over time, which in some examples may be sequenced together in temporal order, for instance into videos. These series of images can depict or otherwise indicate, for instance, floors, ground, walls, ceilings, sky, water, plants, other people other than the user, portions of the user's body (e.g., arms or legs), structures, vehicles, animals, devices, other objects, or combinations thereof. Within FIG. 2, the one or more environment-facing sensors 210 are illustrated as a camera facing a house (an example of a structure). In some examples, the one or more environment-facing sensors 210 include at least one image capture and processing system 100, image capture device 105A, image processing device 105B, or combination(s) thereof. In some examples, the one or more environment-facing sensors 210 include at least one input device 1145 of the computing system 1100, or are themselves an input device 1145 of the computing system 1100.

The environment-focused sensors 210 can include cameras, image sensors, positioning receivers, Global Navigation Satellite System (GNSS) receivers, Inertial Measurement Units (IMUs), accelerometers, gyroscopes, gyrometers, barometers, thermometers, altimeters, depth sensors, light detection and ranging (LIDAR) sensors, radio detection and ranging (RADAR) sensors, sound detection and ranging (SODAR) sensors, sound navigation and ranging (SONAR) sensors, time of flight (ToF) sensors, structured light sensors, other sensors discussed herein, or combinations thereof.

In some examples, the XR system 200 can also include one or more additional sensors 208 such as cameras, image sensors, positioning receivers, Global Navigation Satellite System (GNSS) receivers, Inertial Measurement Units (IMUs), accelerometers, gyroscopes, gyrometers, barometers, thermometers, altimeters, depth sensors, light detection and ranging (LIDAR) sensors, radio detection and ranging (RADAR) sensors, sound detection and ranging (SODAR) sensors, sound navigation and ranging (SONAR) sensors, time of flight (ToF) sensors, structured light sensors, other sensors discussed herein, or combinations thereof. In some implementations, the additional sensor(s) 208 may complement or refine sensor readings from the user-facing sensor(s) 205 and/or the environment-facing sensor(s) 210. For example, Inertial Measurement Units (IMUs), accelerometers, gyroscopes, or other sensors be used by attribute engine 230 to refine the determination of a user perception of a virtual content (e.g., by detecting the head shake or head nod by the user). In another example, depth sensors, light detection and ranging (LIDAR) sensors, radio detection and ranging (RADAR) sensors, sound detection and ranging (SODAR) sensors, sound navigation and ranging (SONAR) sensors, time of flight (ToF) sensors may be used by compositor 220 to identify portions (e.g., identifiable objects) of the real-world environment which are to be spared from being overlaid by the display when creating a simulated depth of the virtual content.

The XR system 200 includes a compositor 220. The compositor 220 composes, composites, and/or combines a view of the virtual content in (within) the environment that the user views through the display 225. The compositor 220 of the XR system 200 can determine a first set of display settings for the display 225 (e.g., first display settings 250). The compositor 220 of the XR system 200 can modify the first set of display settings for the display 225 to generate a second set of display settings for the display 225 (e.g., second display settings 255). In an XR system 200 in which the display 225 is a digital "pass-through" display, the compositor 220 can generate an image that composes, composites, and/or combines a view of the environment (e.g., based on sensor data from the environment-facing sensors 210) with the virtual content generated by the virtual content generator 215. The display settings generated by the compositor 220 can indicate the position, orientation, depth, size, color, font size, font color, text language, layout, and/or other properties of the virtual content, and/or of specific elements or portions of the virtual content. In an XR system 200 in which the display 225 is an optical "see-through" display, the compositor 220 can generate display settings indicating a position, orientation, depth, size, color, font size, font color, text language, and/or other properties of the virtual content, and/or of specific elements or portions of the virtual content, as displayed by the display 225 (e.g., as projected onto the lens by the projector of the display 225). In an XR system 200 in which the display 225 is a virtual retinal display (VRD), the compositor 220 can generate display settings indicating a position, orientation, depth, size, color, font size, font color, text language, and/or other properties of the virtual content, and/or of specific elements or portions of the virtual content, as displayed by the display 225 (e.g., as projected onto one or both eyes of the user by the projector of the display 225). Within FIG. 2, the compositor 220 (on the left-hand side of the XR system 200) is illustrated as adding the virtual content (represented by the tetrahedron) to the view of the environment (represented by the house). Within FIG. 2, the display 225 (on the left-hand side of the XR system 200) is illustrated as a display displaying and/or providing a view of both the virtual content (represented by the tetrahedron) and the view of the environment (represented by the house). In some examples, the compositor 220 includes a software element, such as a set of instructions corresponding to a program, that is run on a processor such as the processor 1110 of the computing system 1100, the image processor 150, the host processor 152, the ISP 154, or a combination thereof. In some examples, the compositor 220 includes one or more hardware elements. For instance, the compositor 220 can include a processor such as the processor 1110 of the computing system 1100, the image processor 150, the host processor 152, the ISP 154, or a combination thereof. In some examples, the compositor 220 includes a combination of one or more software elements and one or more hardware elements.

The XR system 200 includes an attribute engine 230 that determines one or more perception-related attributes based on the sensor data from the user-facing sensors 205. The perception-related attributes of the user can include one or more attributes of one or more eyes of the user, one or more attributes of facial expressions of the user, one or more gestures of the user, or a combination of the above. For example, the attributes of the user can include position(s) of one or both eyes of the user at specific times, movements by one or both eyes of the user, saccade eye positions for one or both eyes of the user, saccade eye movements for one or both eyes of the user, saccade times for one or both eyes of the user, saccade frequency for one or both eyes of the user, saccade duration for one or both eyes of the user, fixation eye positions for one or both eyes of the user, fixation eye movements for one or both eyes of the user, fixation times for one or both eyes of the user, fixation frequency for one or both eyes of the user, fixation duration for one or both eyes of the user, blink eye and/or eyelid positions for one or both eyes and/or eyelids of the user, blink eye and/or eyelid movements for one or both eyes and/or eyelids of the user, blink times for one or both eyes and/or eyelids of the user, blink frequency for one or both eyes and/or eyelids of the user, blink duration for one or both eyes and/or eyelids of the user, squint eye and/or eyelid positions for one or both eyes and/or eyelids of the user, squint eye and/or eyelid movements for one or both eyes and/or eyelids of the user, squint times for one or both eyes and/or eyelids of the user, squint frequency for one or both eyes and/or eyelids of the user, squint duration for one or both eyes and/or eyelids of the user, squint extent or level for one or both eyes and/or eyelids of the user, dwell eye positions for one or both eyes of the user, dwell times for one or both eyes of the user, dwell frequency for one or both eyes of the user, dwell duration for one or both eyes of the user, dwell extent or level for one or both eyes of the user, pupil dilation eye positions for one or both eyes of the user, pupil dilation eye movements for one or both eyes of the user, pupil dilation times for one or both eyes of the user, pupil dilation frequency for one or both eyes of the user, pupil dilation duration for one or both eyes of the user, pupil dilation extent or level for one or both eyes of the user, eye lens shape (e.g., associated with accommodation using ciliary muscle(s)) for one or both eyes of the user, changes to eye lens shape (e.g., associated with accommodation using ciliary muscle(s)) for one or both eyes of the user, times of changes to eye lens shape for one or both eyes of the user, frequency of changes to eye lens shape for one or both eyes of the user, extent of changes to eye lens shape for one or both eyes of the user, head tilt times for the head of the user, head tilt frequency for the head of the user, head tilt duration for the head of the user, head tilt extent or level for the head of the user, head tilt times for the head of the user, head tilt frequency for the head of the user, head tilt duration for the head of the user, head tilt extent or level for the head of the user, eye positions for one or both eyes of the user during a head tilt by the user, eye movements for one or both eyes of the user during a head tilt by the user, head shake times for the head of the user, head shake frequency for the head of the user, head shake duration for the head of the user, head shake extent or level for the head of the user, head shake times for the head of the user, head shake frequency for the head of the user, head shake duration for the head of the user, head shake extent or level for the head of the user, eye positions for one or both eyes of the user during a head shake by the user, eye movements for one or both eyes of the user during a head shake by the user, head nod times for the head of the user, head nod frequency for the head of the user, head nod duration for the head of the user, head nod extent or level for the head of the user, head nod times for the head of the user, head nod frequency for the head of the user, head nod duration for the head of the user, head nod extent or level for the head of the user, eye positions for one or both eyes of the user during a head nod by the user, eye movements for one or both eyes of the user during a head nod by the user, smile times by the user, smile frequency by the user, smile duration by the user, smile extent or level by the user, smile times by the user, smile frequency by the user, smile duration by the user, smile extent or level by the user, eye positions for one or both eyes of the user during a smile by the user, eye movements for one or both eyes of the user during a smile by the user, laugh times by the user, laugh frequency by the user, laugh duration by the user, laugh extent or level by the user, laugh times by the user, laugh frequency by the user, laugh duration by the user, laugh extent or level by the user, eye positions for one or both eyes of the user during a laugh by the user, eye movements for one or both eyes of the user during a laugh by the user, frown times by the user, frown frequency by the user, frown duration by the user, frown extent or level by the user, frown times by the user, frown frequency by the user, frown duration by the user, frown extent or level by the user, eye positions for one or both eyes of the user during a frown by the user, eye movements for one or both eyes of the user during a frown by the user, crying times by the user, crying frequency by the user, crying duration by the user, crying extent or level by the user, crying times by the user, crying frequency by the user, crying duration by the user, crying extent or level by the user, eye positions for one or both eyes of the user during a cry by the user, eye movements for one or both eyes of the user during a cry by the user, eye moisture level for one or both eyes of the user, eye dryness level for one or both eyes of the user, optokinetic reflex or response eye positions for one or both eyes of the user, optokinetic reflex or response eye movements for one or both eyes of the user, optokinetic reflex or response times for one or both eyes of the user, optokinetic reflex or response frequency for one or both eyes of the user, optokinetic reflex or response duration for one or both eyes of the user, vestibulo-ocular reflex or response eye positions for one or both eyes of the user, vestibulo-ocular reflex or response eye movements for one or both eyes of the user, vestibulo-ocular reflex or response times for one or both eyes of the user, vestibulo-ocular reflex or response frequency for one or both eyes of the user, vestibulo-ocular reflex or response duration for one or both eyes of the user, other attributes related to eyes and/or eyelids described herein, accommodation reflex or response eye positions for one or both eyes of the user, accommodation reflex or response eye movements for one or both eyes of the user, accommodation reflex or response times for one or both eyes of the user, accommodation reflex or response frequency for one or both eyes of the user, accommodation reflex or response duration for one or both eyes of the user, or a combination thereof.

Within FIG. 2, the attribute engine 230 is illustrated as identifying a movement (represented by a dotted lined arrow) of a gaze direction (represented by a solid black lined arrow) of an eye of the user. In some examples, the attribute engine 230 includes a software element, such as a set of instructions corresponding to a program, that is run on a processor such as the processor 1110 of the computing system 1100, the image processor 150, the host processor 152, the ISP 154, or a combination thereof. In some examples, the attribute engine 230 includes one or more hardware elements. For instance, the attribute engine 230 can include a processor such as the processor 1110 of the computing system 1100, the image processor 150, the host processor 152, the ISP 154, or a combination thereof. In some examples, the attribute engine 230 includes a combination of one or more software elements and one or more hardware elements. In some examples, the attribute engine 230 includes, and/or executes, one or more artificial intelligence (AI) algorithms and/or machine learning (ML) systems. The one or more AI algorithms and/or ML systems can receive sensor data from the user-facing sensors 205 as inputs, and can output the attributes. Examples of one or more ML systems of the attribute engine 230 include first trained ML model 825 and/or the neural network 900.

The XR system 200 includes a perception engine 235 that determines and/or estimates an level of perception of the virtual content by the user (e.g., using one or both eyes of the user). The perception engine 235 determines and/or estimates the level of user perception of the virtual content based on the perception-related attributes that the attribute engine 230 identifies, and/or directly based on the sensor data from the user-focused sensors 205. The perception engine 235 determines and/or estimates the level of user perception of the virtual content based on the display settings for the virtual content as generated by the compositor 220 (e.g., the display settings 250). The perception engine 235 can use the display settings (e.g., the display settings 250) to identify where the virtual content is displayed along the display 225. The perception engine 235 can use the perception-related attributes that the attribute engine 230 identifies, to determine where one or both eyes of the user are looking, how one or both eyes of the user are moving, an extent to which one or both eyes of the user are squinting while looking, an extent to which one or both eyes of the user are blinking, an extent to which one or both eyes of the user are fixating, an extent to which one or both eyes of the user are performing saccades, an extent to which the user is smiling, an extent to which the user is laughing, an extent to which the user is frowning, an extent to which the user is crying, or combinations thereof. The perception engine 235 can determine whether the user has looked at and/or near the virtual content, how long the user has looked at and/or near the virtual content, how closely aligned the user's gaze and the position of the virtual content are, and the like. The perception engine 235 may interpret squinting and/or fixations, for example, as indicative of the user focusing on the virtual content and/or on another piece of content displayed on the display 225. The perception engine 235 may interpret blinking and/or saccades, for example, as indicative of the user potentially missing (e.g., not perceiving) the virtual content and/or on another piece of content displayed on the display 225. The level of perception of the virtual content by the user, as output by the perception engine 235, can be a value that indicates no perception at all of the virtual content by the user, for instance if the user has had his or her eyes closed, and/or has been looking very far away from the position of the virtual content, while the virtual content has been displayed on the display 225. The level of perception of the virtual content by the user, as output by the perception engine 235, can be a value that indicates very high perception of the virtual content by the user, for instance if the user has been staring at the position where the virtual content is displayed for a long period of time. The level of perception of the virtual content by the user, as output by the perception engine 235, can be a value between that indicates a level of perception higher than the no perception example above and lower than the high perception example above. The level of perception of the virtual content, as determined and output by the perception engine 235, can be referred to as an extent of perception of the virtual content and/or a metric of perception of the virtual content.

Within FIG. 2, the perception engine 235 is illustrated as identifying whether a gaze direction of an eye of the user (represented by a solid black lined arrow) matches a position of the virtual content (represented by a tetrahedron). In some examples, the perception engine 235 includes a software element, such as a set of instructions corresponding to a program, that is run on a processor such as the processor 1110 of the computing system 1100, the image processor 150, the host processor 152, the ISP 154, or a combination thereof. In some examples, the perception engine 235 includes one or more hardware elements. For instance, the perception engine 235 can include a processor such as the processor 1110 of the computing system 1100, the image processor 150, the host processor 152, the ISP 154, or a combination thereof. In some examples, the perception engine 235 includes a combination of one or more software elements and one or more hardware elements. In some examples, the perception engine 235 includes, and/or executes, one or more AI algorithms and/or MLs systems. The one or more AI algorithms and/or ML systems can receive the one or more perception-related attributes generated by the attribute engine 230 (and/or the sensor data captured by the user-facing sensors 205) as inputs, and can output a level of perception of the virtual content by the user. Examples of one or more ML systems of the perception engine 235 include second trained ML model 835 and/or the neural network 900.

The XR system 200 includes a comprehension engine 240 that determines and/or estimates a level of comprehension and/or understanding of the virtual content by the user. The comprehension engine 240 determines and/or estimates the level of comprehension and/or understanding of the virtual content by the user based on the level of perception of the virtual content by the user as determined by the perception engine 235. In some examples, the comprehension engine 240 determines and/or estimates the level of comprehension and/or understanding of the virtual content by the user based on an analysis of the virtual content by a virtual content evaluation engine 245. In some examples, the comprehension engine 240 determines and/or estimates the level of comprehension and/or understanding of the virtual content by the user based on historical data associated with the user.

In some examples, the XR system 200 includes the virtual content evaluation engine 245. The virtual content evaluation engine 245 generates an analysis of the virtual content. In some examples, the virtual content evaluation engine 245 generates the analysis of the virtual content based on complexity of the virtual content, uniqueness of the virtual content, or a combination thereof. In some examples, the virtual content evaluation engine determines a metric based on uniqueness. Uniqueness may be a measure of how often (e.g., how times and/or how frequently) the virtual content has been displayed (e.g., previously) on the display 225, if at all. If the virtual content includes a message or object that is displayed very frequently on the display 225, the virtual content may determine that the virtual content has a low uniqueness. If the virtual content includes a message or object that has never been displayed on the display 225 before, the virtual content evaluation engine 245 may determine that the virtual content has a high uniqueness. If the virtual content includes a message or object that has been displayed on the display 225 infrequently (e.g., once or twice before), the virtual content evaluation engine 245 may determine that the virtual content has a medium uniqueness. The uniqueness may fall within a range of possible values (e.g., low, medium, high, and one or more values in between any two of these). In some examples, the uniqueness may be referred to as a uniqueness score, a uniqueness level, a uniqueness metric, or a uniqueness extent.

In some examples, the virtual content includes a string of alphanumeric characters (e.g., a string of text). The virtual content evaluation engine 245 can evaluate the complexity of the virtual content based at least in part on the length of the string, with longer string having a higher complexity than shorter strings. The virtual content evaluation engine 245 can generate a complexity metric for the virtual content based at least in part on a number of steps included in a set of instructions in the virtual content. For instance, the virtual content evaluation engine 245 can provide a higher complexity metric for virtual content that includes instructions with more steps, and a lower complexity metric for virtual content that includes instructions with fewer steps. The virtual content evaluation engine 245 can analyze the complexity of the virtual content based at least in part on the complexity of words included in the string as determined by the virtual content evaluation engine 245. For instance, the virtual content evaluation engine 245 can assign a higher complexity to sophisticated technical terms (e.g., "semiconductor," "exhaust manifold gasket," "anti-siphon valve") than to more common everyday words (e.g., "today," "stop," "continue"). The virtual content evaluation engine 245 can assign or provide a higher complexity to strings that include more complex words than to strings that include fewer complex words, and/or more words that are not complex and/or less complex (e.g., words that are common and/or simple). The virtual content evaluation engine 245 can analyze the complexity of the virtual content based at least in part on the complexity, as determined by the virtual content evaluation engine 245, of any equations or formulas included in the string. For instance, the virtual content evaluation engine 245 can assign a higher complexity to equations or formulas that include more variables, and/or that corresponds to a higher difficulty level of mathematics, than to equations or formulas that include fewer variables, and/or corresponds to a lower difficulty level of mathematics. The virtual content evaluation engine 245 can assign a higher complexity to strings that include more complex equations or formulas than to strings that include fewer complex equations or formulas, and/or more equations or formulas that as less complex. The complexity may fall within a range of possible values (e.g., low, medium, high, and one or more values in between any two of these). In some examples, the complexity may be referred to as a complexity score, a complexity level, a complexity metric, or a complexity extent.

The virtual content evaluation engine 245 can generate a complexity metric for the virtual content based at least in part on an estimated amount of prior knowledge required to understand or comprehend the subject matter described in the virtual content. For example, the virtual content evaluation engine 245 can assign a higher complexity to virtual content that includes subject matter that is associated with a high level of prior knowledge, and a lower complexity to virtual content that includes subject matter that requires a lower level of prior knowledge. High and low levels of prior knowledge can be associated, for example, with which courses the subject matter might typically be taught and/or learned in. For instance, subject matter that requires a lower level of prior knowledge might be subject matter that is typically taught and/or learned in $3^{rd}$ grade (elementary school), while subject matter that requires a higher level of prior knowledge might be subject matter that is typically taught and/or learned in graduate school (e.g., in a specific graduate course, for which another graduate course and numerous undergraduate courses are prerequisites). For instance, virtual content describing differential equations or Banach spaces requires a higher level of prior knowledge than virtual content describing the Pythagorean theorem. The virtual content evaluation engine 245 can determine the subject matter of the virtual content based on the words included in the virtual content. The virtual content evaluation engine 245 can compare the subject matter to a look-up table that identifies a corresponding level of prior knowledge associated with the subject matter.

The virtual content evaluation engine 245 can generate a complexity metric for the virtual content based at least in part on the complexity of one or more shapes, objects, images, and/or textures of the virtual content. For instance, the virtual content evaluation engine 245 can assign a higher complexity to virtual content including more complex polygons and/or polyhedrons than to virtual content including less complex polygons and/or polyhedrons. Within FIG. 2, the virtual content evaluation engine 245 is illustrated as identifying complexity from low complexity (represented by a triangle) to medium complexity (represented by a tetrahedron) to high complexity (represented by a stellated dodecahedron).

In some cases, to evaluate the virtual content, the virtual content evaluation engine 245 can determine a complexity metric and a uniqueness metric for the virtual content. The virtual content evaluation engine 245 can convert the complexity metric and the uniqueness metric into a single metric for the virtual content. The single metric is a fused metric based on the complexity metric and the uniqueness metric, which can be the product, sum, or average of the complexity metric and the uniqueness metric. In one illustrative example, the virtual content can include a notification of "Warning: Hot Stove!", in which case the virtual content evaluation engine 245 can assign a complexity metric with value of 1 and a uniqueness metric with value of 2. The virtual content evaluation engine 245 can determine the single metric with value as $1 \times 2 = 2$. In another illustrative example, the virtual content can include a notification of "Add salt and stir the roux until mixture is bubbly and foaming", in which case the virtual content evaluation engine 245 can determine a complexity metric with value of 3 and a uniqueness metric with value of 5. The virtual content evaluation engine 245 can determine the single metric with value as $3 \times 5 = 15$.

Historical data associated with the user can include a level of education of the user, such as some high school, high school alumnus, some university, university alumnus, some graduate school, graduate school alumnus, some post-graduate school, post-graduate alumnus, and the like. Historical data associated with the user can include a specialization in the education of the user, such as a major, a minor, a research area, a class subject, a school or program (e.g., school of engineering, school of life sciences), and the like. Historical data associated with the user can include a job, career, trade, and/or profession of the user. Historical data associated with the user can include a transaction history of the user, a browsing history of the user, a gameplay history of the user, a virtual content viewing history of the user, a location history of the user, a residence history of the user, and the like. Historical data associated with the user can include an age of the user, a time of day (e.g., which may indicate if the user is tired), a history of the user's comprehension or understanding of previously-presented virtual content, a history of the user's feedback (e.g., via feedback engine 260) on previously-presented virtual content, a history of the user's successful completion of actions that are requested by or suggested by previously-presented virtual content, and the like.

The comprehension engine 240 determines and/or estimates the level of comprehension and/or understanding of the virtual content by the user based on the level of perception of the virtual content by the user as determined by the perception engine 235, an analysis of the virtual content by the virtual content evaluation engine 245, the historical data associated with the user, or a combination thereof. For example, if the perception engine 235 indicates that the user looked at the virtual content for 10 seconds, the virtual content has received low uniqueness and low complexity evaluations from the virtual content evaluation engine 245, and the virtual content is concerns a subject that the user is very familiar with based on the user's historical data, then the comprehension engine 240 can determine and/or estimate that the user has comprehended and/or understood the virtual content to a high level of comprehension and/or understanding. On the other hand, if the perception engine 235 indicates that the user looked at the virtual content for 5 seconds, the virtual content has received high uniqueness and high complexity evaluations from the virtual content evaluation engine 245, and the virtual content does not concerns a subject that the user is familiar with based on the user's historical data, then the comprehension engine 240 can determine and/or estimate that the user has comprehended and/or understood the virtual content to a low level of comprehension and/or understanding. The level of comprehension and/or understanding of the virtual content, as determined and output by the comprehension engine 240, can be referred to as an extent of comprehension and/or understanding of the virtual content and/or as a metric of comprehension and/or understanding of the virtual content.

Different combinations of level of perception, evaluations from the virtual content evaluation engine 245, and historical data associated with the user may result in the comprehension engine 240 determining and/or estimating different levels of comprehension and/or understanding of the virtual content by the user. For instance, if the virtual content concerns a subject that the user is very familiar with based on the user's historical data, then the comprehension engine 240 can determine and/or estimate that the user has comprehended and/or understood the virtual content to a reasonably high level of comprehension and/or understanding even if the virtual content has received high uniqueness and high complexity evaluations from the virtual content evaluation engine 245, and/or if the perception engine 235 indicates that the user looked at the virtual content for a relatively short time. If the perception engine 235 indicates that the user looked at the virtual content for a long time, then the comprehension engine 240 can determine and/or estimate that the user has comprehended and/or understood the virtual content to a reasonably high level of comprehension and/or understanding even if the virtual content has received high uniqueness and high complexity evaluations from the virtual content evaluation engine 245, and/or if the virtual content does not concern a subject that the user is familiar with based on the user's historical data. If the perception engine 235 indicates that the virtual content evaluation engine 245 has evaluated the virtual content as having low uniqueness and/or low complexity, then the comprehension engine 240 can determine and/or estimate that the user has comprehended and/or understood the virtual content to a reasonably high level of comprehension and/or understanding even if the perception engine 235 indicates that the user looked at the virtual content for a relatively short time, and/or if the virtual content does not concern a subject that the user is familiar with based on the user's historical data.

In some examples, the comprehension engine 240 can determines and/or estimates the level of comprehension and/or understanding of the virtual content by the user based on perception-related attributes determined by the attribute engine 230. For example, the comprehension engine 240 can increase its determination and/or estimation of the level of comprehension and/or understanding of the virtual content if the perception-related attributes determined by the attribute engine 230 indicate that the user appears to be reacting to the virtual content, for instance by smiling, laughing, frowning, crying, nodding, shaking their head, tilting their head, or saying something related to the virtual content. In some examples, the comprehension engine 240 can decrease its determination and/or estimation of the level of comprehension and/or understanding of the virtual content if the perception-related attributes determined by the attribute engine 230 indicate that the user appears to be reacting to the virtual content negatively, for example by frowning or crying or shaking their head (e.g., in a "no" motion) or verbally expressing a negative emotion, as these may indicate that the user is upset or frustrated due to the user's inability to understand the virtual content to a high level.

In some examples, the comprehension engine 240 can determines and/or estimates the level of comprehension and/or understanding of the virtual content by the user based on contextual data. Contextual data can include, for example, reactions by the user to the virtual content. In some examples, the comprehension engine 240 can increase its determination and/or estimation of the level of comprehension and/or understanding of the virtual content by the user based on identification that the user has performed an action that the virtual content requests that the user perform, or suggests that the user perform. For instance, if the virtual content requests that the user pick up an object, and the XR system 200 determines (e.g., based on sensor data from the user-facing sensors 205 and/or the environment-facing sensors 210) that the user has picked up the object, then the comprehension engine 240 can determine and/or estimate that the user has comprehended and/or understood the virtual content to a high level of comprehension and/or understanding. In some examples, the comprehension engine 240 can decrease its determination and/or estimation of the level of comprehension and/or understanding of the virtual content by the user based on identification that the user has performed an action that is contrary to what the virtual content requests or suggests that the user do. For instance, if the virtual content provides driving directions requesting that the user turn onto a specific street, and the XR system 200 determines (e.g., based on sensor data from the user-facing sensors 205 and/or the environment-facing sensors 210) that the user has not turned on that street, then the comprehension engine 240 can determine and/or estimate that the user has comprehended and/or understood the virtual content to a low level of comprehension and/or understanding.

Contextual data can include, for example, the location of the user and/or other objects detected in the environment, location of the XR system 200, status of the XR system 200 (e.g., low battery or high battery), time of day, user input(s) received through a user interface of the XR system 200, previous virtual content displayed by the XR system, resolution of the display 225, traveling speed of the user and/or XR system 200, whether the environment around the XR system 200 is static or dynamic, environment obstacle detection, environment noise level, a second person is speaking to the user, or some combination thereof. In some examples, the comprehension engine 240 can provide a higher determination and/or estimation of the level of comprehension and/or understanding of the virtual content by the user if the user is walking rather than driving, since the user may have more distractions from the virtual content when driving than while walking. The XR system 200 may delay display of the virtual content until after the user stops driving in some cases, to improve safety. In some examples, the comprehension engine 240 can provide a higher determination and/or estimation of the level of comprehension and/or understanding of the virtual content by the user if the environmental noise level around the user and/or XR system 200 is lower than if the environmental noise level is higher, since a lower environmental noise level suggests fewer distractions from the virtual content for the user than a higher environmental noise level. In some examples, the comprehension engine 240 can provide a lower determination and/or estimation of the level of comprehension and/or understanding of the virtual content by the user if a second person is speaking to the user than if there is no second person speaking to the user, since the second person speaking to the user distract the user from the virtual content. In some examples, the comprehension engine 240 can provide a higher determination and/or estimation of the level of comprehension and/or understanding of the virtual content by the user if the user and/or XR system 200 are moving at a slower speed rather than a faster speed, since the user may have more distractions from the virtual content when moving at a faster speed than while moving at a slower speed. The XR system 200 may delay display of the virtual content until after the user slows down to a slower speed, to improve safety in case the user is driving or otherwise operating a vehicle. In some examples, the comprehension engine 240 can provide a higher determination and/or estimation of the level of comprehension and/or understanding of the virtual content by the user during afternoon than early morning or late evening, since the user is likely to be less tired during the afternoon than during early morning or late evening.

The level of comprehension or understanding of the virtual content by the user, as output by the comprehension engine 240, can be a value that indicates no comprehension or understanding at all of the virtual content by the user, for instance if the user has had his or her eyes closed, and/or has been looking very far away from the position of the virtual content, while the virtual content has been displayed on the display 225. The level of comprehension or understanding of the virtual content by the user, as output by the comprehension engine 240, can be a value that indicates very high perception of the virtual content by the user, for instance if the user has been staring at the position where the virtual content is displayed for a long period of time, the virtual content has a low complexity, the virtual content has a low uniqueness, and the historical data associated with the user indicates that the user is very familiar with a subject that the virtual data concerns. The level of perception of the virtual content by the user, as output by the comprehension engine 240, can be a value between that indicates a level of perception higher than the no comprehension or understanding example above, and lower than the high comprehension or understanding example above.

Within FIG. 2, the comprehension engine 240 is illustrated as identifying whether the user comprehends or understands the virtual content, represented by a dotted-lined arrow from the virtual content (represented by a tetrahedron) to the user's mind. In some examples, the comprehension engine 240 includes a software element, such as a set of instructions corresponding to a program, that is run on a processor such as the processor 1110 of the computing system 1100, the image processor 150, the host processor 152, the ISP 154, or a combination thereof. In some examples, the comprehension engine 240 includes one or more hardware elements. For instance, the comprehension engine 240 can include a processor such as the processor 1110 of the computing system 1100, the image processor 150, the host processor 152, the ISP 154, or a combination thereof. In some examples, the comprehension engine 240 includes a combination of one or more software elements and one or more hardware elements. In some examples, the comprehension engine 240 includes, and/or executes, one or more AI algorithms and/or MLs systems. The one or more AI algorithms and/or ML systems can receive the one or more perception-related attributes generated by the attribute engine 230 (and/or the sensor data captured by the user-focused sensors 205) as inputs, and can output a level of perception of the virtual content. Examples of one or more ML systems of the comprehension engine 240 include third trained ML model 865 and/or the neural network 900.

The compositor 220 and the display 225 are both illustrated twice in the XR system 200 of FIG. 2—once on the left side of the XR system 200, and once on the right side of the XR system 200. It should be understood that these two instances of the compositor 220 and the display 225 can represent the same compositor 220 and/or the same display 225, but at different times. For instance, the compositor 220 and display 225 illustrated on the left side of the XR system 200 represent the compositor 220 generating the first display settings 250, and the display 225 displaying the virtual content overlaid over the view of the environment based on the first display settings 250. The compositor 220 and display 225 illustrated on the right side of the XR system 200 represent the compositor 220 generating the second display settings 255 at least in part by modifying the first display settings 250, and the display 225 displaying the virtual content overlaid over the view of the environment based on the second display settings 255.

The compositor 220 can perform the modification of the first display settings 250 to generate the second display settings 255 based on one or more factors. These factors can include, for example, the level of perception of the virtual content by the user as determined by the perception engine 235, the level of comprehension and/or understanding of the virtual content by the user as determined by the comprehension engine 240, the perception-related attributes of the user determined by the attribute engine 230, historical data about the user, contextual data, sensor data from the user-facing sensors 205, sensor data from the environment-facing sensors 210, or combinations thereof. The modification of the first display settings 250 by the compositor 220 to generate the second display settings 255 can change aspects of the virtual content. For instance, the modification can change the position, orientation, depth, size, color, font size, font color, text language, and/or other properties of the virtual content, and/or of specific elements or portions of the virtual content. In some examples, the modification can delete, remove, hide, and/or terminate display of the virtual content on the display 225. In some cases, the modification can add additional virtual content for display on the display 225. In an illustrative example, if the perception engine 235 indicates that the user has perceived a piece of virtual content to a high level, and/or the comprehension engine 240 indicates that the user has comprehended the piece of virtual content to a high level, then the compositor 220 can shrink the piece of virtual content as displayed on the display 225 or even terminate display of the virtual content on the display 225. On the other hand, if the perception engine 235 indicates that the user has perceived a piece of virtual content to a low level, and/or the comprehension engine 240 indicates that the user has comprehended the piece of virtual content to a low level, but that the perception-related attributes from the attribute engine 230 indicate that the user is trying to perceive and/or comprehend the virtual content, then the compositor 220 can increase the size the piece of virtual content, and/or increase the font size of the alphanumeric string(s) of the virtual content, as displayed on the display 225, and can shrink and/or terminate display of other virtual content on the display 225 to reduce distractions for the user.

Within FIG. 2, the compositor 220 on the left-hand side of the XR system 200 is illustrated as adding the virtual content (represented by the tetrahedron) to the view of the environment (represented by the house) according to the first display settings 250, in which the virtual content (represented by the tetrahedron) is small. Within FIG. 2, the display 225 on the left-hand side of the XR system 200 is illustrated as a display displaying and/or providing a view of both the virtual content (represented by the tetrahedron) and the view of the environment (represented by the house) according to the first display settings 250, in which the virtual content (represented by the tetrahedron) is small. Within FIG. 2, the compositor 220 on the right-hand side of the XR system 200 is illustrated as adding the virtual content (represented by the tetrahedron) to the view of the environment (represented by the house) according to the second display settings 255, in which the virtual content (represented by the tetrahedron) is large. Within FIG. 2, the display 225 on the right-hand side of the XR system 200 is illustrated as a display displaying and/or providing a view of both the virtual content (represented by the tetrahedron) and the view of the environment (represented by the house) according to the second display settings 255, in which the virtual content (represented by the tetrahedron) is large.

In some examples, the XR system 200 includes a feedback engine 260. The feedback engine 260 can detect feedback received from the user interface. The feedback can be feedback regarding the virtual content, the modification by the compositor 220 from the first display settings 250 to the second display settings 255, and/or determinations by the XR system 200 that the modification by the compositor 220 from the first display settings 250 to the second display settings 255 are based on. The determinations by the XR system 200 can include, for instance, the level of perception of the virtual content by the user as determined by the perception engine 235, the level of comprehension and/or understanding of the virtual content by the user as determined by the comprehension engine 240, the perception-related attributes determined by the attribute engine 230, historical data about the user, contextual data, sensor data from the user-facing sensors 205, sensor data from the environment-facing sensors 210, or combinations thereof. The feedback received by the feedback engine 260 can be positive feedback or negative feedback. For instance, if the virtual content requests or suggests that the user perform a specific action (e.g., turn right), and the user performs the action, the feedback engine 260 can interpret this performance of the action by the user as positive feedback. Positive feedback can also be based on perception-related attributes, such as the user smiling, laughing, nodding, saying a positive statement (e.g., "yes," "confirmed," "okay," "next"), or otherwise positively reacting to the virtual content. On the other hand, if the virtual content requests or suggests that the user perform a specific action (e.g., turn right on XYZ street), and the user does not perform the action or performs a different action (e.g., the user turns left on XYZ street), the feedback engine 260 can interpret this non-performance of the action by the user, or this performance of a different action by the user, as negative feedback. Negative feedback can also be based on perception-related attributes, such as the user frowning, crying, shaking their head (e.g., in a "no" motion), saying a negative statement (e.g., "no," "negative," "bad," "not this"), or otherwise negatively reacting to the virtual content.

In some examples, the feedback engine 260 provides the feedback to one or more ML systems of the XR system 200 to update the one or more ML systems of the XR system 200. The feedback engine 260 can provide, as training data to the one or more ML systems of the XR system 200, the feedback, the virtual content that triggered the feedback, the display settings that triggered the feedback, the modification to the display settings that triggered the feedback, the level of perception of the virtual content by the user as determined by the perception engine 235, the level of comprehension and/or understanding of the virtual content by the user as determined by the comprehension engine 240, the perception-related attributes determined by the attribute engine 230 corresponding to the feedback, historical data about the user corresponding to the feedback, contextual data corresponding to the feedback, sensor data from the user-facing sensors 205 corresponding to the feedback, sensor data from the environment-facing sensors 210 corresponding to the feedback, or combinations thereof. For instance, the feedback engine 260 can provides such training data to one or more ML systems of the attribute engine 230 (e.g., the first trained ML model 825), to one or more ML systems of the perception engine 235 (e.g., the second trained ML model 835), to one or more ML systems of the comprehension engine 240 (e.g., the third trained ML model 865), or a combination thereof.

In some examples, the feedback engine 260 includes a software element, such as a set of instructions corresponding to a program, that is run on a processor such as the processor 1110 of the computing system 1100, the image processor 150, the host processor 152, the ISP 154, or a combination thereof. In some examples, the feedback engine 260 includes one or more hardware elements. For instance, the feedback engine 260 can include a processor such as the processor 1110 of the computing system 1100, the image processor 150, the host processor 152, the ISP 154, or a combination thereof. In some examples, the feedback engine 260 includes a combination of one or more software elements and one or more hardware elements.

Over time, the system can learn and optimize the time that a message should remain in place for a user. The system will determine a likelihood that the message will be read/viewed in a certain amount of time, for example, by developing a confidence level for a message. If a high degree of likelihood is determined, the eye tracking cameras might not need to be used.

Figure 3A:
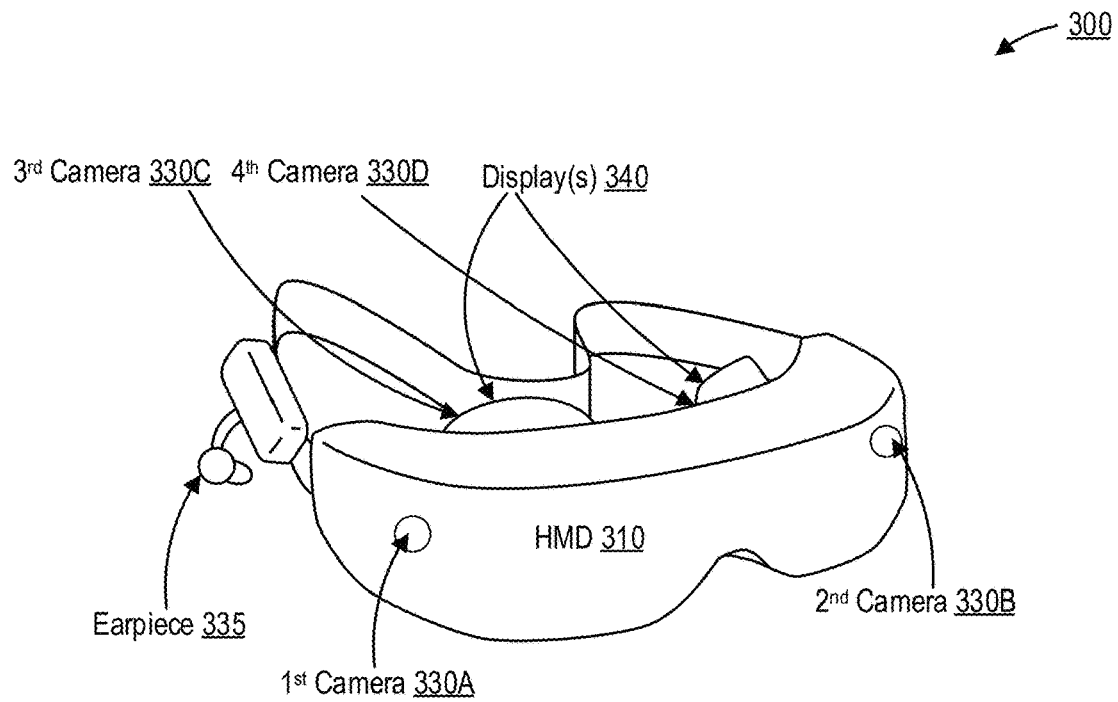
FIG. 3A is a perspective diagram illustrating a head-mounted display (HMD) that is used as an extended reality (XR) system, in accordance with some examples.

FIG. 3A is a perspective diagram 300 illustrating a head-mounted display (HMD) 310 that is used as an extended reality (XR) system 200. The HMD 310 may be, for example, an augmented reality (AR) headset, a virtual reality (VR) headset, a mixed reality (MR) headset, an extended reality (XR) headset, or some combination thereof. The HMD 310 may be an example of an XR system 200. The HMD 310 includes a first camera 330A and a second camera 330B along a front portion of the HMD 310. The first camera 330A and the second camera 330B may be examples of the environment-facing sensors 210 of the XR system 200. The HMD 310 includes a third camera 330C and a fourth camera 330D facing the eye(s) of the user as the eye(s) of the user face the display(s) 340. The third camera 330C and the fourth camera 330D may be examples of the user-facing sensors 205 of the XR system 200. In some examples, the HMD 310 may only have a single camera with a single image sensor. In some examples, the HMD 310 may include one or more additional cameras in addition to the first camera 330A, the second camera 330B, third camera 330C, and the fourth camera 330D. In some examples, the HMD 310 may include one or more additional sensors in addition to the first camera 330A, the second camera 330B, third camera 330C, and the fourth camera 330D, which may also include other types of user-facing sensors 205 and/or environment-facing sensors 210 of the XR system 200. In some examples, the first camera 330A, the second camera 330B, third camera 330C, and/or the fourth camera 330D may be examples of the image capture and processing system 100, the image capture device 105A, the image processing device 105B, or a combination thereof.

The HMD 310 may include one or more displays 340 that are visible to a user 320 wearing the HMD 310 on the user 320's head. The one or more displays 340 of the HMD 310 can be examples of the one or more displays 225 of the XR system 200. In some examples, the HMD 310 may include one display 340 and two viewfinders. The two viewfinders can include a left viewfinder for the user 320's left eye and a right viewfinder for the user 320's right eye. The left viewfinder can be oriented so that the left eye of the user 320 sees a left side of the display. The right viewfinder can be oriented so that the left eye of the user 320 sees a right side of the display. In some examples, the HMD 310 may include two displays 340, including a left display that displays content to the user 320's left eye and a right display that displays content to a user 320's right eye. The one or more displays 340 of the HMD 310 can be digital "pass-through" displays or optical "see-through" displays.

Figure 3B:
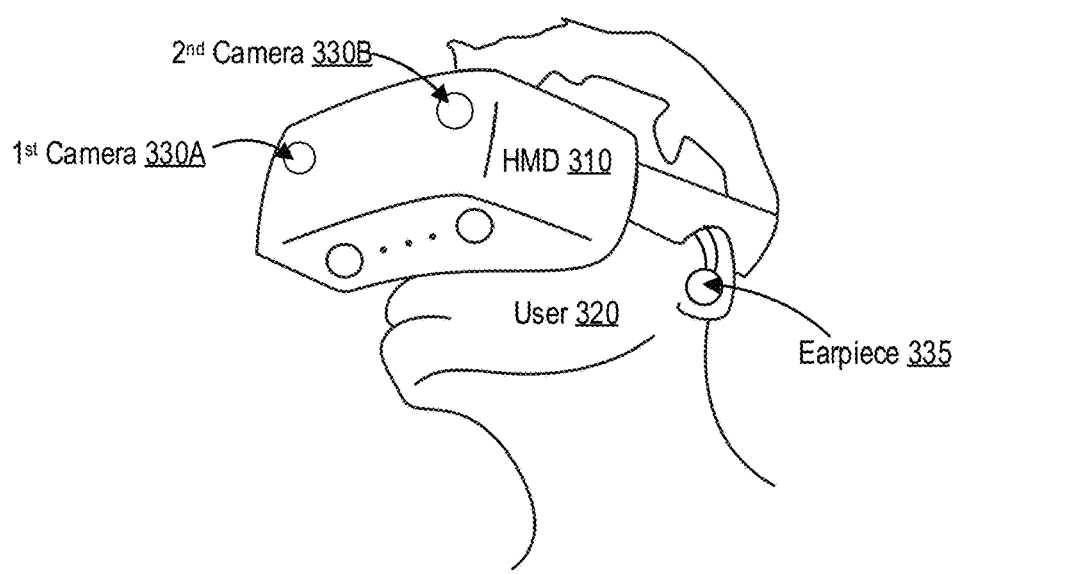
FIG. 3B is a perspective diagram illustrating the head-mounted display (HMD) of FIG. 3A being worn by a user, in accordance with some examples.

The HMD 310 may include one or more earpieces 335, which may function as speakers and/or headphones that output audio to one or more ears of a user of the HMD 310. One earpiece 335 is illustrated in FIGS. 3A and 3B, but it should be understood that the HMD 310 can include two earpieces, with one earpiece for each ear (left ear and right ear) of the user. In some examples, the HMD 310 can also include one or more microphones (not pictured). The one or more microphones can be examples of the user-facing sensors 205 and/or environment-facing sensors 210 of the XR system 200. In some examples, the audio output by the HMD 310 to the user through the one or more earpieces 335 may include, or be based on, audio recorded using the one or more microphones.

FIG. 3B is a perspective diagram 350 illustrating the head-mounted display (HMD) of FIG. 3A being worn by a user 320. The user 320 wears the HMD 310 on the user 320's head over the user 320's eyes. The HMD 310 can capture images with the first camera 330A and the second camera 330B. In some examples, the HMD 310 displays one or more output images toward the user 320's eyes using the display(s) 340. In some examples, the output images can include the virtual content generated by the virtual content generator 215, composited using the compositor 220, and/or displayed by the display 225 according to the display settings (e.g., first display settings 250, second display settings 255). The output images can be based on the images captured by the first camera 330A and the second camera 330B, for example with the virtual content overlaid. The output images may provide a stereoscopic view of the environment, in some cases with the virtual content overlaid and/or with other modifications. For example, the HMD 310 can display a first display image to the user 320's right eye, the first display image based on an image captured by the first camera 330A. The HMD 310 can display a second display image to the user 320's left eye, the second display image based on an image captured by the second camera 330B. For instance, the HMD 310 may provide overlaid virtual content in the display images overlaid over the images captured by the first camera 330A and the second camera 330B. The third camera 330C and the fourth camera 330D can capture images of the eyes of the before, during, and/or after the user views the display images displayed by the display(s) 340. This way, the sensor data from the third camera 330C and/or the fourth camera 330D can capture reactions to the virtual content by the user's eyes (and/or other portions of the user). An earpiece 335 of the HMD 310 is illustrated in an ear of the user 320. The HMD 310 may be outputting audio to the user 320 through the earpiece 335 and/or through another earpiece (not pictured) of the HMD 310 that is in the other ear (not pictured) of the user 320.

Figure 4A:
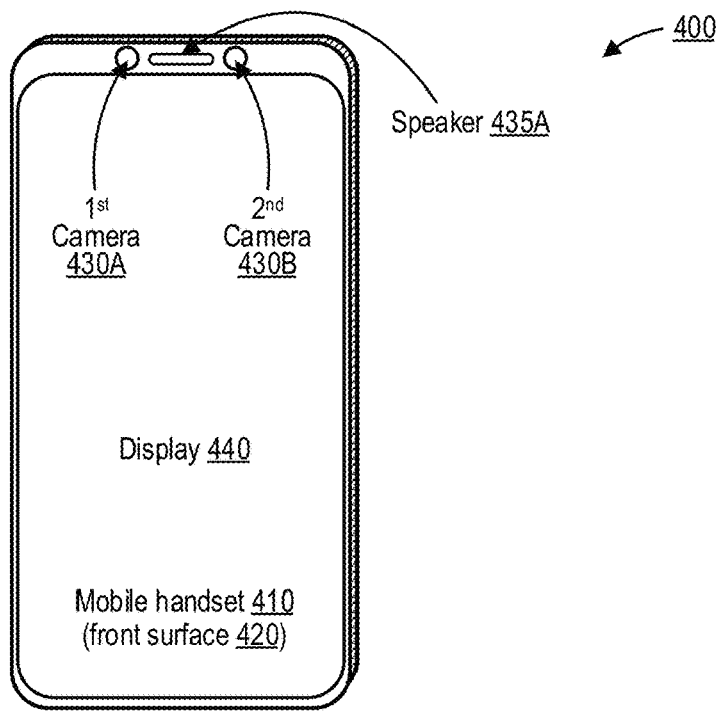
FIG. 4A is a perspective diagram illustrating a front surface of a mobile handset that includes front-facing cameras and that can be used as an extended reality (XR) system, in accordance with some examples.

FIG. 4A is a perspective diagram 400 illustrating a front surface of a mobile handset 410 that includes front-facing cameras and can be used as an extended reality (XR) system 200. The mobile handset 410 may be an example of a XR system 200. The mobile handset 410 may be, for example, a cellular telephone, a satellite phone, a portable gaming console, a music player, a health tracking device, a wearable device, a wireless communication device, a laptop, a mobile device, any other type of computing device or computing system discussed herein, or a combination thereof.

The front surface 420 of the mobile handset 410 includes a display 440. The front surface 420 of the mobile handset 410 includes a first camera 430A and a second camera 430B. The first camera 430A and the second camera 430B may be examples of the user-facing sensors 205 of the XR system 200. The first camera 430A and the second camera 430B can face the user, including the eye(s) of the user, while content (e.g., the virtual content overlaid over the environment) is displayed on the display 440. The display 440 may be an example of the display 225 of the XR system 200.

The first camera 430A and the second camera 430B are illustrated in a bezel around the display 440 on the front surface 420 of the mobile handset 410. In some examples, the first camera 430A and the second camera 430B can be positioned in a notch or cutout that is cut out from the display 440 on the front surface 420 of the mobile handset 410. In some examples, the first camera 430A and the second camera 430B can be under-display cameras that are positioned between the display 440 and the rest of the mobile handset 410, so that light passes through a portion of the display 440 before reaching the first camera 430A and the second camera 430B. The first camera 430A and the second camera 430B of the perspective diagram 400 are front-facing cameras. The first camera 430A and the second camera 430B face a direction perpendicular to a planar surface of the front surface 420 of the mobile handset 410. The first camera 430A and the second camera 430B may be two of the one or more cameras of the mobile handset 410. The first camera 430A and the second camera 430B may be the sensor 405A and the sensor 405B, respectively. In some examples, the front surface 420 of the mobile handset 410 may only have a single camera.

In some examples, the front surface 420 of the mobile handset 410 may include one or more additional cameras in addition to the first camera 430A and the second camera 430B. The one or more additional cameras may also be examples of the user-facing sensors 205 of the XR system 200. In some examples, the front surface 420 of the mobile handset 410 may include one or more additional sensors in addition to the first camera 430A and the second camera 430B. The one or more additional sensors may also be examples of the user-facing sensors 205 of the XR system 200. In some cases, the front surface 420 of the mobile handset 410 includes more than one display 440. The one or more displays 440 of the front surface 420 of the mobile handset 410 can be examples of the display(s) 225 of the XR system 200. For example, the one or more displays 440 can include one or more touchscreen displays.

The mobile handset 410 may include one or more speakers 435A and/or other audio output devices (e.g., earphones or headphones or connectors thereto), which can output audio to one or more ears of a user of the mobile handset 410. One speaker 435A is illustrated in FIG. 4A, but it should be understood that the mobile handset 410 can include more than one speaker and/or other audio device. In some examples, the mobile handset 410 can also include one or more microphones (not pictured). The one or more microphones can be examples of the user-facing sensors 205 and/or of the environment-facing sensors 210 of the XR system 200. In some examples, the mobile handset 410 can include one or more microphones along and/or adjacent to the front surface 420 of the mobile handset 410, with these microphones being examples of the user-facing sensors 205 of the XR system 200. In some examples, the audio output by the mobile handset 410 to the user through the one or more speakers 435A and/or other audio output devices may include, or be based on, audio recorded using the one or more microphones.

Figure 4B:
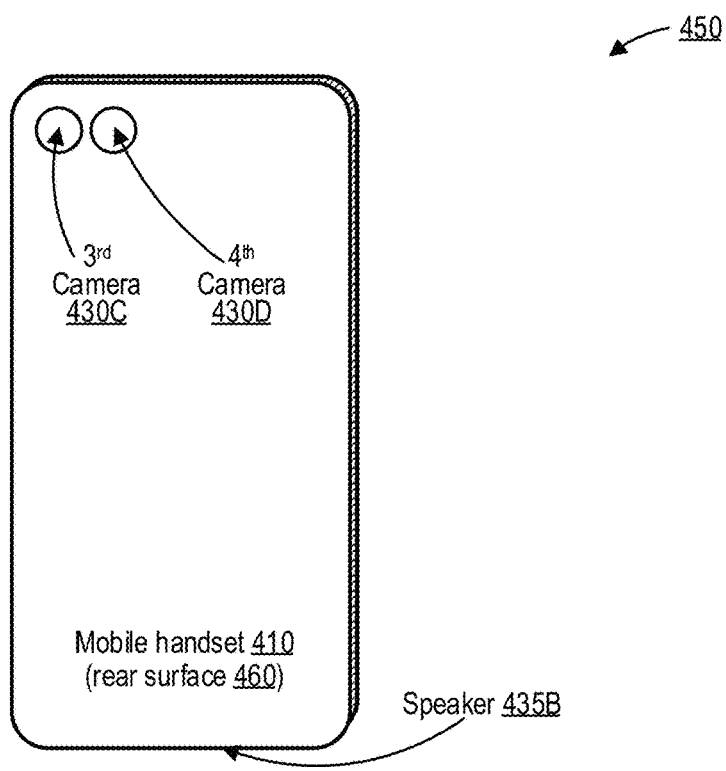
FIG. 4B is a perspective diagram illustrating a rear surface of a mobile handset that includes rear-facing cameras and that can be used as an extended reality (XR) system, in accordance with some examples.

FIG. 4B is a perspective diagram 450 illustrating a rear surface 460 of a mobile handset that includes rear-facing cameras and that can be used as an extended reality (XR) system 200. The mobile handset 410 includes a third camera 430C and a fourth camera 430D on the rear surface 460 of the mobile handset 410. The third camera 430C and the fourth camera 430D of the perspective diagram 450 are rear-facing. The third camera 430C and the fourth camera 430D may be examples of the environment-facing sensors 210 of the XR system 200 of FIG. 2. The third camera 430C and the fourth camera 430D face a direction perpendicular to a planar surface of the rear surface 460 of the mobile handset 410.

The third camera 430C and the fourth camera 430D may be two of the one or more cameras of the mobile handset 410. In some examples, the rear surface 460 of the mobile handset 410 may only have a single camera. In some examples, the rear surface 460 of the mobile handset 410 may include one or more additional cameras in addition to the third camera 430C and the fourth camera 430D. The one or more additional cameras may also be examples of the environment-facing sensors 210 of the XR system 200. In some examples, the rear surface 460 of the mobile handset 410 may include one or more additional sensors in addition to the third camera 430C and the fourth camera 430D. The one or more additional sensors may also be examples of the environment-facing sensors 210 of the XR system 200. In some examples, the first camera 430A, the second camera 430B, third camera 430C, and/or the fourth camera 430D may be examples of the image capture and processing system 100, the image capture device 105A, the image processing device 105B, or a combination thereof.

The mobile handset 410 may include one or more speakers 435B and/or other audio output devices (e.g., earphones or headphones or connectors thereto), which can output audio to one or more ears of a user of the mobile handset 410. One speaker 435B is illustrated in FIG. 4B, but it should be understood that the mobile handset 410 can include more than one speaker and/or other audio device. In some examples, the mobile handset 410 can also include one or more microphones (not pictured). The one or more microphones can be examples of the user-facing sensors 205 and/or of the environment-facing sensors 210 of the XR system 200. In some examples, the mobile handset 410 can include one or more microphones along and/or adjacent to the rear surface 460 of the mobile handset 410, with these microphones being examples of the environment-facing sensors 210 of the XR system 200. In some examples, the audio output by the mobile handset 410 to the user through the one or more speakers 435B and/or other audio output devices may include, or be based on, audio recorded using the one or more microphones.

The mobile handset 410 may use the display 440 on the front surface 420 as a pass-through display. For instance, the display 440 may display output images. The output images can be based on the images captured by the third camera 430C and/or the fourth camera 430D, for example with the virtual content overlaid. The first camera 430A and/or the second camera 430B can capture images of the user's eyes (and/or other portions of the user) before, during, and/or after the display of the output images with the virtual content on the display 440. This way, the sensor data from the first camera 430A and/or the second camera 430B can capture reactions to the virtual content by the user's eyes (and/or other portions of the user).

Figure 5A:
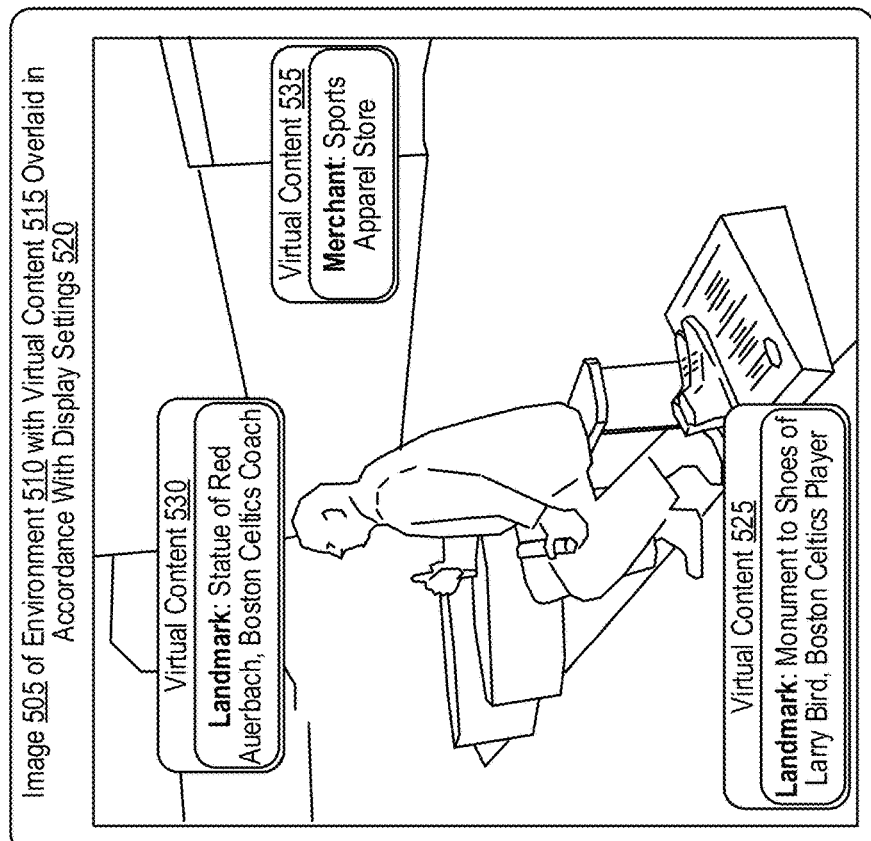
FIG. 5A is a conceptual diagram illustrating an image of an environment in Boston before and after overlay of virtual content as displayed in accordance with display settings, in accordance with some examples.
Figure 5A:
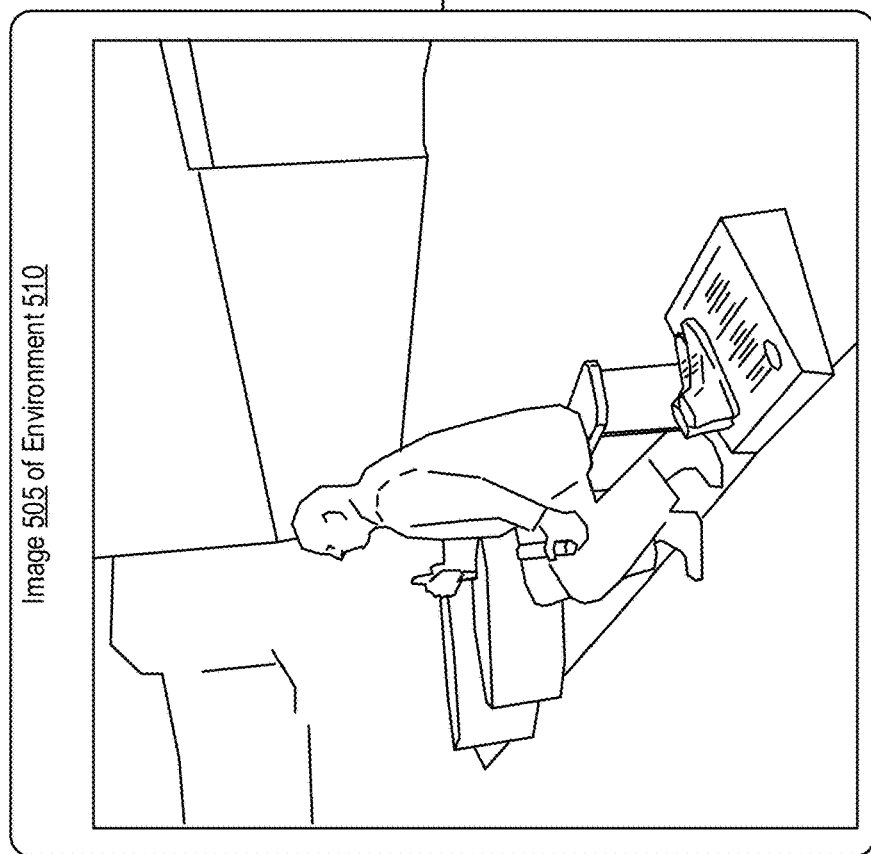
Figure 5B:
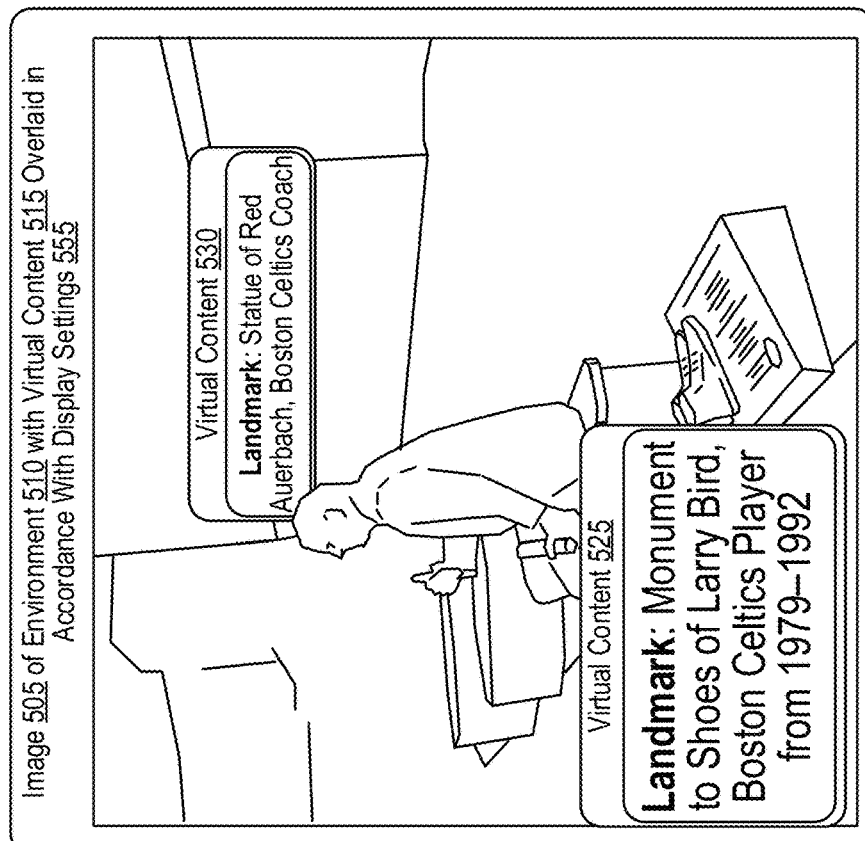
FIG. 5B is a conceptual diagram illustrating the image of the environment in Boston with the virtual content overlaid before and after a modification to the display settings, in accordance with some examples.
Figure 5B:
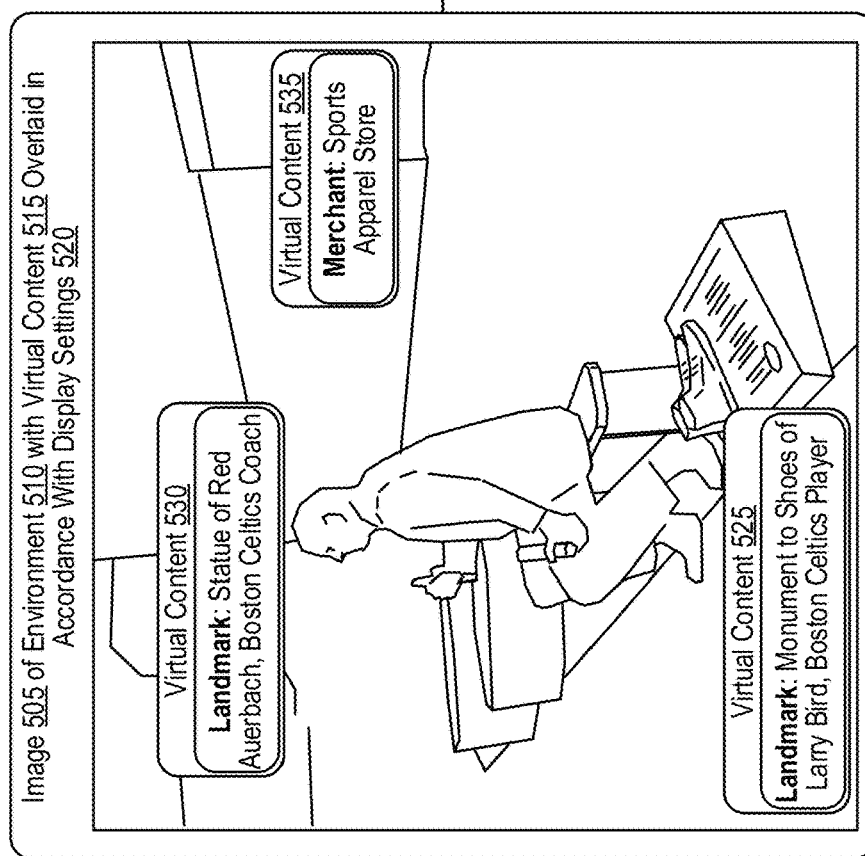

FIG. 5A is a conceptual diagram 500 illustrating an image 505 of an environment 510 in Boston before and after overlay of virtual content as displayed in accordance with display settings 520. On the left-hand side of FIG. 5A, the image 505 of the environment 510 in Boston is illustrated without (before) overlay of virtual content. On the right-hand side of FIG. 5A, the image 505 of the environment 510 in Boston is illustrated with (after) overlay of virtual content, including virtual content 525, virtual content 530, and virtual content 535. The virtual content is overlaid over the image 505 of the environment 510 in accordance with the display settings 520.

The image 505 of the environment 510 can be an example of an image captured by the environment-facing sensors 210 of the XR system 200. For example, the image 505 of the environment 510 can be an example of an image captured by the first camera 330A and/or the second camera 330B of the HMD 310. Similarly, the image 505 of the environment 510 can be an example of an image captured by the third camera 430C and/or the fourth camera 430D of the mobile handset 410. The image 505 of the environment 510 in Boston includes a view of the statue of Red Auerbach, coach of the Boston Celtics. The image 505 of the environment 510 in Boston includes a view of the monument to the shoes of Larry Bird, player on the Boston Celtics. The image 505 of the environment 510 in Boston includes a view of an entrance to a sports apparel store.

The virtual content 525, the virtual content 530, and the virtual content 535 are examples of the virtual content generated by the virtual content generator 215 of the XR system 200. The display settings 520 are examples of the first display settings 250 generated by the compositor 220 of the XR system 200. The virtual content 525 includes text reading "Landmark: Monument to Shoes of Larry Bird, Boston Celtics Player." Per the display settings, the virtual content 525 is overlaid over the image 505 of the environment 510 near the bottom of the image 505, where the monument to the shoes of Larry Bird is depicted in the image 505. The virtual content 530 includes text reading "Landmark: Statue of Red Auerbach, Boston Celtics Coach." Per the display settings, the virtual content 530 is overlaid over the image 505 of the environment 510 near the middle of the image 505, where the statue of Red Auerbach is depicted in the image 505. The virtual content 535 includes text reading "Merchant: Sports Apparel Store." Per the display settings, the virtual content 530 is overlaid over the image 505 of the environment 510 near the right-hand side of the image 505, where the entrance to the sports apparel store is depicted in the image 505.

FIG. 5B is a conceptual diagram 550 illustrating the image 505 of the environment 510 in Boston with the virtual content overlaid before and after a modification to the display settings 520. On the left-hand side of FIG. 5B, the image 505 of the environment 510 in Boston is illustrated with overlay of the virtual content in accordance with the display settings 520, like on the right-hand side of FIG. 5A. On the right-hand side of FIG. 5B, the image 505 of the environment 510 in Boston is illustrated with overlay of the virtual content in accordance with the display settings 555. The display settings 555 are different from the display settings 520. The display settings 555 can be an example of the second display settings 255 generated by the compositor 220 of the XR system 200. The modification to the display settings 520—that is, the modification from the display settings 520 to the display settings 555—can be an example of the modification, by the compositor 220 of the XR system 200, from the first display settings 250 to the second display settings 255.

According to the second display settings 555, the virtual content 535 (describing the sports apparel store) is now hidden, removed, and/or terminated from display. In some examples, this modification that removes the virtual content 535 in the second display settings 555 may be responsive to an indication from the XR system 200 (e.g., from the perception engine 235 and/or the comprehension engine 240) that the user has already perceived and/or understood the virtual content 535 to a high level. In some examples, this modification that removes the virtual content 535 in the second display settings 555 may be responsive to negative feedback to the virtual content 535 received via the feedback engine 260, such as a request to filter out virtual content related to merchants, intentional avoidance of the virtual content 535, detection of a negative verbalization from the user (e.g., "no") while the user is looking at the virtual content 535, or a combination thereof. In some examples, this modification that removes the virtual content 535 in the second display settings 555 may be responsive to positive feedback to the virtual content 525 and/or to the virtual content 530 received via the feedback engine 260, such as a request received from the user (e.g., via a user interface of the feedback engine 260) to focus on virtual content related to landmarks, or a high degree of focus on the virtual content 525 and/or to the virtual content 530.

According to the second display settings 555, the virtual content 525 (describing the monument to the shoes of Larry Bird) is now larger, with the text in a larger font, than under the first display settings 520. According to the second display settings 555, the virtual content 525 is emphasized and/or displayed more prominently and/or with higher priority than under the first display settings 520. The text of the virtual content 525 is also now lengthened, so that it now reads "Landmark: Monument to Shoes of Larry Bird, Boston Celtics Player from 1979-1992." In some examples, this modification that emphasizes the virtual content 525 in the second display settings 555 may be responsive to an indication from the XR system 200 (e.g., from the perception engine 235 and/or the comprehension engine 240) that the user has perceived the virtual content 525 to a sufficient level of a user perception (e.g., exceeding a threshold) but not yet comprehended the virtual content 525 to a sufficient comprehension level (e.g., exceeding a threshold). In some examples, this modification that emphasizes the virtual content 525 in the second display settings 555 may be responsive to an indication from the XR system 200 (e.g., from the perception engine 235 and/or the comprehension engine 240 and/or perception-related attribute engine 230) that the user is fixated on, and/or has experienced a saccade related to, and/or has experienced a pupil dilation while viewing, the virtual content 525. In some examples, this modification that emphasizes the virtual content 525 in the second display settings 555 may be responsive to positive feedback to the virtual content 525 received via the feedback engine 260, such as a heavy focus in the user's gaze on the virtual content and/or on the related depiction of the monument to the shoes of Larry Bird, detection of a positive verbalization from the user (e.g., "show me more about this") while the user is looking at the virtual content 525, or a combination thereof. In some examples, this modification that emphasizes the virtual content 525 in the second display settings 555 may be responsive to negative feedback to the virtual content 535 and/or the virtual content 530.

According to the second display settings 555, the virtual content 530 (describing the statue of Red Auerbach) has been moved to the right slightly, and has been moved backwards (in terms of depth) to appear behind part of the head of the statue of Red Auerbach. In some examples, this modification that moves the virtual content 530 in the second display settings 555 may be responsive to an indication from the XR system 200 (e.g., from the perception engine 235 and/or the comprehension engine 240) that the user has not yet perceived and/or comprehended the virtual content 530 to sufficient level(s) (e.g., exceeding threshold (s)). In some examples, this modification that moves the virtual content 530 in the second display settings 555 may be responsive to positive feedback to the virtual content 530 and/or to the virtual content 525 received via the feedback engine 260, such as a request received from the user (e.g., via a user interface of the feedback engine 260) to focus on virtual content related to landmarks.

Figure 6:
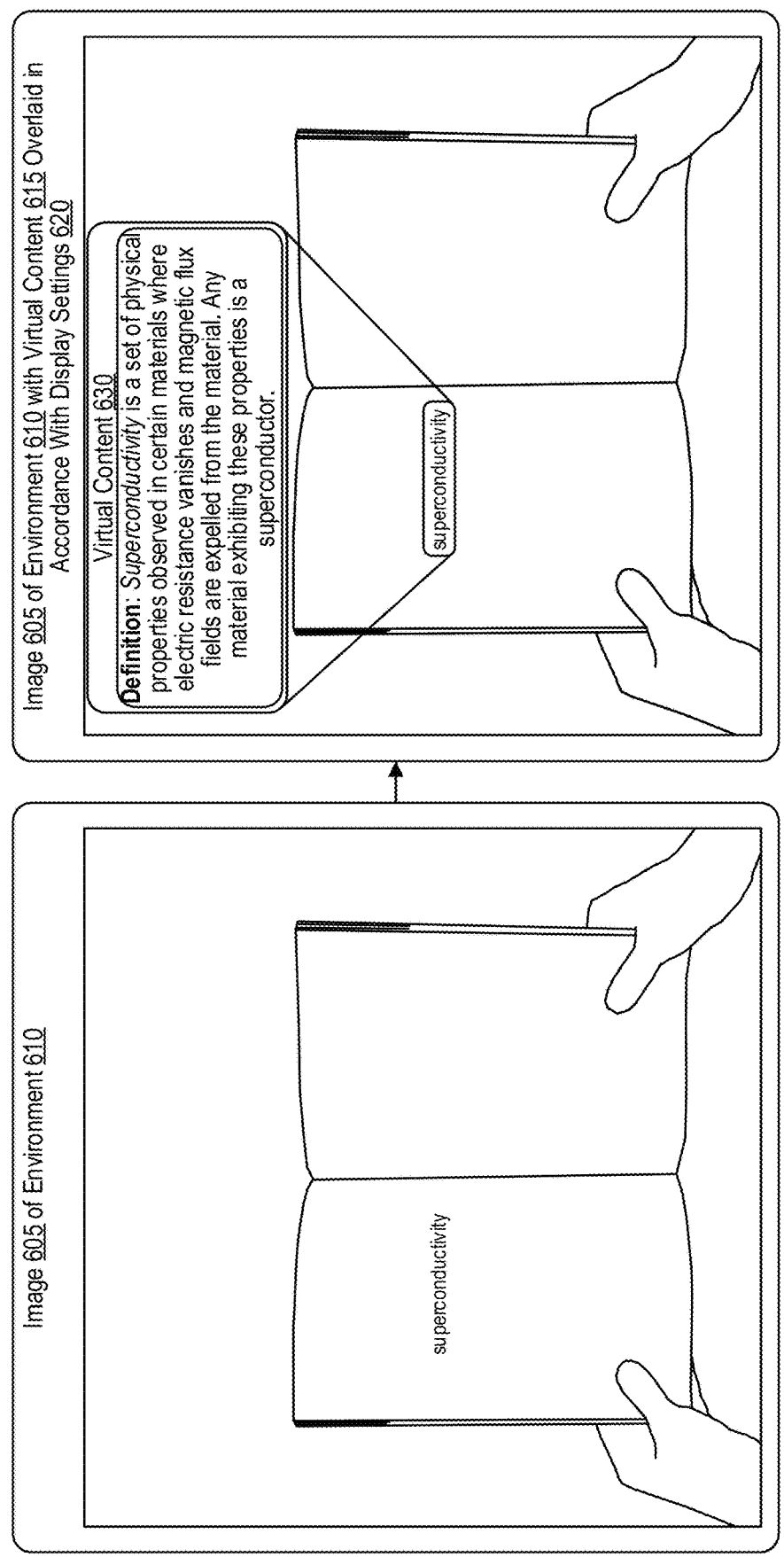
FIG. 6 is a conceptual diagram illustrating an image of an environment with a book before and after overlay of virtual content as displayed in accordance with display settings, in accordance with some examples.

FIG. 6 is a conceptual diagram 600 illustrating an image 605 of an environment 610 with a book before and after overlay of virtual content 630 as displayed in accordance with display settings 620. On the left-hand side of FIG. 6, the image 605 of the environment 610 with the book is illustrated without (before) overlay of virtual content 630. For the sake of clarity, the only word illustrated in the text of the book in the image 605 is "superconductivity." On the right-hand side of FIG. 6, the image 605 of the environment 610 with the book is illustrated with (after) overlay of virtual content 630. The virtual content 630 is overlaid over the image 605 of the environment 610 in accordance with the display settings 620.

The image 605 of the environment 610 can be an example of an image captured by the environment-facing sensors 210 of the XR system 200. For example, the image 605 of the environment 610 can be an example of an image captured by the first camera 330A and/or the second camera 330B of the HMD 310. Similarly, the image 605 of the environment 610 can be an example of an image captured by the third camera 430C and/or the fourth camera 430D of the mobile handset 410.

The virtual content 630 is an example of the virtual content generated by the virtual content generator 215 of the XR system 200. The display settings 620 are an example of the display settings (e.g., the first display settings 250, the second display settings 255) generated by the compositor 220 of the XR system 200. The virtual content 630 includes a highlighting of the word "superconductivity" in the book, with additional text overlaid above the book reading "Definition: Superconductivity is a set of physical properties observed in certain materials where electric resistance vanishes and magnetic flux fields are expelled from the material. Any material exhibiting these properties is a superconductor."

In some examples, the display of the virtual content 630 overlaid over the image 605 of the environment 610 with the book according to the display settings 620 may be responsive to a indication from the XR system 200 (e.g., from the perception engine 235 and/or the comprehension engine 240 and/or attribute engine 230) that the user is squinting and/or tilting their head while fixating on the word "superconductivity" in the book. In some examples, the XR system 200 provides definitions for other words in a similar manner. In some examples, the XR system 200 provides translations of words from one language to another in a similar manner.

Figure 7:
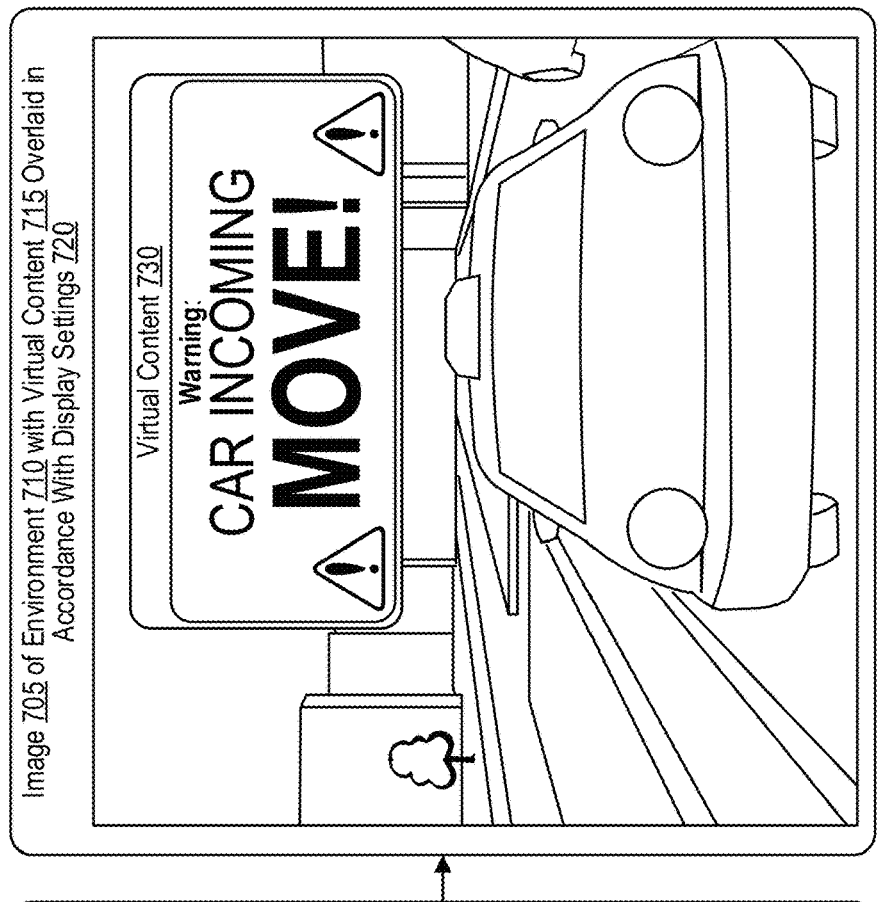
FIG. 7 is a conceptual diagram illustrating an image of an environment on a street before and after overlay of virtual content as displayed in accordance with display settings, in accordance with some examples.
Figure 7:
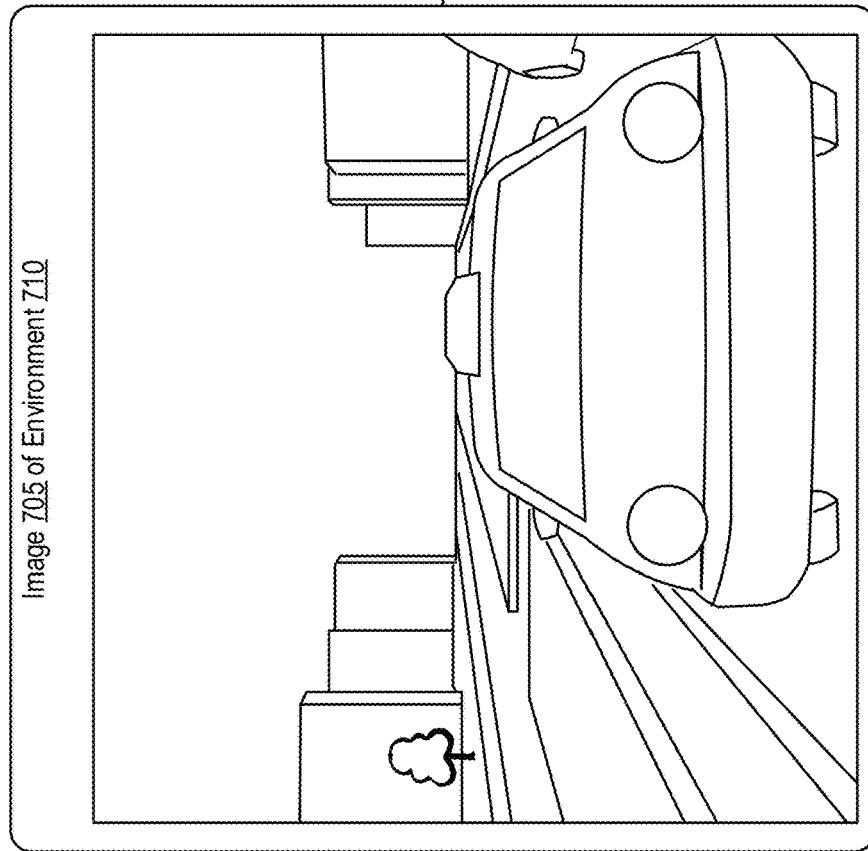

FIG. 7 is a conceptual diagram 700 illustrating an image 705 of an environment 710 on a street before and after overlay of virtual content 730 as displayed in accordance with display settings 720. On the left-hand side of FIG. 7, the image 705 of the environment 710 on the street is illustrated without (before) overlay of virtual content 730. On the right-hand side of FIG. 7, the image 705 of the environment 710 on the street is illustrated with (after) overlay of virtual content 730. The virtual content 730 is overlaid over the image 705 of the environment 710 in accordance with the display settings 720.

The image 705 of the environment 710 can be an example of an image captured by the environment-facing sensors 210 of the XR system 200. For example, the image 705 of the environment 710 can be an example of an image captured by the first camera 330A and/or the second camera 330B of the HMD 310. Similarly, the image 705 of the environment 710 can be an example of an image captured by the third camera 430C and/or the fourth camera 430D of the mobile handset 410.

The virtual content 730 is an example of the virtual content generated by the virtual content generator 215 of the XR system 200. The display settings 720 are an example of the display settings (e.g., the first display settings 250, the second display settings 255) generated by the compositor 220 of the XR system 200. The image 705 of the environment 710 on the street depicts a car driving toward the camera, and thus toward the user of the XR system 200. The virtual content 730 includes a warning, with warning icons and text reading "Warning: CAR INCOMING MOVE!" The warning, and the font size of the text, are large.

In some examples, the display of the virtual content 730 overlaid over the image 705 of the environment 710 on the street according to the display settings 720 may be responsive to detection of the car by the XR system 200 from the sensor data of the environment-facing sensors 210. The XR system 200 may include an object detection engine. The object detection engine may include a feature detection algorithm, a feature extraction algorithm, a feature recognition algorithm, a feature tracking algorithm, an object detection algorithm, an object recognition algorithm, an object tracking algorithm, a facial detection algorithm, a facial recognition algorithm, a facial tracking algorithm, a person detection algorithm, a person recognition algorithm, a person tracking algorithm, a vehicle detection algorithm, a vehicle recognition algorithm, a vehicle tracking algorithm, a classifier, or a combination thereof. The object detection engine can include one or more AI algorithms and/or ML system. The object detection engine can include, for example, the neural network 900. In some examples, the display of the virtual content 730 overlaid over the image 705 of the environment 710 on the street according to the display settings 720 may be responsive to an indication from the XR system 200 (e.g., from the perception engine 235 and/or the comprehension engine 240 and/or attribute engine 230) that the user has not perceived the car detected by the XR system 200 to a sufficient level (e.g., to a level exceeding a threshold).

Figure 8:
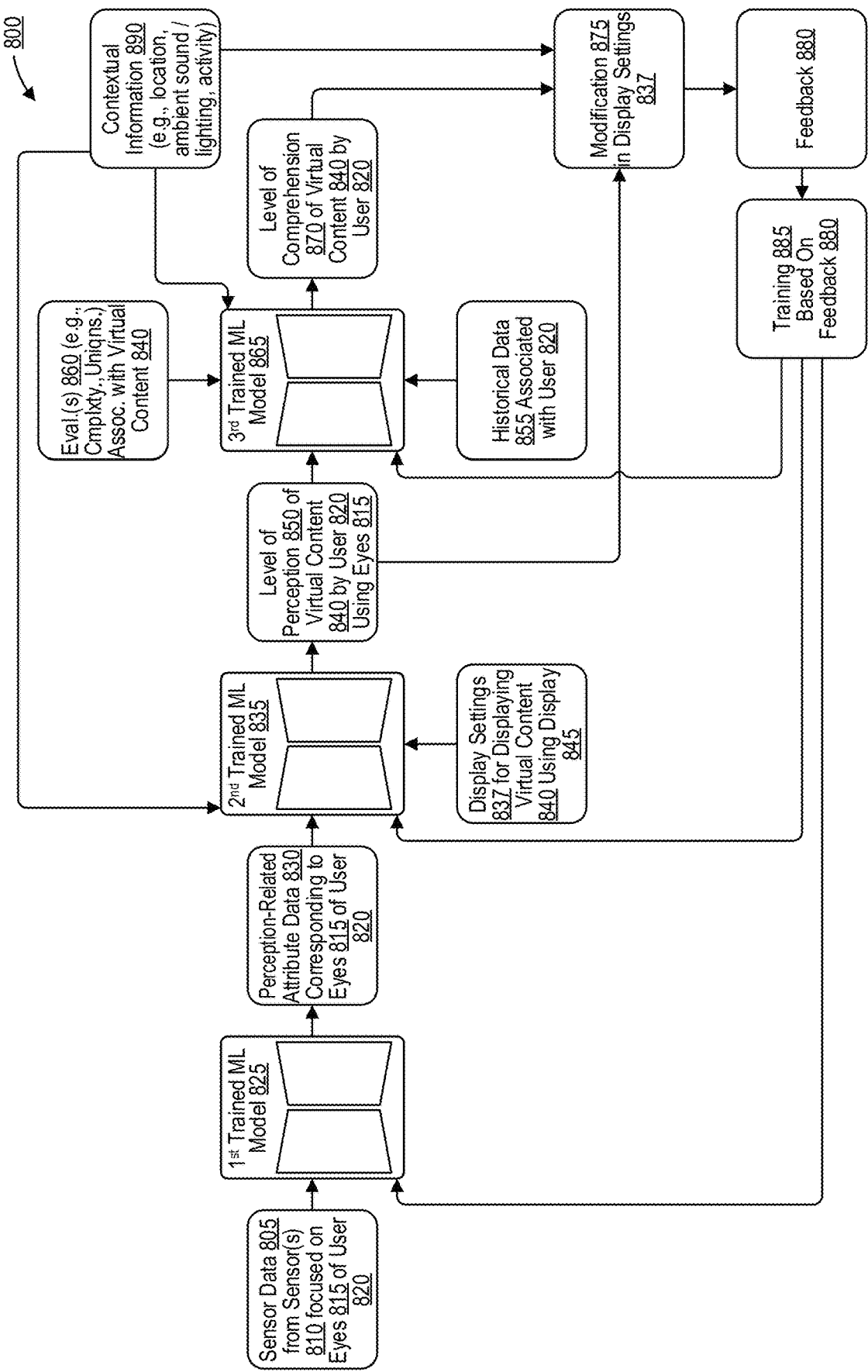
FIG. 8 is a block diagram illustrating a process for determining levels of perception and comprehension of virtual content based on one or more trained machine learning (ML) models, in accordance with some examples.

FIG. 8 is a block diagram 800 illustrating a process for determining levels of perception and comprehension of virtual content based on one or more trained machine learning (ML) models. The process of FIG. 8 is performed by an imaging system, such as the XR system 200 of FIG. 2.

The process begins with capture of sensor data 805 by one or more sensors 810 facing one or both eye(s) 815 of a user 820. The sensors 810 can be examples of the user-facing sensors 205 of the XR system 200. The imaging system provides the sensor data 805, as an input, to a first trained ML model 825. The first trained ML model 825 may be a part of the imaging system. The first trained ML model 825 may be a part of the attribute engine 230 of the XR system 200, in some examples. In response to receipt of the sensor data 805 as inputs, the first trained ML model 825 outputs perception-related attribute data 830 corresponding to the eye(s) 815 of the user 820. The perception-related attribute data 830 can identify, for example, movements of the user's eye(s), pupil dilations, blinking, squinting, saccades, fixations, eye moisture levels, and the like.

The imaging system provides the perception-related attribute data 830, as an input, to a second trained ML model 835. The imaging system also provides display settings 837 for displaying the virtual content 840 via a display 845, as an input, to the second trained ML model 835. The display 845 is an example of the display 225 of the XR system 200. The display settings 837 are examples of the first display settings 250 and/or the second display settings 255 of the XR system 200. The imaging system can also provide contextual information 890, as an input, to the second trained ML model 835. The contextual information can include, for example, location of the imaging system, ambient sound, ambient lighting, activities detected as being performed by the user, and the like.

The second trained ML model 835 may be a part of the imaging system. The second trained ML model 835 may be a part of the perception engine 235 of the XR system 200, in some examples. In response to receipt of the perception-related attribute data 830 and/or the display settings 837 and/or contextual information 890 as inputs, the second trained ML model 835 outputs an level of perception 850 of virtual content 840 by the user 820 using the eye(s) 815. The virtual content 840 can be an example of the virtual content generated by the virtual content generator 215 of the XR system 200 and displayed by the display 225 of the XR system 200 according to display settings (e.g., first display settings 250, second display settings 255) determined by the compositor 220 of the XR system 200. The level of perception 850 of the virtual content 840 by the user 820 can be based on, for example, the extent (e.g., based on time and/or distance) to which the gaze of the user 820's eye(s) 815 falls on, or near, the position(s) on the display 845 where the virtual content 840 is displayed in accordance with the display settings 837.

The imaging system provides the level of perception 850 of the virtual content 840 by the user 820, as an input, to a third trained ML model 865. In some examples, the imaging system may also provide historical data 855 associated with the user 820, as an input, to the third trained ML model 865.

In some examples, the imaging system may also provide contextual information 890, as an input, to the third trained ML model 865. The historical data 855 associated with the user 820 can identify, for example, the education level of the user 820, the profession of the user 820, information about the historical actions of the user 820, and/or any other historical information associated with the user. In some examples, the imaging system may also provide one or more characteristics of the virtual content, as an input, to the third trained ML model 865. For example, the one or more characteristics of the virtual content may include evaluations of the virtual content 840 generated by a virtual content evaluation engine (e.g., such as the virtual content evaluation engine 245 of the XR system 200). The evaluations can include, for example, one or more metrics on the complexity and/or uniqueness of the virtual content 840. In some examples, the virtual content evaluation engine can generate a complexity metric and a uniqueness metric, and can convert these two metrics into a single combined metric that thus reflects both complexity and uniqueness. In some examples, the virtual content evaluation engine averages a value of the uniqueness metric and a value of the complexity metric to generate the combined metric. In some examples, the virtual content evaluation engine multiplies a value of the uniqueness metric and a value of the complexity metric to generate the combined metric. In some examples, the virtual content evaluation engine adds a value of the uniqueness metric and a value of the complexity metric to generate the combined metric.

The third trained ML model 865 may be a part of the imaging system. The third trained ML model 865 may be a part of the comprehension engine 240 of the XR system 200, in some examples. In response to receipt of the level of perception 850, the historical data 855, the evaluation(s) 860, and/or contextual information 890 as inputs, the third trained ML model 865 outputs a level of comprehension 870 of virtual content 840 by the user 820. The level of comprehension 870 can be referred to as an extent of comprehension 870 and/or as a metric of comprehension 870. The level of comprehension 870 can be based on, for example, the extent to which the level of perception 850 aligns with or exceeds a level appropriate considering the complexity and/or uniqueness of the virtual content 840 (e.g., based on the evaluation(s) 860), based on the user 820's own background (e.g., based on the historical data 855), based on contextual information 890, or a combination thereof.

The imaging system uses one or more of the level of comprehension 870 of the virtual content 840, the level of perception 850 of the virtual content 840, the perception-related attribute data 830, and/or contextual information 890 as bases for generating a modification 875 to the display settings 837. The modification 875 to the display settings 837 can be an example of the modification from the first display settings 250 to the second display settings 255 by the compositor 220 of the XR system 200. The imaging system can receive feedback 880, for example via a user interface of a feedback engine (e.g., the feedback engine 260). The imaging system can perform additional training 885, based on the feedback 880, of the first trained ML model 825, the second trained ML model 835, and/or the third trained ML model 865. The imaging system can use feedback 880 that is positive, in the training 885, to reinforce weights in the first trained ML model 825, the second trained ML model 835, and/or the third trained ML model 865. The imaging system can use feedback 880 that is negative, in the training 885, to modify, remove, or add weights in the first trained ML model 825, the second trained ML model 835, and/or the third trained ML model 865. Although the first trained ML model 825, the second trained ML model 835, and the third trained ML model 865 are illustrated as separate ML models in FIG. 8, it should be understood the any two (or all three) of these ML models can be realized in a single ML model. Furthermore, in some examples, any of the trained ML models illustrated in FIG. 8 (e.g., the first trained ML model 825, the second trained ML model 835, or the third trained ML model 865) can be divided into two or more subsidiary trained ML models. For instance, one subsidiary trained ML model can receive the input(s) illustrated in FIG. 8 associated with trained ML model in question, and can generate intermediate data. Another subsidiary trained ML model can receive the intermediate data as at last one of its input(s), and can generate the output(s) illustrated in FIG. 8 associated with trained ML model in question, The level of perception 850 and/or the level of comprehension 870 of the user 820 can include factors that pertain to the user's cognitive capabilities and state. Examples of cognitive-based factors can include prior experience and/or skill level with a particular task, such as a particular XR task (e.g., reading a notification), a particular real-world task (e.g., cooking in the kitchen), a particular real-world task that is augmented (e.g., walking in a city and receiving navigation instructions), information about the user's educational level, information about the user's knowledge level in a particular field, information about the user's profession, information about the user's cognitive impairments, among others, or combinations thereof. Examples of cognitive-based factors can alternatively or additionally include the attention applied to the augmented content, such as saccades (type of eye movement used to move the fovea from one point to another) and fixation time, dwell time, repeat viewing, interaction with the content (e.g., scrolling, responding, dismissing, etc.), among others. Examples of cognitive-based factors can alternatively or additionally include a user's mental state, such as alertness, fatigue, attention divided among more than one activity, among others.

The context of use of the XR system can include aspects of the real-world environment while the XR system is in use. Examples of such aspects can include noise level in the environment (e.g., ambient sound, additional person speaking in the environment, etc.), lighting in the environment (e.g., ambient lighting), the user's activity, the location at which the XR system is being used, past history of interacting with content, time of day, whether the environment is static or dynamic (e.g., if the user is on a moving object, such as a vehicle, train, elevator, escalator, etc.), obstacle(s) in the environment, among others.

The information associated with the content being output by the XR system can include characteristics of the virtual content and/or characteristics of physical content (e.g., an object of an augmentation). Examples of such characteristics can include the semantic complexity of a message or other virtual content, the severity and criticality of a message or other virtual content, the length of a message or other virtual content, the relevance of a message or other virtual content to a task being performed (e.g., reading a book), the distinctiveness of the virtual content relative to the environment, whether a message or other virtual content is contextually expected (e.g., would receiving the message content be appropriate or relevant to the situation, time, place, activity, etc.).

In some aspects, the XR system can monitor other external factors, such as user input, display duration(s) of previously-presented virtual content, device status (e.g., power status, such as low power), AR device screen resolution, traveling speed of the XR system (and thus the user), and/or other external factors.

The systems and techniques can be used to determine initial presentation of content in the XR system and/or to assess the user perception of virtual content and to determine potential outcomes. For example, to determine an initial presentation of content, the XR system can monitor a user's cognitive state, the context of use (e.g., aspects of the real-world environment), the task being performed. In some cases, the XR system can monitor the content, which can include a physical object on which augmented content may be displayed. Based on the cognitive state, the context of use, and the task (and in some cases the content), the XR system can determine that an augmentation would be beneficial. The XR system can then provide (e.g., output) the augmentation, which can be tailored to the cognitive state, context, and task (and in some cases the content). In one illustrative example, the task can include the user reading a book in a library, the cognition can include that the user is sleepy and may not be absorbing material well (e.g., based on the XR system monitoring saccades and other eye characteristics), the context can include the room in which the user is located is bright based on being in a library and near a window mid-day (e.g., based on input from an ambient light sensor and a Global Navigation Satellite System (GNSS) receiver), and the content can include a challenging book on physics the user is reading and that the user has not had a physics course before. While reading the book, the AR device can determine that the user stares at a word and squints both eyes. The AR device can then determine that a definition or translation for the world would be useful to display as a popup relative to the word.

As noted above, the systems and techniques can be used to assess the user perception of virtual content and to determine potential outcomes. For example, the XR system can present virtual content (e.g., a warning notification such as "low battery", AR content such as an arrow next to a switch with a label of "Do not press this button", AR content with information associated with a point or place of interest, etc.). If a user completes a task associated with the virtual content or manually dismisses the virtual content, the XR system can remove the virtual content. Otherwise, the XR system can perform an analysis to determine whether the user has perceived the virtual content.

To assess the user perception of virtual content by the user, the systems and techniques can determine an level of perception of the virtual content, or a degree of user perception of the virtual content. In some examples, to determine whether the user has perceived the virtual content, and/or the level or degree of perception of the virtual content, the XR system can evaluate the content, perform eye analysis (e.g., saccade analysis) of the user, and/or perform a secondary analysis (e.g., by checking pupils, squinting, and head movement) of the user. In some cases, the XR system can use machine learning (ML)-based pattern recognition (e.g., using one or more neural networks) do determine whether the user has perceived the virtual content. If it is determined that the user has perceived the virtual content (e.g., looked in the direction of the virtual content for more than a threshold amount of time), the XR system can dismiss or remove the virtual content (e.g., remove the content from display). If the XR system determines that the user has not perceived the virtual content, the XR system can determine (e.g., based on context, such as ambient light, noise, user activity, etc.) whether to maintain the content in place, whether to boost the saliency of the content (e.g., based on the context), and/or perform other actions. For instance, if the context indicates that the ambient light is bright, the XR system can boost the display brightness. In another example, if the context indicates that the ambient environment is loud, the XR system can increase the volume of the AR content (e.g., when audible virtual content is output).

In some aspects, to perform the eye analysis, the XR system can turn on eye tracking cameras and can use the eye tracking cameras to track the eyes over the virtual content. For instance, the XR system can disambiguate attention paid to the virtual content versus attention paid something in the field of view behind the virtual content. If a low value is determined for the virtual content (e.g., a value less than a threshold value, such as a threshold value of 10), then the XR system can remove the virtual content. If a high value is determined for the virtual content (e.g., a value greater than the threshold value), the XR system can maintain the content in place for a period of time (e.g., 5 seconds, 10 seconds, etc.) to give the user time to re-read the content. If the XR system determines the user is re-reading the virtual content, the XR system can leave the content in place.

In some aspects, to perform the secondary analysis, the XR system can check the user's pupils, whether the user is squinting, and/or the head movement of the user. For instance, the XR system can maintain the content in place if it determines that one or more of the user's pupils are not dilated, the user is squinting, the user's head is cocked sideways or craned forward, the user is blinking frequency, the user is staring at the virtual content for a certain duration (e.g., 3 seconds or more), the user looks at the content with a certain frequency (e.g., 2 times per second).

In some cases, over time, the XR system can learn (e.g., using ML-based pattern recognition) and optimize the time that a message should remain in place for a user. The XR system may determine a likelihood that the virtual content will be read and/or viewed in a threshold amount of time (e.g., within a threshold period of time, such as 1 second, 2 seconds, 3 seconds, 4 seconds, 5 seconds, 10 seconds, 15 seconds, etc.). In some examples, the XR system may develop confidence levels for displayed virtual content (e.g., virtual messages or notifications) to determine the likelihood. In some cases, if a high degree of likelihood is determined for a given item of virtual content, the XR system may not utilize the eye tracking cameras for the eye analysis described above.

Figure 9:
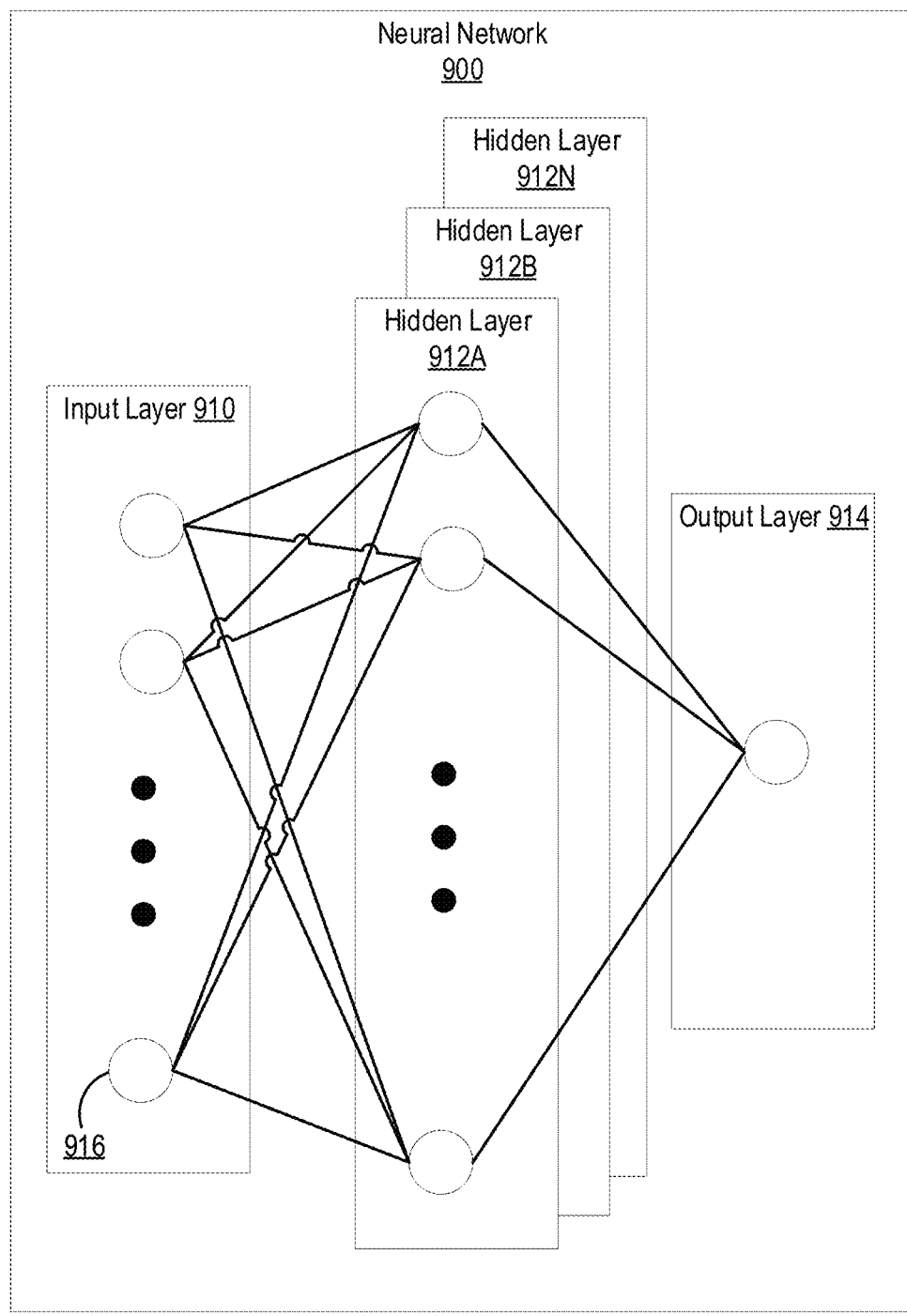
FIG. 9 is a block diagram illustrating an example of a neural network that can be used by the trained machine learning system for analysis of a user viewing extended reality content, in accordance with some examples.

FIG. 9 is a block diagram illustrating an example of a neural network (NN) 900 that can be used by the trained machine learning system for analysis of a user viewing extended reality content. The neural network 900 can include any type of deep network, such as a convolutional neural network (CNN), an autoencoder, a deep belief net (DBN), a Recurrent Neural Network (RNN), a Generative Adversarial Networks (GAN), and/or other type of neural network. The neural network 900 may be an example of one of the one or more trained neural networks of the first trained ML model 825, of the second trained ML model 835, of the third trained ML model 865, or a combination thereof.

An input layer 910 of the neural network 900 includes input data. The input data of the input layer 910 can include data representing the pixels of one or more input image frames. In some examples, the input data of the input layer 910 includes data representing the pixels of image data (e.g., of images captured by the user-facing sensors 205, the third camera 330C, the fourth camera 330D, the first camera 430A, the second camera 430B, and/or the sensors 810) and/or metadata corresponding to the image data. In some examples, the input data of the input layer 910 includes images captured by the user-facing sensors 205, the third camera 330C, the fourth camera 330D, the first camera 430A, the second camera 430B, and/or the sensors 810.

In some examples, the input data of the input layer 910 can include perception-related attribute data, such as perception-related attribute data 830 and/or perception-related attribute data generated by the attribute engine 230. In some examples, the input data of the input layer 910 can include display settings for displaying virtual content, such as the first display settings 250, the second display settings 255, the display settings 6520, the display settings 555, the display settings 620, the display settings 720, the display settings 837, or a combination thereof.

In some examples, the input data of the input layer 910 can include an level of perception of virtual content by a user through the eyes of the user, such as the level of perception 850 and/or the level of perception determined using the perception engine 235. In some examples, the input data of the input layer 910 can include historical data associated with a user, such as the historical data 855. In some examples, the input data of the input layer 910 can include one or more evaluations associated with the virtual content, such as the evaluation(s) 860, evaluation(s) and/or metric(s) generated by the virtual content evaluation engine 245, or a combination thereof. In some examples, the input data of the input layer 910 can include contextual data and/or contextual information, such as the contextual information 890. In some aspects, the evaluation(s) 860 can be referred to as metric(s) and/or score(s).

The images can include image data from an image sensor including raw pixel data (including a single color per pixel based, for example, on a Bayer filter) or processed pixel values (e.g., RGB pixels of an RGB image). The neural network 900 includes multiple hidden layers 912A, 912B, through 912N. The hidden layers 912A, 912B, through 912N include "N" number of hidden layers, where "N" is an integer greater than or equal to one. The number of hidden layers can be made to include as many layers as needed for the given application. The neural network 900 further includes an output layer 914 that provides an output resulting from the processing performed by the hidden layers 912A, 912B, through 912N. In some examples, the output layer 914 can provide an output image. In some examples, the output layer 914 can provide perception-related attribute data, such as perception-related attribute data 830 and/or perception-related attribute data generated by the attribute engine 230. In some examples, the output layer 914 can provide an level of perception of virtual content, such as the level of perception 850 and/or the level of perception determined using the perception engine 235. In some examples, the output layer 914 can provide a level of comprehension and/or understanding of virtual content by a user, such as the level of comprehension 870 and/or the level of comprehension determined using the comprehension engine 240.

The neural network 900 is a multi-layer neural network of interconnected filters. Each filter can be trained to learn a feature representative of the input data. Information associated with the filters is shared among the different layers and each layer retains information as information is processed. In some cases, the neural network 900 can include a feed-forward network, in which case there are no feedback connections where outputs of the network are fed back into itself. In some cases, the network 900 can include a recurrent neural network, which can have loops that allow information to be carried across nodes while reading in input.

In some cases, information can be exchanged between the layers through node-to-node interconnections between the various layers. In some cases, the network can include a convolutional neural network, which may not link every node in one layer to every other node in the next layer. In networks where information is exchanged between layers, nodes of the input layer 910 can activate a set of nodes in the first hidden layer 912A. For example, as shown, each of the input nodes of the input layer 910 can be connected to each of the nodes of the first hidden layer 912A. The nodes of a hidden layer can transform the information of each input node by applying activation functions (e.g., filters) to this information. The information derived from the transformation can then be passed to and can activate the nodes of the next hidden layer 912B, which can perform their own designated functions. Example functions include convolutional functions, downscaling, upscaling, data transformation, and/or any other suitable functions. The output of the hidden layer 912B can then activate nodes of the next hidden layer, and so on. The output of the last hidden layer 912N can activate one or more nodes of the output layer 914, which provides a processed output image. In some cases, while nodes (e.g., node 916) in the neural network 900 are shown as having multiple output lines, a node has a single output and all lines shown as being output from a node represent the same output value.

In some cases, each node or interconnection between nodes can have a weight that is a set of parameters derived from the training of the neural network 900. For example, an interconnection between nodes can represent a piece of information learned about the interconnected nodes. The interconnection can have a tunable numeric weight that can be tuned (e.g., based on a training dataset), allowing the neural network 900 to be adaptive to inputs and able to learn as more and more data is processed.

The neural network 900 is pre-trained to process the features from the data in the input layer 910 using the different hidden layers 912A, 912B, through 912N in order to provide the output through the output layer 914.

Figure 10:
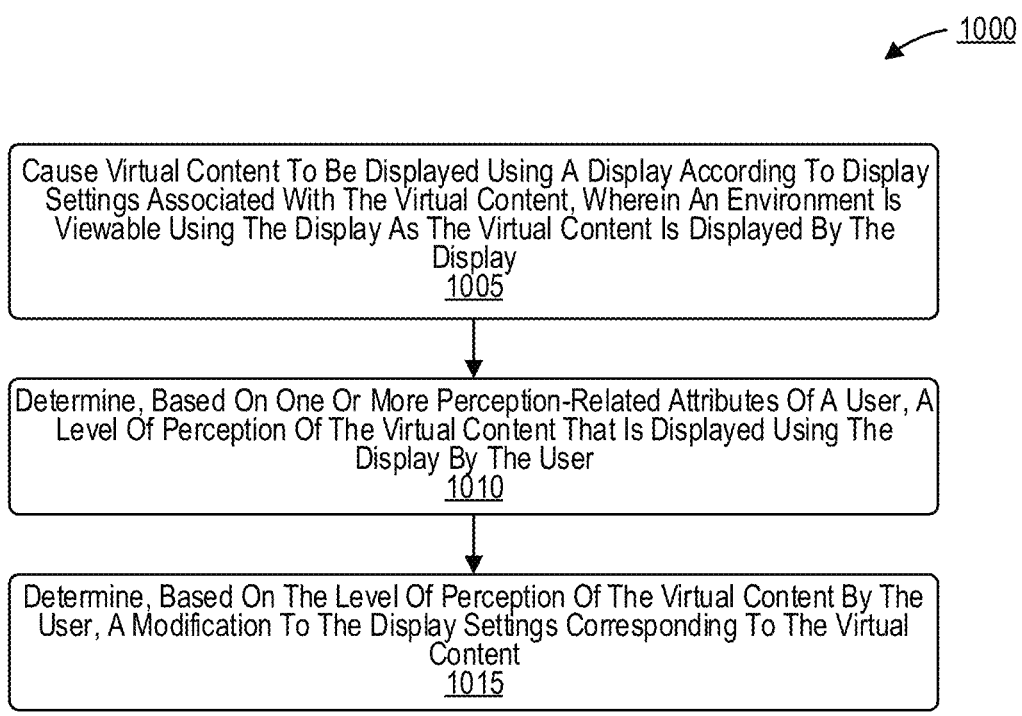
FIG. 10 is a flow diagram illustrating a process for extended reality (XR) display operation, in accordance with some examples.

FIG. 10 is a flow diagram illustrating a process for extended reality (XR) display operation. The process 1000 may be performed by an imaging system. In some examples, the imaging system can include, for example, the image capture and processing system 100, the image capture device 105A, the image processing device 105B, the image processor 150, the ISP 154, the host processor 152, the XR system 200, the HMD 310, mobile handset 410, the imaging device that captures the image 505 and overlays the virtual content 525-535, the imaging device that captures the image 605 and overlays the virtual content 630, the imaging device that captures the image 705 and overlays the virtual content 730, the imaging device of FIG. 8, the first trained ML model 825, of the second trained ML model 835, the third trained ML model 865, the neural network 900, the computing system 1100, the processor 1110, or a combination thereof.

At operation 1005, the imaging system is configured to, and can, cause virtual content to be displayed using a display according to display settings associated with the virtual content, wherein an environment is viewable using the display as the virtual content is displayed by the display. In some examples, the imaging system includes the display. Examples of the display include the display 225, the display(s) 340, the display 440, the display 845, the output device 1135, other displays described herein, or a combination thereof. Examples of the virtual content include the virtual content generated by the virtual content generator 215, the virtual content 515, the virtual content 525, the virtual content 530, the virtual content 535, the virtual content 615, the virtual content 630, the virtual content 715, the virtual content 730, the virtual content 840, other virtual content described herein, or a combination thereof. Examples of the display settings include the first display settings 250, the second display settings 255, the display settings 520, the display settings 555, the display settings 620, the display settings 720, the display settings 837 (before the modification 875), the display settings 837 (after the modification 875), other display settings described herein, or a combination thereof.

In some examples, the imaging system is configured to, and can, generate the virtual content before causing the virtual content to be displayed using the display. For instance, a virtual content generator 215 of the imaging system can generate the virtual content. In some examples, a compositor 220 of the imaging system can generate the display settings.

In some examples, the environment is viewable using the display at least in part based on light from the environment passing through at least a portion of the display. For instance, the display may be at least partially transparent, translucent, light-receptive, light-transmissive, and/or light-permissive. In such examples, the imaging system may be referred to as having an optical see-through display. In such examples, the imaging system can cause at least a portion of the virtual content to be displayed over at least a portion of the view of the environment using the display according to display settings. In some aspects, a compositor 220 of the imaging system can generate the display settings to overlay at least a portion of the virtual content over the view of the environment. In some aspects, a compositor 220 of the imaging system can generate the display settings to display a displayed portion of the virtual content at a simulated depth such that at least a portion of the environment appears to be in front of at least a hidden portion of the virtual content that is not displayed per the display settings.

In some examples, the environment is viewable using the display at least in part based on the imaging system causing a view of the environment to be displayed by the display. For instance, the imaging system can capture on or more images that depict the view of the environment using one or more environment-focused sensors 210 of the imaging system. The imaging system can cause the display to display the one or more images of the environment in combination with the virtual content. For instance, the imaging system can cause the virtual content to be displayed by combining and/or compositing at least a portion of the virtual content with at least portions of the one or more images of the environment to generate composited image(s), for instance using a compositor 220 of the imaging system, and causing the display to display the resulting composited image(s). In some aspects, a compositor 220 of the imaging system can generate the display settings to overlay at least a portion of the virtual content over at least a portion the view of the environment in the one or more images of the environment. In some aspects, a compositor 220 of the imaging system can generate the display settings to display a displayed portion of the virtual content at a simulated depth such that at least a portion of the environment (from the one or more images of the environment) appears to be in front of at least a hidden portion of the virtual content that the environment overlays per the display settings.

At operation 1010, the imaging system is configured to, and can, determine, based on one or more perception-related attributes of a user, a level of perception of the virtual content that is displayed using the display by the user. The level of perception may be referred to as an extent of perception and/or as a metric of perception. In some examples, the imaging system can determine the perception-related attributes of the user using an attribute engine 230 of the imaging system, a first trained ML model 825 of the imaging system, a neural network 900, or a combination thereof. Examples of the perception-related attributes include perception-related attributes determined using the attribute engine 230, the perception-related attribute data 830, perception-related attributes determined using the NN 900, or a combination thereof.

In some examples, the imaging system can determine the level of perception of the virtual content by the user using a perception engine 235 of the imaging system, a second trained ML model 835 of the imaging system, a neural network 900, or a combination thereof. In some examples, the level of perception includes a level of comprehension, and the imaging system can determine the level of perception and/or the level of comprehension using a perception engine 235 of the imaging system, a comprehension engine 240 of the imaging system, a virtual content evaluation engine 245 of the imaging system, a second trained ML model 835 of the imaging system, a third trained ML model 865 of the imaging system, a neural network 900, or a combination thereof. Examples of the level of perception of the virtual content by the user include the level of perception determined using the perception engine 235, the level of perception 850, a level of perception determined using the NN 900, or a combination thereof. In some examples, the level of perception includes a level of comprehension, and examples of the level of perception and/or the level of comprehension include the level of perception determined using the perception engine 235, the level of comprehension determined using the comprehension engine 240, the level of perception 850, the level of comprehension 870, a level of perception determined using the NN 900, a level of comprehension determined using the NN 900, or a combination thereof.

In some examples, the one or more perception-related attributes of the user are associated with one or more eyes of the user. In some examples, the one or more perception-related attributes of the user include at least one of: one or more attributes of one or more eyes of the user, one or more attributes of one or more facial expressions of the user, one or more gestures of the user, or a combination thereof. In some examples, determining the one or more perception-related attributes of the user includes tracking eye position(s) of the eye(s) of the user, tracking eye position(s) of the eye(s) of the user, tracking eye movement(s) of the eye(s) of the user, tracking pupil dilation(s) of the eye(s) of the user, tracking saccade(s) of the eye(s) of the user, tracking fixation(s) by the eye(s) of the user, tracking blinking by the eyelid(s) of the user, tracking squinting by the eyelid(s) of the user, tracking optokinetic reflex(es) by the eye(s) of the user, tracking vestibulo-ocular reflex(es) by the eye(s) of the user, tracking accommodation reflex(es) by the eye(s) of the user, tracking facial expressions of the user, tracking gestures by the user, or combinations thereof. Tracking, in the operations listed above, can refer tracking of timing, frequency, extent, amplitude, eye position, eye movement, eye speed, or a combination thereof.

In some examples, the one or more perception-related attributes of the user include one or more eye positions of one or more eyes of the user relative to the virtual content. In some examples, the one or more perception-related attributes of the user include one or more characteristics of one or more saccades by one or more eyes of the user. The one or more characteristics include at least one of a frequency, a duration, a timing, a saccade speed, a saccade amplitude, an eye position, an eye movement, other characteristics discussed herein, or combinations thereof. In some examples, the one or more perception-related attributes of the user include one or more characteristics of one or more fixations by one or more eyes of the user. The one or more characteristics include at least one of a frequency, a duration, a timing, an eye position, and an eye movement. In some examples, the one or more perception-related attributes of the user include one or more characteristics of one or more pupil dilations by one or more eyes of the user. The one or more characteristics include at least one of a frequency, a duration, a timing, a level of pupil dilation, an eye position, and an eye movement. In some examples, the one or more perception-related attributes of the user include one or more characteristics of one or more blinks by one or more eyelids of the user. The one or more characteristics include at least one of a frequency, a duration, a timing, a blink speed, an eye position, and an eye movement. In some examples, the one or more perception-related attributes of the user include one or more characteristics of one or more squints by one or more eyelids of the user. The one or more characteristics include at least one of a frequency, a duration, a timing, a level of squinting, an eye position, and an eye movement.

In some examples, the imaging system is configured to, and can, receive sensor data captured by one or more sensors. The sensor data is indicative of one or more eyes of the user. The imaging system is further configured to, and can, determine the one or more perception-related attributes of the user based on the sensor data. In some examples, the imaging system includes the one or more sensors. In some examples, the one or more sensors are configured to, and can, capture the sensor data. Examples of the one or more sensors include the user-facing sensor(s) 205, the additional sensor(s) 208, the sensor(s) 810, the third camera 330C, the fourth camera 330D, the first camera 430A, the second camera 430B, the input device 1145, other sensors described herein, or combinations thereof. Examples of the sensor data include sensor data captured by any of the sensors listed in the previous sentence, for instance including the sensor data 805. In some examples, the one or more sensors include one or more image sensors, and the sensor data includes one or more images, videos, or combinations thereof. In some examples, the sensor data includes representation of one or more eyes of the user. In some examples, the sensor data includes In some examples, determining the level of perception of the virtual content by the user includes using the one or more perception-related attributes of the user as inputs to one or more trained machine learning systems. Examples of the one or more trained ML systems include the attribute engine 230, the perception engine 235, the comprehension engine 240, the first trained ML model 825, the second trained ML model 835, the third trained ML model 865, the NN 900, or a combination thereof. In some examples, the imaging system is configured to, and can, receive, through a user interface, feedback corresponding to the level of perception of the virtual content by the user. In some examples, the imaging system is configured to, and can, update the one or more trained machine learning systems based on the feedback. In some examples, the imaging system includes a feedback engine 260 that the imaging system uses to receive the feedback and update the trained ML systems using further training and/or learning of the trained ML systems. Examples of the feedback include the feedback 880. Examples of the training include the training 885.

In some examples, the imaging system is configured to, and can, determine a level of comprehension of the virtual content by the user based on the level of perception of the virtual content by the user. In some examples, determining the level of perception of the virtual content by the user includes determining the level of comprehension of the virtual content by the user. The imaging system is configured to, and can, determine the modification to the display settings based on the level of comprehension and/or the level of perception. In some examples, determining the level of comprehension of the virtual content by the user is based on the one or more perception-related attributes of the user, one or more characteristics of the virtual content, contextual data, historical information associated with the user, a user profile of the user, an evaluation of the complexity of the virtual content, an evaluation of the uniqueness of the virtual content, or a combination thereof. In some examples, the imaging system is configured to, and can, receive historical information associated with the user. In some examples, determining the level of comprehension of the virtual content by the user is based on the historical information about the user. In some examples, the user profile comprises historical data associated with the user. In some examples, the contextual data comprises one or more reactions by the user to the virtual content. In some examples, the contextual data comprises a location of the XR system.

In some examples, the imaging system can determine the level of comprehension using a perception engine 235 of the imaging system, a comprehension engine 240 of the imaging system, a virtual content evaluation engine 245 of the imaging system, a second trained ML model 835 of the imaging system, a third trained ML model 865 of the imaging system, a neural network 900, or a combination thereof. Examples of the level of comprehension include the level of comprehension determined using the comprehension engine 240, the level of comprehension 870, a level of comprehension determined using the NN 900, or a combination thereof.

In some examples, the imaging system is configured to, and can, determine a characteristic of the virtual content, for instance using the virtual content evaluation engine 245, wherein determining the level of perception and/or the level of comprehension of the virtual content by the user is based on the characteristic of the virtual content. Examples of the characteristic include evaluation(s) by the virtual content evaluation engine 245, the evaluation(s) 860 associated with the virtual content 840, or combinations thereof. In some examples, the imaging system is configured to, and can, determine a level of complexity of the virtual content. In some aspects, determining the level of perception and/or the level of comprehension of the virtual content by the user is based on the level of complexity of the virtual content. In some examples, the imaging system is configured to, and can, determine a level of uniqueness of the virtual content. In some aspects, determining the level of perception and/or the level of comprehension of the virtual content by the user is based on the level of uniqueness of the virtual content. In some examples, the imaging system is configured to, and can, determine a level of distinctiveness of the virtual content relative to the environment. In some aspects, determining the level of perception and/or level of comprehension of the virtual content by the user is based on the level of distinctiveness of the virtual content relative to the environment.

In some examples, determining the level of perception of the virtual content by the user includes determining that the user has perceived the virtual content. In some examples, determining the level of perception of the virtual content by the user includes determining that the user has not perceived the virtual content. In some examples, determining the level of perception of the virtual content by the user includes determining that the user has perceived the virtual content to a first level of perception of a plurality of levels of perception. In some examples, determining the level of perception of the virtual content by the user includes determining that the user has perceived the virtual content to a second level of perception of a plurality of levels of perception. In some aspects, the first level of perception is greater than the second level of perception, and the second level of perception is less than the first level of perception. In some aspects, the second level of perception is greater than the first level of perception, and the first level of perception is less than the second level of perception.

In some examples, determining the level of perception of the virtual content by the user includes determining a confidence level corresponding to the level of perception of the virtual content by the user. In some aspects, the modification to the display settings is based on the confidence level. The confidence level can be provided by a machine learning system, such as the attribute engine 230, the perception engine 235, the comprehension engine 240, the first trained ML model 825, the second trained ML model 835, the third trained ML model 865, the NN 900, or a combination thereof.

In some examples, determining the level of perception of the virtual content by the user includes identifying one or more gestures of the user, for instance using one or more sensors (e.g., image sensors, cameras, user-focused sensors 205, environment-focused sensors 210). The imaging system can track the user's hands using sensor data from the environment-focused sensors 210. For instance, the imaging system can determine if the user's hands are pointing and/or gesturing toward the virtual content, increasing the level of perception to a high level of perception. The imaging system can determine if the user's hands are pointing and/or gesturing away from the virtual content, decreasing the level of perception to a low level of perception.

In some examples, the virtual content includes a string of characters. The imaging system is configured to, and can, determine an extent of reading of the string of characters by the user based on the level of perception of the virtual content, a length of the string of characters, a complexity of the string of characters, and/or a uniqueness of the string of characters. The complexity and/or uniqueness of the string of characters can be an evaluation (e.g., evaluation 860) by a virtual content evaluation engine 245 of the imaging system. For example, if the level of perception indicates that the user has quickly glanced at the virtual content, but the string of characters is short, non-complex, and/or non-unique, then the extent of reading of the string of characters may be high nonetheless. On the other hand, if the level of perception indicates that the user has quickly glanced at the virtual content, but the string of characters is long, complex, and/or unique, then the extent of reading of the string of characters may be low. If the level of perception indicates that the user has looked at the virtual content for a very long time, then the extent of reading of the string of characters may be high, even if the string of characters is long, complex, and/or unique.

At operation 1015, the imaging system is configured to, and can, determine, based on the level of perception of the virtual content by the user, a modification to the display settings corresponding to the virtual content. Examples of the modification to the display settings include the modification from the first display settings 250 to the second display settings 255 in FIG. 2, the modification from the display settings 520 to the display settings 555 of FIGS. 5A-5B, the modification 875 to the display settings 837, or combinations thereof.

In some examples, the modification to the display settings corresponding to the virtual content includes causing the display to stop displaying at least a portion of the virtual content. An example of this is illustrated in FIG. 5B, with the modification from the display settings 520 to the display settings 555 causing the virtual content 535 to no longer be overlaid over the image 505 as illustrated in FIG. 5B. In some examples, the modification to the display settings corresponding to the virtual content includes causing the display to display at least a portion of the virtual content more prominently than before the modification. An example of this is illustrated in FIG. 5B, with the modification from the display settings 520 to the display settings 555 causing the virtual content 525 to increase in size, font size, and level of detail (amount of information), as illustrated in FIG. 5B. In some examples, the modification to the display settings corresponding to the virtual content includes a modification to one or more characteristics of the virtual content, wherein the one or more characteristics include at least one of a position, an orientation, a depth, a size, a color, a font size, a font color, a font, a language, a layout, or a combination thereof. An example of this is illustrated in FIG. 5B, with the modification from the display settings 520 to the display settings 555 causing the virtual content 525 to increase in size, font size, and level of detail (amount of information), and causing the virtual content 530 to change position and depth to appear partially behind the statue of Red Auerbach, as illustrated in FIG. 5B.

In some examples, the modification to the display settings is based on a likelihood that the virtual content is to be reviewed by the user in a threshold amount of time. For instance, in the example of the virtual content 730 of FIG. 7, the threshold amount of time can be short, since the car is rapidly approaching the user, and the modification can quickly increase the size of the virtual content 730 to ensure that the user is alerted if it appears unlikely (e.g., based on the level of perception and/or the level of comprehension) that the user will have reviewed the virtual content within the threshold time.

In some examples, the imaging system can include: means for causing virtual content to be displayed using a display according to display settings associated with the virtual content, wherein an environment is viewable using the display as the virtual content is displayed by the display; means for determining, based on one or more perception-related attributes of a user, a level of perception of the virtual content that is displayed using the display by the user; and means for determining, based on the level of perception of the virtual content by the user, a modification to the display settings corresponding to the virtual content.

In some examples, the means for causing the virtual content to be displayed includes, the image capture and processing system 100, the image capture device 105A, the image processing device 105B, the image processor 150, the ISP 154, the host processor 152, the XR system 200, the virtual content generator 215, the environment-facing sensor(s) 210, the compositor 220, the display 225, the display(s) 340, the first camera 330A, the second camera 330B, the display 440, the third camera 430C, the fourth camera 430D, the virtual content 525, the virtual content 530, the virtual content 535, the virtual content 630, the virtual content 730, the computing system 1100, or a combination thereof. In some examples, the means for determining the level of perception includes the image capture and processing system 100, the image capture device 105A, the image processing device 105B, the image processor 150, the ISP 154, the host processor 152, the XR system 200, the user-facing sensor(s) 205, the attribute engine 230, the perception engine 235, the comprehension engine 240, the virtual content scoring engine 245, the feedback engine 260, the first trained ML model 825, the second trained ML model 835, the third trained ML model 865, the NN 900, the computing system 1100, or a combination thereof. In some examples, the means determining the modification to the display settings includes the XR system 200, the compositor 220, the attribute engine 230, the perception engine 235, the comprehension engine 240, the virtual content scoring engine 245, the feedback engine 260, the first trained ML model 825, the second trained ML model 835, the third trained ML model 865, the NN 900, the computing system 1100, or a combination thereof.

In some examples, the processes described herein (e.g., processes of FIGS. 1, 2, 8, 9, 10, and/or other process described herein) may be performed by a computing device or apparatus. In some examples, the processes of FIGS. 1, 2, 8, 9, and/or 10 can be performed by the image capture and processing system 100, the image capture device 105A, the image processing device 105B, the image processor 150, the ISP 154, the host processor 152, the XR system 200, the HMD 310, mobile handset 410, the imaging device that captures the image 505 and overlays the virtual content 525-535, the imaging device that captures the image 605 and overlays the virtual content 630, the imaging device that captures the image 705 and overlays the virtual content 730, the imaging device of FIG. 8, the first trained ML model 825, of the second trained ML model 835, the third trained ML model 865, the neural network 900, the computing system 1100, the processor 1110, or a combination thereof.

The computing device can include any suitable device, such as a mobile device (e.g., a mobile phone), a desktop computing device, a tablet computing device, a wearable device (e.g., a VR headset, an AR headset, AR glasses, a network-connected watch or smartwatch, or other wearable device), a server computer, an autonomous vehicle or computing device of an autonomous vehicle, a robotic device, a television, and/or any other computing device with the resource capabilities to perform the processes described herein, including the processes of FIGS. 1, 2, 8, 9, and/or 10. In some cases, the computing device or apparatus may include various components, such as one or more input devices, one or more output devices, one or more processors, one or more microprocessors, one or more microcomputers, one or more cameras, one or more sensors, and/or other component(s) that are configured to carry out the steps of processes described herein. In some examples, the computing device may include a display, a network interface configured to communicate and/or receive the data, any combination thereof, and/or other component(s). The network interface may be configured to communicate and/or receive Internet Protocol (IP) based data or other type of data.

The components of the computing device can be implemented in circuitry. For example, the components can include and/or can be implemented using electronic circuits or other electronic hardware, which can include one or more programmable electronic circuits (e.g., microprocessors, graphics processing units (GPUs), digital signal processors (DSPs), central processing units (CPUs), and/or other suitable electronic circuits), and/or can include and/or be implemented using computer software, firmware, or any combination thereof, to perform the various operations described herein.

The processes of FIGS. 1, 2, 8, 9, and/or 10 are illustrated as logical flow diagrams, block diagrams, or conceptual diagrams, the operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be combined in any order and/or in parallel to implement the processes.

Additionally, the processes of FIGS. 1, 2, 8, 9, 10, and/or other processes described herein may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable or machine-readable storage medium, for example, in the form of a computer program comprising a plurality of instructions executable by one or more processors. The computer-readable or machine-readable storage medium may be non-transitory.

Figure 11:
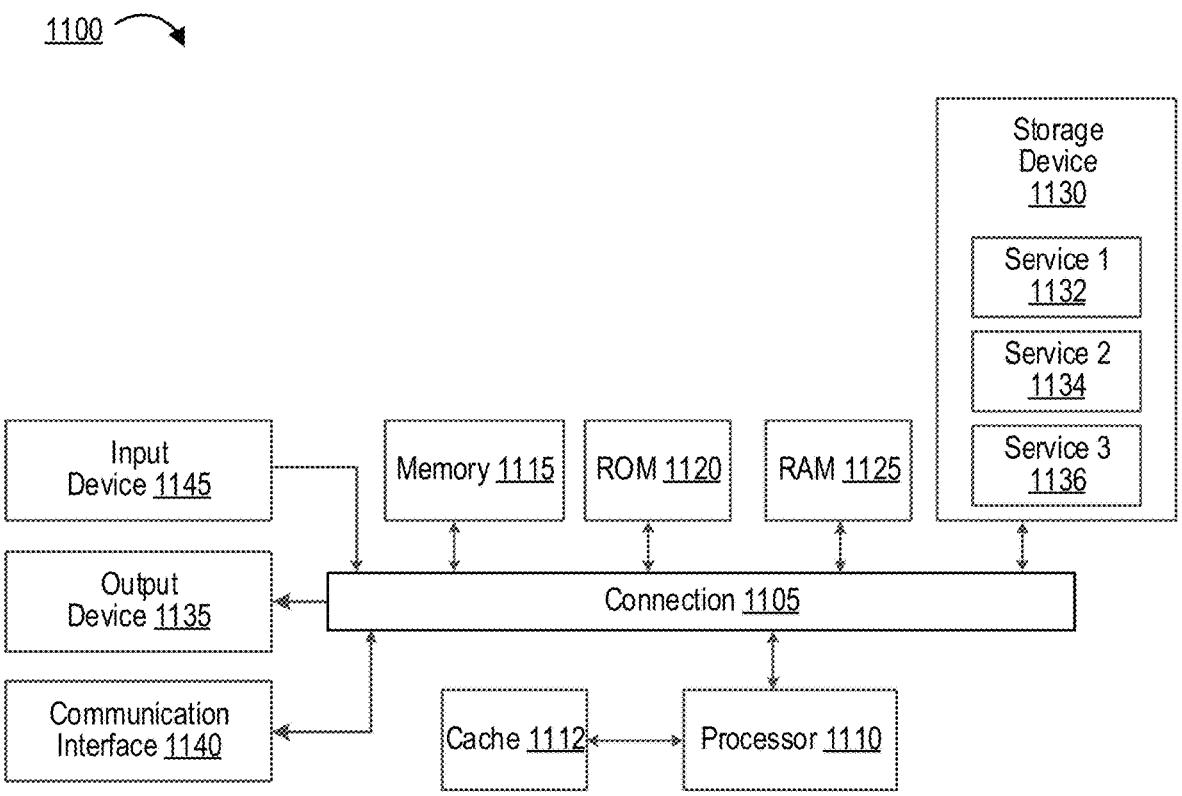
FIG. 11 is a diagram illustrating an example of a computing system for implementing certain aspects described herein.

FIG. 11 is a diagram illustrating an example of a system for implementing certain aspects of the present technology. In particular, FIG. 11 illustrates an example of computing system 1100, which can be for example any computing device making up internal computing system, a remote computing system, a camera, or any component thereof in which the components of the system are in communication with each other using connection 1105. Connection 1105 can be a physical connection using a bus, or a direct connection into processor 1110, such as in a chipset architecture. Connection 1105 can also be a virtual connection, networked connection, or logical connection.

In some embodiments, computing system 1100 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

Example system 1100 includes at least one processing unit (CPU or processor) 1110 and connection 1105 that couples various system components including system memory 1115, such as read-only memory (ROM) 1120 and random access memory (RAM) 1125 to processor 1110. Computing system 1100 can include a cache 1112 of high-speed memory connected directly with, in close proximity to, or integrated as part of processor 1110.

Processor 1110 can include any general purpose processor and a hardware service or software service, such as services 1132, 1134, and 1136 stored in storage device 1130, configured to control processor 1110 as well as a special-purpose processor where software instructions are incorporated into the actual processor design. Processor 1110 may essentially be a completely self-contained computing system, containing multiple cores or processors, a bus, memory controller, cache, etc. A multi-core processor may be symmetric or asymmetric.

To enable user interaction, computing system 1100 includes an input device 1145, which can represent any number of input mechanisms, such as a microphone for speech, a touch-sensitive screen for gesture or graphical input, keyboard, mouse, motion input, speech, etc. Computing system 1100 can also include output device 1135, which can be one or more of a number of output mechanisms. In some instances, multimodal systems can enable a user to provide multiple types of input/output to communicate with computing system 1100. Computing system 1100 can include communications interface 1140, which can generally govern and manage the user input and system output. The communication interface may perform or facilitate receipt and/or transmission wired or wireless communications using wired and/or wireless transceivers, including those making use of an audio jack/plug, a microphone jack/plug, a universal serial bus (USB) port/plug, an Apple® Lightning® port/plug, an Ethernet port/plug, a fiber optic port/plug, a proprietary wired port/plug, a BLUETOOTH® wireless signal transfer, a BLUETOOTH® low energy (BLE) wireless signal transfer, an IBEACON® wireless signal transfer, a radio-frequency identification (RFID) wireless signal transfer, near-field communications (NFC) wireless signal transfer, dedicated short range communication (DSRC) wireless signal transfer, 802.11 Wi-Fi wireless signal transfer, wireless local area network (WLAN) signal transfer, Visible Light Communication (VLC), Worldwide Interoperability for Microwave Access (WiMAX), Infrared (IR) communication wireless signal transfer, Public Switched Telephone Network (PSTN) signal transfer, Integrated Services Digital Network (ISDN) signal transfer, 3G/4G/5G/LTE cellular data network wireless signal transfer, ad-hoc network signal transfer, radio wave signal transfer, microwave signal transfer, infrared signal transfer, visible light signal transfer, ultraviolet light signal transfer, wireless signal transfer along the electromagnetic spectrum, or some combination thereof. The communications interface 1140 may also include one or more Global Navigation Satellite System (GNSS) receivers or transceivers that are used to determine a location of the computing system 1100 based on receipt of one or more signals from one or more satellites associated with one or more GNSS systems. GNSS systems include, but are not limited to, the US-based Global Positioning System (GPS), the Russia-based Global Navigation Satellite System (GLONASS), the China-based BeiDou Navigation Satellite System (BDS), and the Europe-based Galileo GNSS. There is no restriction on operating on any particular hardware arrangement, and therefore the basic features here may easily be substituted for improved hardware or firmware arrangements as they are developed.

Storage device 1130 can be a non-volatile and/or non-transitory and/or computer-readable memory device and can be a hard disk or other types of computer readable media which can store data that are accessible by a computer, such as magnetic cassettes, flash memory cards, solid state memory devices, digital versatile disks, cartridges, a floppy disk, a flexible disk, a hard disk, magnetic tape, a magnetic strip/stripe, any other magnetic storage medium, flash memory, memristor memory, any other solid-state memory, a compact disc read only memory (CD-ROM) optical disc, a rewritable compact disc (CD) optical disc, digital video disk (DVD) optical disc, a blu-ray disc (BDD) optical disc, a holographic optical disk, another optical medium, a secure digital (SD) card, a micro secure digital (microSD) card, a Memory Stick® card, a smartcard chip, a EMV chip, a subscriber identity module (SIM) card, a mini/micro/nano/pico SIM card, another integrated circuit (IC) chip/card, random access memory (RAM), static RAM (SRAM), dynamic RAM (DRAM), read-only memory (ROM), programmable read-only memory (PROM), erasable programmable read-only memory (EPROM), electrically erasable programmable read-only memory (EEPROM), flash EPROM (FLASHEPROM), cache memory (L1/L2/L3/L4/L5/L #), resistive random-access memory (RRAM/ReRAM), phase change memory (PCM), spin transfer torque RAM (STT-RAM), another memory chip or cartridge, and/or a combination thereof.

The storage device 1130 can include software services, servers, services, etc., that when the code that defines such software is executed by the processor 1110, it causes the system to perform a function. In some embodiments, a hardware service that performs a particular function can include the software component stored in a computer-readable medium in connection with the necessary hardware components, such as processor 1110, connection 1105, output device 1135, etc., to carry out the function.

As used herein, the term "computer-readable medium" includes, but is not limited to, portable or non-portable storage devices, optical storage devices, and various other mediums capable of storing, containing, or carrying instruction(s) and/or data. A computer-readable medium may include a non-transitory medium in which data can be stored and that does not include carrier waves and/or transitory electronic signals propagating wirelessly or over wired connections. Examples of a non-transitory medium may include, but are not limited to, a magnetic disk or tape, optical storage media such as compact disk (CD) or digital versatile disk (DVD), flash memory, memory or memory devices. A computer-readable medium may have stored thereon code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted using any suitable means including memory sharing, message passing, token passing, network transmission, or the like.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Specific details are provided in the description above to provide a thorough understanding of the embodiments and examples provided herein. However, it will be understood by one of ordinary skill in the art that the embodiments may be practiced without these specific details. For clarity of explanation, in some instances the present technology may be presented as including individual functional blocks including functional blocks comprising devices, device components, steps or routines in a method embodied in software, or combinations of hardware and software. Additional components may be used other than those shown in the figures and/or described herein. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Individual embodiments may be described above as a process or method which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

Processes and methods according to the above-described examples can be implemented using computer-executable instructions that are stored or otherwise available from computer-readable media. Such instructions can include, for example, instructions and data which cause or otherwise configure a general purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc. Examples of computer-readable media that may be used to store instructions, information used, and/or information created during methods according to described examples include magnetic or optical disks, flash memory, USB devices provided with non-volatile memory, networked storage devices, and so on.

Devices implementing processes and methods according to these disclosures can include hardware, software, firmware, middleware, microcode, hardware description languages, or any combination thereof, and can take any of a variety of form factors. When implemented in software, firmware, middleware, or microcode, the program code or code segments to perform the necessary tasks (e.g., a computer-program product) may be stored in a computer-readable or machine-readable medium. A processor(s) may perform the necessary tasks. Typical examples of form factors include laptops, smart phones, mobile phones, tablet devices or other small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the inventive concepts may be otherwise variously embodied and employed, and that the appended claims are intended to be construed to include such variations, except as limited by the prior art. Various features and aspects of the above-described application may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

One of ordinary skill will appreciate that the less than ("<") and greater than (">") symbols or terminology used herein can be replaced with less than or equal to ("≤") and greater than or equal to ("≥") symbols, respectively, without departing from the scope of this description.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The phrase "coupled to" refers to any component that is physically connected to another component either directly or indirectly, and/or any component that is in communication with another component (e.g., connected to the other component over a wired or wireless connection, and/or other suitable communication interface) either directly or indirectly.

Claim language or other language reciting "at least one of" a set and/or "one or more" of a set indicates that one member of the set or multiple members of the set (in any combination) satisfy the claim. For example, claim language reciting "at least one of A and B" means A, B, or A and B. In another example, claim language reciting "at least one of A, B, and C" means A, B, C, or A and B, or A and C, or B and C, or A and B and C. The language "at least one of" a set and/or "one or more" of a set does not limit the set to the items listed in the set. For example, claim language reciting "at least one of A and B" can mean A, B, or A and B, and can additionally include items not listed in the set of A and B.

The various illustrative logical blocks, modules, circuits, and algorithm steps described in connection with the embodiments disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

The program code may be executed by a processor, which may include one or more processors, such as one or more digital signal processors (DSPs), general purpose microprocessors, an application specific integrated circuits (ASICs), field programmable logic arrays (FPGAs), or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. In addition, in some aspects, the functionality described herein may be provided within dedicated software modules or hardware modules configured for encoding and decoding, or incorporated in a combined video encoder-decoder (CODEC).

Illustrative aspects of the disclosure include:

Aspect 1: An extended reality (XR) system, the apparatus comprising: a memory; and one or more processors coupled to the memory, the one or more processors configured to: cause virtual content to be displayed using a display according to display settings associated with the virtual content, wherein an environment is viewable using the display as the virtual content is displayed by the display; determine, based on one or more perception-related attributes of a user, a level of perception of the virtual content that is displayed using the display by the user; and determine, based on the level of perception of the virtual content by the user, a modification to the display settings corresponding to the virtual content.

Aspect 2. The XR system of Aspect 1, wherein the one or more perception-related attributes of the user are associated with one or more eyes of the user.

Aspect 3. The XR system of any of Aspects 1 to 2, wherein the environment is viewable using the display at least in part based on light from the environment passing through at least a portion of the display.

Aspect 4. The XR system of any of Aspects 1 to 3, wherein the environment is viewable using the display at least in part based on the one or more processors being configured to cause a view of the environment to be displayed by the display.

Aspect 5. The XR system of any of Aspects 1 to 4, wherein, to determine the level of perception of the virtual content by the user, the one or more processors are configured to use the one or more perception-related attributes of the user as inputs to one or more trained machine learning systems.

Aspect 6. The XR system of Aspect 5, wherein the one or more processors are configured to: receive, through a user interface, feedback corresponding to the level of perception of the virtual content by the user; and update the one or more trained machine learning systems based on the feedback.

Aspect 7. The XR system of any of Aspects 1 to 6, wherein the one or more processors are configured to: receive sensor data captured by one or more sensors, wherein the sensor data is indicative of one or more eyes of the user; and determine the one or more perception-related attributes of the user based on the sensor data.

Aspect 8. The XR system of Aspect 7, further comprising: the one or more sensors.

Aspect 9. The XR system of any of Aspects 1 to 8, wherein the one or more processors are configured to: determine the one or more perception-related attributes of the user based on sensor data captured by one or more image sensors, wherein the sensor data includes one or more images of one or more eyes of the user.

Aspect 10. The XR system of any of Aspects 1 to 9, wherein the one or more processors are configured to: determine a level of comprehension of the virtual content by the user based on the level of perception of the virtual content by the user, wherein to determine the modification to the display settings based on the level of perception, the one or more processors are configured to determine the modification to the display settings based on the level of comprehension.

Aspect 11. The XR system of Aspect 10, wherein the one or more processors are configured to: receive historical information associated with the user, wherein, to determine the level of comprehension of the virtual content by the user, the one or more processors are configured to determine the level of comprehension of the virtual content by the user based on the historical information about the user.

Aspect 12. The XR system of any of Aspects 1 to 11, wherein the one or more processors are configured to: determine a characteristic of the virtual content, wherein, to determine the level of perception of the virtual content by the user, the one or more processors are configured to determine the level of perception based further on the characteristic of the virtual content.

Aspect 13. The XR system of any of Aspects 1 to 12, wherein the one or more processors are configured to: determine a level of complexity of the virtual content, wherein, to determine the level of perception of the virtual content by the user, the one or more processors are configured to determine the level of perception based on the level of complexity of the virtual content.

Aspect 14. The XR system of any of Aspects 1 to 13, wherein the one or more processors are configured to: determine a level of uniqueness of the virtual content, wherein, to determine the level of perception of the virtual content by the user, the one or more processors are configured to determine the level of perception based on the level of uniqueness of the virtual content.

Aspect 15. The XR system of any of Aspects 1 to 14, wherein the modification to the display settings corresponding to the virtual content comprises causing the display to stop displaying at least a portion of the virtual content.

Aspect 16. The XR system of any of Aspects 1 to 15, wherein the modification to the display settings corresponding to the virtual content comprises causing the display to display at least a portion of the virtual content more prominently than before the modification.

Aspect 17. The XR system of any of Aspects 1 to 16, wherein the modification to the display settings corresponding to the virtual content comprises a modification to one or more characteristics of the virtual content, wherein the one or more characteristics include at least one of a position, an orientation, a depth, a size, a color, a font size, a font color, a font, a language, and a layout.

Aspect 18. The XR system of any of Aspects 1 to 17, wherein, to determine the level of perception of the virtual content by the user, the one or more processors are configured to determine that the user has perceived the virtual content.

Aspect 19. The XR system of any of Aspects 1 to 18, wherein, to determine the level of perception of the virtual content by the user, the one or more processors are configured to determine that the user has not perceived the virtual content.

Aspect 20. The XR system of any of Aspects 1 to 19, wherein the modification to the display settings is based on a likelihood that the virtual content is to be reviewed by the user in a threshold amount of time.

Aspect 21. The XR system of any of Aspects 1 to 20, wherein, to determine the level of perception of the virtual content by the user, the one or more processors are configured to determine a confidence level corresponding to the level of perception of the virtual content by the user, wherein the modification to the display settings is based on the confidence level.

Aspect 22. The XR system of any of Aspects 1 to 21, wherein the one or more perception-related attributes of the user include one or more eye positions of one or more eyes of the user relative to the virtual content.

Aspect 23. The XR system of any of Aspects 1 to 22, wherein the one or more perception-related attributes of the user include one or more characteristics of one or more saccades by one or more eyes of the user, wherein the one or more characteristics include at least one of a frequency, a duration, a timing, a saccade speed, a saccade amplitude, an eye position, and an eye movement.

Aspect 24. The XR system of any of Aspects 1 to 23, wherein the one or more perception-related attributes of the user include one or more characteristics of one or more fixations by one or more eyes of the user, wherein the one or more characteristics include at least one of a frequency, a duration, a timing, an eye position, and an eye movement.

Aspect 25. The XR system of any of Aspects 1 to 24, wherein the one or more perception-related attributes of the user include one or more characteristics of one or more pupil dilations by one or more eyes of the user, wherein the one or more characteristics include at least one of a frequency, a duration, a timing, a level of pupil dilation, an eye position, and an eye movement.

Aspect 26. The XR system of any of Aspects 1 to 25, wherein the one or more perception-related attributes of the user include one or more characteristics of one or more blinks by one or more eyelids of the user, wherein the one or more characteristics include at least one of a frequency, a duration, a timing, a blink speed, an eye position, and an eye movement.

Aspect 27. The XR system of any of Aspects 1 to 26, wherein the one or more perception-related attributes of the user include one or more characteristics of one or more squints by one or more eyelids of the user, wherein the one or more characteristics include at least one of a frequency, a duration, a timing, a level of squinting, an eye position, and an eye movement.

Aspect 28. The XR system of any of Aspects 1 to 27, wherein the one or more processors are configured to: determine an extent of reading of a string of characters by the user based on the level of perception of the virtual content and a length of the string of characters, wherein the virtual content includes the string of characters.

Aspect 29. The XR system of any of Aspects 1 to 28, further comprising: the display.

Aspect 30. The XR system of any of Aspects 1 to 29, wherein the XR system includes at least one of a mobile handset, a wireless communication device, and a head-mounted display.

Aspect 31. The XR system of any of Aspects 1 to 30, wherein the one or more processors are configured to: determine a level of distinctiveness of the virtual content relative to the environment, wherein, to determine the level of perception of the virtual content by the user, the one or more processors are configured to determine the level of perception based on the level of distinctiveness of the virtual content relative to the environment.

Aspect 32. The XR system of any of Aspects 1 to 31, wherein the one or more processors are configured to: determine, based at least in part on sensor data that includes a representation of one or more eyes of the user, at least one of the one or more perception-related attributes of the user, wherein one or more sensors are configured to capture the sensor data.

Aspect 33. The XR system of any of Aspects 1 to 32, wherein the one or more perception-related attributes of the user include at least one of: one or more attributes of one or more eyes of the user, one or more attributes of one or more facial expressions of the user, and one or more gestures of the user.

Aspect 34. The XR system of any of Aspects 1 to 33, wherein, to determine the level of perception of the virtual content by the user, the one or more processors are configured to determine a level of comprehension of the virtual content by the user based on the one or more perception-related attributes of the user.

Aspect 35. The XR system of Aspect 34, wherein to determine the level of comprehension of the virtual content by the user, the one or more processors are configured to determine the level of comprehension of the virtual content by the user based on the one or more perception-related attributes of the user and at least one of: one or more characteristics of the virtual content, contextual data, and a user profile of the user.

Aspect 36. The XR system of Aspect 35, wherein the user profile comprises historical data associated with the user.

Aspect 37. The XR system of any of Aspects 35 or 36, wherein the contextual data comprises one or more reactions by the user to the virtual content.

Aspect 38. The XR system of any of Aspects 35 to 37, wherein the contextual data comprises a location of the XR system.

Aspect 39. The XR system of any of Aspects 1 to 38, wherein, to determine the level of perception of the virtual content by the user, the one or more processors are configured to determine that the user has perceived the virtual content to a first level of perception of a plurality of levels of perception.

Aspect 40. The XR system of any of Aspects 1 to 39, wherein, to determine the level of perception of the virtual content by the user, the one or more processors are configured to determine that the user has perceived the virtual content to a second level of perception of a plurality of levels of perception.

Aspect 41. A method of extended reality (XR) operations, the method comprising: causing virtual content to be displayed using a display according to display settings associated with the virtual content, wherein an environment is viewable using the display as the virtual content is displayed by the display; determining, based on one or more perception-related attributes of a user, a level of perception of the virtual content that is displayed using the display by the user; and determining, based on the level of perception of the virtual content by the user, a modification to the display settings corresponding to the virtual content.

Aspect 42. The method of Aspect 41, wherein the one or more perception-related attributes of the user are associated with one or more eyes of the user.

Aspect 43. The method of any of Aspects 41 to 42, wherein the environment is viewable using the display at least in part based on light from the environment passing through at least a portion of the display.

Aspect 44. The method of any of Aspects 41 to 43, wherein the environment is viewable using the display at least in part based on causing a view of the environment to be displayed by the display.

Aspect 45. The method of any of Aspects 41 to 44, wherein determining the level of perception of the virtual content by the user includes using the one or more perception-related attributes of the user as inputs to one or more trained machine learning systems.

Aspect 46. The method of Aspect 45, further comprising: receiving, through a user interface, feedback corresponding to the level of perception of the virtual content by the user; and updating the one or more trained machine learning systems based on the feedback.

Aspect 47. The method of any of Aspects 41 to 46, further comprising: receiving sensor data captured by one or more sensors, wherein the sensor data is indicative of one or more eyes of the user; and determining the one or more perception-related attributes of the user based on the sensor data.

Aspect 48. The method of any of Aspects 41 to 47, wherein the method is performed by an XR system that includes the one or more sensors.

Aspect 49. The method of any of Aspects 41 to 48, further comprising: determining the one or more perception-related attributes of the user based on sensor data captured by one or more image sensors, wherein the sensor data includes one or more images of one or more eyes of the user.

Aspect 50. The method of any of Aspects 41 to 49, further comprising: determining a level of comprehension of the virtual content by the user based on the level of perception of the virtual content by the user, wherein determining the modification to the display settings based on the level of perception includes determining the modification to the display settings based on the level of comprehension.

Aspect 51. The method of Aspect 50, further comprising: receiving historical information associated with the user, wherein determining the level of comprehension of the virtual content by the user is based on the historical information about the user.

Aspect 52. The method of any of Aspects 41 to 51, further comprising: determining a characteristic of the virtual content, wherein determining the level of perception of the virtual content by the user is based on the characteristic of the virtual content.

Aspect 53. The method of any of Aspects 41 to 52, further comprising: determining a level of complexity of the virtual content, wherein determining the level of perception of the virtual content by the user is based on the level of complexity of the virtual content.

Aspect 54. The method of any of Aspects 41 to 53, further comprising: determining a level of uniqueness of the virtual content, wherein determining the level of perception of the virtual content by the user is based on the level of uniqueness of the virtual content.

Aspect 55. The method of any of Aspects 41 to 54, wherein the modification to the display settings corresponding to the virtual content comprises causing the display to stop displaying at least a portion of the virtual content.

Aspect 56. The method of any of Aspects 41 to 55, wherein the modification to the display settings corresponding to the virtual content comprises causing the display to display at least a portion of the virtual content more prominently than before the modification.

Aspect 57. The method of any of Aspects 41 to 56, wherein the modification to the display settings corresponding to the virtual content comprises a modification to one or more characteristics of the virtual content, wherein the one or more characteristics include at least one of a position, an orientation, a depth, a size, a color, a font size, a font color, a font, a language, and a layout.

Aspect 58. The method of any of Aspects 41 to 57, wherein determining the level of perception of the virtual content by the user includes determining that the user has perceived the virtual content.

Aspect 59. The method of any of Aspects 41 to 58, wherein determining the level of perception of the virtual content by the user includes determining that the user has not perceived the virtual content.

Aspect 60. The method of any of Aspects 41 to 59, wherein the modification to the display settings is based on a likelihood that the virtual content is to be reviewed by the user in a threshold amount of time.

Aspect 61. The method of any of Aspects 41 to 60, wherein determining the level of perception of the virtual content by the user includes determining a confidence level corresponding to the level of perception of the virtual content by the user, wherein the modification to the display settings is based on the confidence level.

Aspect 62. The method of any of Aspects 41 to 61, wherein the one or more perception-related attributes of the user include one or more eye positions of one or more eyes of the user relative to the virtual content.

Aspect 63. The method of any of Aspects 41 to 62, wherein the one or more perception-related attributes of the user include one or more characteristics of one or more saccades by one or more eyes of the user, wherein the one or more characteristics include at least one of a frequency, a duration, a timing, a saccade speed, a saccade amplitude, an eye position, and an eye movement.

Aspect 64. The method of any of Aspects 41 to 63, wherein the one or more perception-related attributes of the user include one or more characteristics of one or more fixations by one or more eyes of the user, wherein the one or more characteristics include at least one of a frequency, a duration, a timing, an eye position, and an eye movement.

Aspect 65. The method of any of Aspects 41 to 64, wherein the one or more perception-related attributes of the user include one or more characteristics of one or more pupil dilations by one or more eyes of the user, wherein the one or more characteristics include at least one of a frequency, a duration, a timing, a level of pupil dilation, an eye position, and an eye movement.

Aspect 66. The method of any of Aspects 41 to 65, wherein the one or more perception-related attributes of the user include one or more characteristics of one or more blinks by one or more eyelids of the user, wherein the one or more characteristics include at least one of a frequency, a duration, a timing, a blink speed, an eye position, and an eye movement.

Aspect 67. The method of any of Aspects 41 to 66, wherein the one or more perception-related attributes of the user include one or more characteristics of one or more squints by one or more eyelids of the user, wherein the one or more characteristics include at least one of a frequency, a duration, a timing, a level of squinting, an eye position, and an eye movement.

Aspect 68. The method of any of Aspects 41 to 67, further comprising: determining an extent of reading of a string of characters by the user based on the level of perception of the virtual content and a length of the string of characters, wherein the virtual content includes the string of characters.

Aspect 69. The method of any of Aspects 41 to 68, wherein the method is performed by an XR system that includes the display.

Aspect 70. The method of any of Aspects 41 to 69, wherein the method is performed by an XR system that includes at least one of a mobile handset, a wireless communication device, and a head-mounted display.

Aspect 71. The method of any of Aspects 41 to 70, further comprising: determining a level of distinctiveness of the virtual content relative to the environment, wherein determining the level of perception of the virtual content by the user is based on the level of distinctiveness of the virtual content relative to the environment.

Aspect 72. The method of any of Aspects 41 to 71, further comprising: determining, based at least in part on sensor data that includes a representation of one or more eyes of the user, at least one of the one or more perception-related attributes of the user, wherein one or more sensors are configured to capture the sensor data.

Aspect 73. The method of any of Aspects 41 to 72, wherein the one or more perception-related attributes of the user include at least one of: one or more attributes of one or more eyes of the user, one or more attributes of one or more facial expressions of the user, and one or more gestures of the user.

Aspect 74. The method of any of Aspects 41 to 73, wherein determining the level of perception of the virtual content by the user includes determining a level of comprehension of the virtual content by the user based on the one or more perception-related attributes of the user.

Aspect 75. The method of Aspect 74, wherein determining the level of comprehension of the virtual content by the user is based on the one or more perception-related attributes of the user and at least one of: one or more characteristics of the virtual content, contextual data, and a user profile of the user.

Aspect 76. The method of Aspect 75, wherein the user profile comprises historical data associated with the user.

Aspect 77. The method of any of Aspects 75 or 76, wherein the contextual data comprises one or more reactions by the user to the virtual content.

Aspect 78. The method of any of Aspects 75 to 77, wherein the method is performed by an XR system, wherein the contextual data comprises a location of the XR system.

Aspect 79. The method of any of Aspects 41 to 78, wherein determining the level of perception of the virtual content by the user includes determining that the user has perceived the virtual content to a first level of perception of a plurality of levels of perception.

Aspect 80. The method of any of Aspects 41 to 79, wherein determining the level of perception of the virtual content by the user includes determining that the user has perceived the virtual content to a second level of perception of a plurality of levels of perception.

Aspect 81: A non-transitory computer-readable medium having stored thereon instructions that, when executed by one or more processors, cause the one or more processors to: cause virtual content to be displayed using a display according to display settings associated with the virtual content, wherein an environment is viewable using the display as the virtual content is displayed by the display; determine, based on one or more perception-related attributes of a user, a level of perception of the virtual content that is displayed using the display by the user; and determine, based on the level of perception of the virtual content by the user, a modification to the display settings corresponding to the virtual content.

Aspect 82: The non-transitory computer-readable medium of Aspect 81, further comprising any of Aspects 2 to 40, and/or any of Aspects 42 to 80.

Aspect 83: An apparatus for image processing, the apparatus comprising: means for causing virtual content to be displayed using a display according to display settings associated with the virtual content, wherein an environment is viewable using the display as the virtual content is displayed by the display; means for determining, based on one or more perception-related attributes of a user, a level of perception of the virtual content that is displayed using the display by the user; and means for determining, based on the level of perception of the virtual content by the user, a modification to the display settings corresponding to the virtual content.

Aspect 84: The apparatus of Aspect 83, further comprising any of Aspects 2 to 40, and/or any of Aspects 42 to 80.

What is claimed is:

1. An extended reality (XR) system comprising:
at least one memory; and
at least one processor coupled to the at least one memory, the at least one processor configured to:
cause virtual content to be displayed according to display settings associated with the virtual content, wherein an environment is viewable using the display as the virtual content is displayed by the display, and wherein the virtual content has a level of complexity;
track a gaze of a user relative to the virtual content as the virtual content is displayed to determine a duration of the gaze of the user relative to the virtual content;
determine, based on at least a comparison between the duration of the gaze of the user relative to the virtual content and at least one duration threshold, a level of comprehension by the user of the virtual content that is displayed, wherein the at least one duration threshold is based on the level of complexity of the virtual content; and
determine, based on the level of comprehension by the user of the virtual content, a modification to the display settings is configured to change how prominently the virtual content is configured to be displayed.

2. The XR system of claim 1, the at least one processor configured to:
determine, based on the gaze of the user relative to the virtual content as tracked, at least one perception-related attribute of the user that is associated with at least one eye of the user.

3. The XR system of claim 1, wherein the environment is viewable using the display at least in part based on light from the environment passing through at least a portion of the display.

4. The XR system of claim 1, wherein the environment is viewable at least in part based on the at least one processor being configured to cause a view of the environment to be displayed by the display.

5. The XR system of claim 1, wherein the at least one processor is configured to use at least one perception-related attribute of the user as at least one input to at least one trained machine learning model to determine the level of comprehension by the user of the virtual content, the at least one perception-related attribute of the user being associated with the gaze of the user relative to the virtual content as tracked.

6. The XR system of claim 5, the at least one processor configured to:
receive, through a user interface, feedback corresponding to the level of comprehension by the user of the virtual content; and
update the at least one trained machine learning model based on the feedback.

7. The XR system of claim 1, the at least one processor configured to:
receive sensor data captured by sensors at least one sensor, wherein the sensor data is indicative of at least one eye of the user; and
determine the duration of the gaze of the user relative to the virtual content based on the sensor data.

8. The XR system of claim 7, further comprising:
the at least one sensor.

9. The XR system of claim 1, the at least one processor configured to:
determine the duration of the gaze of the user relative to the virtual content based on at least one image of at least one eye of the user captured using at least one image sensor to determine the duration of the gaze.

10. The XR system of claim 1, the at least one processor configured to:
determine a level of perception by the user of the virtual content to determine the level of comprehension by the user of the virtual content.

11. The XR system of claim 10, the at least one processor configured to:
receive historical information associated with the user, wherein, to determine the level of comprehension of the virtual content by the user, the at least one processor is configured to determine the level of comprehension of the virtual content by the user based on the historical information about the user.

12. The XR system of claim 1, the at least one processor configured to:
determine a characteristic of the virtual content, wherein, to determine the level of perception of the virtual content by the user, the at least one processor is configured to determine the level of perception based further on the characteristic of the virtual content.

13. The XR system of claim 1, the at least one processor configured to:
determine the level of complexity of the virtual content.

14. The XR system of claim 1, the at least one processor configured to:
determine a level of similarity of the virtual content to previously-displayed virtual content; and
determine the level of comprehension by the user based on the level of similarity of the virtual content to the previously-displayed virtual content to determine the level of comprehension by the user of the virtual content.

15. The XR system of claim 1, wherein the modification to the display settings corresponding to the virtual content is configured to cause the display to stop displaying at least a portion of the virtual content.

16. The XR system of claim 1, wherein the modification to the display settings is configured to cause the display to display at least a portion of the virtual content more prominently than the virtual content is configured to be displayed before the modification.

17. The XR system of claim 1, wherein the modification to the display settings corresponding to the virtual content is configured to cause a modification to at least one characteristic of the virtual content, wherein the at least one characteristic includes at least one of a position, an orientation, a depth, a size, a color, a font size, a font color, a font, a language, or a layout.

18. The XR system of claim 1, the at least one processor configured to determine that the user has perceived the virtual content to determine the level of comprehension by the user of the virtual content.

19. The XR system of claim 1, the at least one processor configured to determine that the user has not perceived the virtual content to determine the level of comprehension by the user of the virtual content.

20. The XR system of claim 1, wherein the modification to the display settings is based on a likelihood that the virtual content is to be reviewed by the user in a certain amount of time.

21. The XR system of claim 1, the at least one processor configured to determine a confidence level corresponding to the level of perception comprehension by the user of the virtual content to determine the level of comprehension by the user of the virtual content, wherein the modification to the display settings is based on the confidence level.

22. The XR system of claim 2, wherein the at least one perception-related attribute of the user includes at least one eye position of the at least one eye of the user relative to the virtual content.

23. The XR system of claim 2, wherein the at least one perception-related attribute of the user includes at least one characteristic of at least one saccade by the at least one eye of the user, wherein the at least one characteristic includes at least one of a frequency, a duration, a timing, a saccade speed, a saccade amplitude, an eye position, or an eye movement.

24. The XR system of claim 2, wherein the at least one perception-related attribute of the user includes at least one characteristic of at least one fixation by the at least one eye of the user, wherein the at least one characteristic includes at least one of a frequency, a duration, a timing, an eye position, or an eye movement.

25. The XR system of claim 2, wherein the at least one perception-related attribute of the user includes at least one characteristic of at least one pupil dilation by the at least one eye of the user, wherein the at least one characteristic includes at least one of a frequency, a duration, a timing, a level of pupil dilation, an eye position, or an eye movement.

26. The XR system of claim 2, wherein the at least one perception-related attribute of the user includes at least one characteristic of at least one blink by at least one eyelid of the at least one eye of the user, wherein the at least one characteristic includes at least one of a frequency, a duration, a timing, a blink speed, an eye position, and an eye movement.

27. The XR system of claim 2, wherein the at least one perception-related attribute of the user includes at least one characteristic of at least one squint by at least one eyelid of the at least one eye of the user, wherein the at least one characteristic includes at least one of a frequency, a duration, a timing, a level of squinting, an eye position, or an eye movement.

28. The XR system of claim 1, the at least one processor is configured to:
 determine an extent of reading of a string of characters by the user based on at least the level of comprehension by the user of the virtual content and a length of the string of characters, wherein the virtual content includes the string of characters.

29. The XR system of claim 1, further comprising: the display.

30. A method of extended reality (XR) operations, the method comprising:
 causing virtual content to be displayed according to display settings associated with the virtual content, wherein an environment is viewable as the virtual content is displayed by the display, and wherein the virtual content has a level of complexity;
 tracking a gaze of a user relative to the virtual content as the virtual content is displayed to determine a duration of the gaze of the user relative to the virtual content;
 determining, based on at least a comparison between the duration of the gaze of the user relative to the virtual content and at least one duration threshold, a level of comprehension by the user of the virtual content that is displayed, wherein the at least one duration threshold is based on the level of complexity of the virtual content; and
 determining, based on the level of comprehension by the user of the virtual content, a modification to the display settings is configured to change how prominently the virtual content is configured to be displayed.

31. The method of claim 30, wherein determining the level of comprehension by the user of the virtual content includes using at least one perception-related attribute of the user as at least one input to at least one trained machine learning model.

32. The method of claim 30, wherein determining the duration of the gaze of the user relative to the virtual content is based on at least one image of at least one eye of the user captured using at least one image sensor.

33. The method of claim 30, further comprising:
 determining a level of perception by the user of the virtual content by the user to determine the level of comprehension by the user of the virtual content.

34. The method of claim 30, further comprising:
 determining the level of complexity of the virtual content.

35. The method of claim 30, further comprising:
 determining a level of similarity of the virtual content to previously-displayed virtual content, wherein determining the level of comprehension by the user of the virtual content by the user is based on the level of similarity of the virtual content to the previously-displayed virtual content.

36. The XR system of claim 1, wherein, to change how prominently the virtual content is configured to be displayed, the modification to the display settings is configured to change at least one of a position of the virtual content, an orientation of the virtual content, a depth of the virtual content, a size of the virtual content, a color of the virtual content, a font size of the virtual content, a font color of the virtual content, a font of the virtual content, a language of the virtual content, a layout of the virtual content, a level of detail of the virtual content, or an amount of content included in the virtual content.

* * * * *